US012569503B2

(12) United States Patent
Grenning et al.

(10) Patent No.: US 12,569,503 B2
(45) Date of Patent: Mar. 10, 2026

(54) METHODS AND COMPOSITIONS FOR SUBSTITUTED AXIALLY-CHIRAL CANNABINOL ANALOGS

(71) Applicant: University of Florida Research Foundation, Inc., Gainesville, FL (US)

(72) Inventors: Alexander James Grenning, Gainesville, FL (US); Primali Vasundera Navaratne, Gainesville, FL (US)

(73) Assignee: University of Florida Research Foundation, Inc., Gainesville, GA (US)

( * ) Notice: Subject to any disclaimer, the term of this patent is extended or adjusted under 35 U.S.C. 154(b) by 951 days.

(21) Appl. No.: 17/435,901

(22) PCT Filed: Mar. 4, 2020

(86) PCT No.: PCT/US2020/020947

§ 371 (c)(1),
(2) Date: Sep. 2, 2021

(87) PCT Pub. No.: WO2020/180960

PCT Pub. Date: Sep. 10, 2020

(65) Prior Publication Data

US 2022/0106284 A1 Apr. 7, 2022

Related U.S. Application Data

(60) Provisional application No. 62/943,483, filed on Dec. 4, 2019, provisional application No. 62/889,303, filed on Aug. 20, 2019, provisional application No. 62/813,710, filed on Mar. 4, 2019.

(51) Int. Cl.

| | |
|---|---|
| ***A61K 31/00*** | (2006.01) |
| ***C07B 53/00*** | (2006.01) |
| ***C07D 311/80*** | (2006.01) |

(52) U.S. Cl.

CPC ............ *A61K 31/658* (2023.05); *C07B 53/00* (2013.01); *C07D 311/80* (2013.01); *C07B 2200/07* (2013.01)

(58) Field of Classification Search

None

See application file for complete search history.

(56) References Cited

U.S. PATENT DOCUMENTS

| | | | |
|---|---|---|---|
| 6,630,507 | B1 | 10/2003 | Hampson et al. |
| 2018/0064055 | A1 | 3/2018 | Lewis et al. |

OTHER PUBLICATIONS

Database Registry Chemical Abstracts Service, Columbus, Ohio, Accession No. RN 521-35-7, Entered STN: Nov. 16, 1984.*

Database Registry Chemical Abstracts Service, Columbus, Ohio, Accession No. RN 59652-23-2, Entered STN: Nov. 16, 1984.*

CAS Registry Number: RN 56264-02-9. [Database Registry Chemical Abstracts Service, Columbus, Ohio, Accession No. RN 56264-02-9, Entered STN: Nov. 16, 1984] (Year: 1984).*

Navaratne et al., Axially Chiral Cannabinols: A New Platform for Cannabinoid-Inspired Drug Discovery, Wiley Online Library, ChemMedChem (2020), 15, (728-732).

PubChem-CID-136047, Create Date: Mar. 27, 2005 (Mar. 27, 2005), entire document, especially: p. 2, Fig; p. 5, Chemical and Physical Properties.

Rom et al. "Cannabinoid receptor 2: Potential role in immunomodulation and neuroinflammation Review", J Neuroimmune Pharmacol. 2013. vol. 8(3), pp. 608-620, entire document.

International Search Report and Written Opinion for PCT/US2020/20947 mailed Jul. 9, 2020.

Rom et al. "Cannabinoid receptor 2: Potential role in immunomodulalion and neuroinflammation Review", J Neuroimmune Pharmacol. 2013. vol. 8(3), pp. 608-620.

* cited by examiner

*Primary Examiner* — Adam C Milligan

*Assistant Examiner* — Jed A Kucharczk

(74) *Attorney, Agent, or Firm* — Thomasl Horstemeyer, LLP

(57) ABSTRACT

In one aspect, the disclosure relates to substituted axially-chiral cannabinol analogs, methods of making same, pharmaceutical compositions comprising same, and methods of treating pain using same. This abstract is intended as a scanning tool for purposes of searching in the particular art and is not intended to be limiting of the present disclosure.

4 Claims, 33 Drawing Sheets dibenzopyran numbering ground state dihedral angle (θ) = 38° | barrier to atropisomerism = 17 kcal·mol$^{-1}$ | level of theory: wB97X-6-31G(d)

*$CH_3$ in lieu of $C_5H_{11}$ for computational analysis 4.7

4.8 ax-CBN ax-CBN ax-CBN-analogs ax-CBN 6.1

9,10-dimethyl-ax-CBN 6.2

DMH-ax-CBN 6.1 6.2

*9,10-dimethyl-DMH-ax*-CBN 7.1 (4.6 in Fig. 4)

7.2

7.3

9,10-dimethyl-ax-CBN 7.3a

9-OH-10-methyl-ax-CBN 7.3b

9-$CF_3$-10-methyl-ax-CBN 7.3c

9-F-10-methyl-ax-CBN 7.3d

9-I-10-methyl-ax-CBN 7.3e

9-Ar-10-methyl-ax-CBN 7.3f $^1H$ spectrum of 2-methoxy-6-((2-methylbut-3-yn-2-yl)oxy)-4-pentylbenzaldehyde #a ($CDCl_3$)

$^1H$ spectrum of 2-(2-methoxy-6-((2-methylbut-3-yn-2-yl)oxy)-4-pentylbenzylidene)but-3-enenitrile #a ($CDCl_3$)

$^{13}C$ spectrum of 2-(2-methoxy-6-((2-methylbut-3-yn-2-yl)oxy)-4-pentylbenzylidene)but-3-enenitrile #a ($CDCl_3$)

$^1H$ spectrum of 1-methoxy-6,6-dimethyl-3-pentyl-8,10a-dihydro-6H-benzo[c]chromene-10-carbonitrile #a ($CDCl_3$)

$^1H$ spectrum of 1-methoxy-6,6-dimethyl-3-pentyl-6H-benzo[c]chromene-10-carbonitrile #a ($CDCl_3$)

[1]H spectrum of 9,9-dimethyl-2-pentyl-5H,9H-isochromeno[5,4,3-cde]chromen-5-one #a ($CDCl_3$)

$^{13}C$ spectrum of 9,9-dimethyl-2-pentyl-5H,9H-isochromeno[5,4,3-cde]chromen-5-one #a ($CDCl_3$)

$^1H$ spectrum of 10-(hydroxymethyl)-6,6-dimethyl-3-pentyl-6H-benzo[c]chromen-1-ol #a ($CDCl_3$)

$^1H$ spectrum of (1-acetoxy-6,6-dimethyl-3-pentyl-6H-benzo[c]chromen-10-yl)methyl acetate #a ($CDCl_3$)

METHODS AND COMPOSITIONS FOR SUBSTITUTED AXIALLY-CHIRAL CANNABINOL ANALOGS

CROSS-REFERENCE TO RELATED APPLICATIONS

This application is a National Phase Application of International Application No. PCT/US2020/020947, filed Mar. 4, 2020, and claims the benefit of U.S. Provisional Application No. 62/813,710, filed on Mar. 4, 2019, 62/889,303, filed on Aug. 20, 2019, and 62/943,483, filed on Dec. 4, 2019, each of which is incorporated herein by reference in its entirety.

BACKGROUND

Cannabinoids have captured human interest for millennia. They are most infamously known for their psychoactive properties. Records suggest that humans have known about cannabis intoxication since ~2000 BCE. Medicinal applications have also been known and examined in both folk and modern medicine. Of particular importance, cannabinoids have been utilized as analgesics with first recorded use in this regard dating back to the Eastern Han Dynasty (25-220 CE). Much more recently, cannabinoids have been suggested as alternatives to opioids for managing pain. Identifying non-opioids for pain management is of critical importance, considering the opioid epidemic currently crippling the United States and other countries.

The current opioid crisis has fueled renewed focus on non-opioid analgesics, including cannabinoid receptor ligands. Phytocannabinoid-based analog development has mainly focused on the tetrahydrocannabinol (THC) scaffold. THC analogs (THCs) are prepared, generally speaking, by one general method, the "biomimetic route," (FIG. 1B) where a cyclic monoterpene derivative and a phenolic component serve as starting materials. Though effective for certain core substitution patterns, one route is inherently limiting (e.g. the biomimetic route is excellent at achieving diversification to the benzenoid portion of the THC scaffold, but less effective for other regions). Furthermore, THCs have limited bench-stability/shelf-life as they tend to isomerize and oxidize to the less bioactive cannabinol (CBN) scaffold. In this regard, a major difference between THC and CBN is that THC is three-dimensional courtesy of its chiral centers and significant $sp^3$-atom content whereas CBN is essentially planar (FIG. 2A). Thus, their occupation of space and bioactivity are markedly different: structure=function. Thus, these longstanding approaches to creating phytocannabinoid-inspired architectures, while still promising, have not unlocked the full potential of THC-based drug development.

In order to make headway on cannabinoid analgesic development, new routes to novel cannabinoid architectures having unprecedented substitution patterns and scaffolds need to be established. The conventional route for preparing cannabinoid analogs relies on the coupling of an appropriate monoterpene with a resorcinol derivative (e.g. olivetol). Due to the ready availability of resorcinol derivatives, this approach is most effective at creating targets and analogs whereby arene-substitution can be varied. Other syntheses, in particular the routes disclosed by Trost, Carreira, and Leahy, which establish a key allylic C—C bond by either allylic alkylation or an Ireland-Claisen reaction, may also find extended use in analog development due to the synthetic brevity. However, one major challenge associated with cannabinoid drug development is the instability of the tetrahydrocannabinol (THC) oxidation state: these scaffolds tend to oxidize easily to their less bioactive cannabinol (CBN) counterparts A potentially interesting class of cannabinols are axially-chiral cannabinols (ax-CBN), which may have similar biological profiles to parent tetrahydrocannabinols (THC), but with improved stability and drug-like properties. Unfortunately, suitably facile and useful synthetic methods currently do not exist to prepare ax-CBN compounds.

Despite advances in research directed to stable, diverse, and useful cannabinols and to phytocannabinoid analogs, there is still a scarcity of such compounds, in particular, ax-CBN compounds, and methods for making the same. These needs and other needs are satisfied by the present disclosure.

SUMMARY

In accordance with the purpose(s) of the present disclosure, as embodied and broadly described herein, the disclosure, in one aspect, relates to substituted axially-chiral cannabinol analogs, methods of making same, pharmaceutical compositions comprising same, and methods of treating pain using same.

Disclosed herein are compounds having a structure represented by a formula:

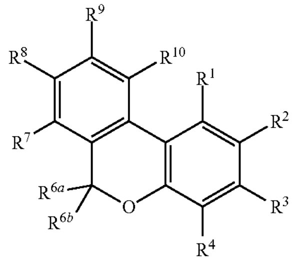

wherein $R^1$ is selected from hydrogen, halo, cyano, amino, hydroxyl, methoxy, acetoxy, —$OC_6H_5$, and —$CH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alky-heterocycloalkyl; wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alky-heteroaryl, optionally substituted —(C0-C12 alky-cycloalkyl, and optionally substituted —(C0-C12 alkyl)-heterocycloalkyl; and wherein $R^{10}$ is selected from hydrogen, halo, cyano, amino, hydroxyl, —$CH_2OH$, —$CH_2OAc$, —$CH_2NH_2$, —$CH_2X$, —C(O)H, —C(O)$NR^{21a}R^{21b}$, —C(O)$OR^{20}$, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alky-cycloalkyl, and optionally substituted —(C0-C12 alkyl)-heterocycloalkyl; wherein X is halogen; wherein $R^2$ is selected from hydrogen and C1-C6 alkyl; wherein each of $R^{21a}$ and $R^{21b}$ is selected from hydrogen and C1-C6 alkyl; or a pharmaceutically acceptable salt thereof.

Also disclosed are methods of preparing the disclosed compounds.

Also disclosed are pharmaceutical compositions comprising a therapeutically effective amount of one or more disclosed compounds, or pharmaceutically acceptable salt thereof, and a pharmaceutically acceptable carrier.

Also disclosed are methods for the treatment of pain in a mammal comprising the step of administering to the mammal a therapeutically effective amount of at least one disclosed compound or pharmaceutically acceptable salt thereof.

Also disclosed are uses of a disclosed compound, or a pharmaceutically acceptable salt thereof; a disclosed product of making, or a pharmaceutically acceptable salt thereof; or a disclosed pharmaceutical composition.

Also disclosed are uses of a disclosed compound, or a pharmaceutically acceptable salt thereof, in the manufacture of a medicament for the treatment of pain.

Also disclosed are kits comprising at least one disclosed compound, or a pharmaceutically acceptable salt, hydrate, solvate, or polymorph thereof, and one or more of: (a) at least one agent known to increase pain; (b) at least one agent known to decrease pain; (d) instructions for treating pain; or (f) instructions for administering the compound in connection with a clinical procedure associated with pain.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE FIGURES

The accompanying figures, which are incorporated in and constitute a part of this specification, illustrate several aspects and together with the description serve to explain the principles of the disclosure.

FIG. 2A shows structural aspects of a generic THC analog versus an ax-CBN analog. FIG. 2B shows structural aspects of THC versus CBN versus ax-CBN. FIG. 2C shows a calculated structure of a representative ax-CBN analog. FIG. 2D shows that ax-CBNs are three-dimensional in their ground state and planar in their transition state, which is opposite to natural CBN. FIG. 2E shows ground state three-dimensionality of THC versus CBN versus ax-CBN versus ax-CBN analogs (top) and transition state analysis for an ax-CBN analog represented by structure 14. FIG. 2F shows a plot of thermodynamic parameters (i.e., ln(k/T) versus 1/T) for the barrier to rotation for an ax-CBN analog.

FIG. 5A shows a scheme for an operationally simple, concise, and scalable route to synthesize ax-CBN. FIG. 5B shows a generalized disclosed synthetic scheme for expansion of the scope of the scheme shown in FIG. 5A.

FIG. 6A shows a convergent synthesis of ax-CBN. FIG. 6B shows a convergent synthesis of 9,10-dimethyl-ax-CBN. FIG. 6C shows a convergent synthesis of DMH-ax-CBN. FIG. 6D shows a convergent synthesis of 9,10-dimethyl-DMH-ax-CBN.

FIG. 8A shows a disclosed convergent synthesis route from lactone 7.1 via the use of 8-aminoquinoline directed C—H functionalization. FIG. 8B shows representative compounds prepared by the synthesis route shown in FIG. 8A.

FIG. 27A shows a plot of stimulus intensity versus dose in mg/kg of body weight, while

FIG. 28 shows background data from the scientific literature, i.e., a drug discrimination assay that can be used to assess the disclosed compounds. In a sample assay, rimonabant (square, 0.32 mg/kg; triangle, 1 mg/kg) antagonizes the dose effect of THC, compared to vehicle (circle) in mice trained to discriminate 10 mg/kg THC.

Figure 1A:
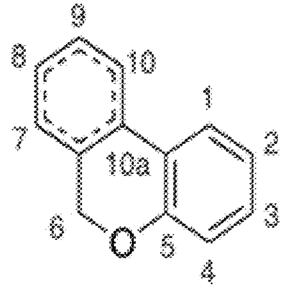
FIG. 1A shows the accepted benzopyran number system.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used herein, the term "and/or" includes any and all combinations of one or more of the associated listed items. Expressions such as "at least one of," when preceding a list of elements, modify the entire list of elements and do not modify the individual elements of the list.

As used in the specification and the appended claims, the singular forms "a," "an" and "the" include plural referents unless the context clearly dictates otherwise. Thus, for example, reference to "a THC analog," "an axially-chiral cannabinoid," or "a cannabinoid receptor ligand," includes, but is not limited to, two or more such THC analogs, axially-chiral cannabinoids, or cannabinoid receptor ligands, and the like.

Reference to "a" chemical compound refers to one or more molecules of the chemical compound rather than being limited to a single molecule of the chemical compound. Furthermore, the one or more molecules may or may not be identical, so long as they fall under the category of the chemical compound. Thus, for example, "a" chemical compound is interpreted to include one or more molecules of the chemical, where the molecules may or may not be identical (e.g., different isotopic ratios, enantiomers, and the like).

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms “about,” “approximate,” “at or about,” and “substantially” can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is “about,” “approximate,” or “at or about” whether or not expressly stated to be such. It is understood that where “about,” “approximate,” or “at or about” is used before a quantitative value, the parameter also includes the specific quantitative value itself, unless specifically stated otherwise.

As used herein, the terms “optional” or “optionally” means that the subsequently described event or circumstance can or cannot occur, and that the description includes instances where said event or circumstance occurs and instances where it does not.

As used herein, “administering” can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term “parenteral” can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, “therapeutic agent” can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians’ Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term “therapeutic agent” includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, “kit” means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, “instruction(s)” means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as pain. The effect can be therapeutic in terms of a partial or complete cure of a disease, condition, symptom or adverse effect attributed to the disease, disorder, or condition. The term "treatment" as used herein can include any treatment of a clinical condition, disease, or disorder using a disclosed axially-chiral cannabinol in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C1 to C6 alkyl esters and C5 to C7 cycloalkyl esters, although C1 to C4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C1 to C6 alkyl amines and secondary C1 to C6 dialkyl amines. In the case of secondary amines, the amine can also be in the form of a 5- or 6-membered heterocycle containing one nitrogen atom. Amides derived from ammonia, C1 to C3 alkyl primary amides and C1 to C2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambrdgesoft Corporation, U.S.A.).

It is understood, that unless otherwise specified, temperatures referred to herein are based on atmospheric pressure (i.e. one atmosphere).

Described herein are axially-chiral cannabinols that have therapeutic or clinical utility. Also described herein are methods of synthesizing the disclosed axially-chiral cannabinols. Also described herein are methods of administering the disclosed axially-chiral cannabinols to a subject in need thereof. In some aspects, the subject can have a pain disorder or condition. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "aliphatic" or"aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or"haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term 'alkanediyl' as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, $—CH_2—$ (methylene), $—CH_2CH_2—$, $—CH_2C(CH_3)_2CH_2—$, and $—CH_2CH_2CH_2—$ are non-limiting examples of alkanediyl groups.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1$-$OA^2$ or $—OA^1$-$(OA^2$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a shorthand notation for a carbonyl group, i.e., C═O.

The terms "amine" or"amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula —NH(-alkyl) and $—N(\text{-alkyl})_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyrdazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle" as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR—$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, $-(haloR^\bullet)$, $—(CH_2)_{0-2}OH$, $—(CH_2)_{0-2}OR^\bullet$, $—(CH_2)_{0-2}CH(OR^\bullet)_2$; $—O(haloR^\bullet)$, —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, $═NNR^*_2$, $═NNHC(O)R^*$, $═NNHC(O)OR^*$, $═NNHS(O)_2R^*$, $═NR^*$, $═NOR^*$, $—O(C(R^*_2))_2O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, $-(haloR^\bullet)$, —OH, $—OR^\bullet$, $—O(haloR^\bullet)$, —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by"halo" is substituted only with one or more halogens, and is independently $C_{1-4}$ aliphatic, $—CH_2Ph$, $—O(CH_2)_{0-1}Ph$, or a 5-n-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —C(O)$R^{\dagger}$, —C(O)O$R^{\dagger}$, —C(O)C(O)$R^{\dagger}$, —C(O)$CH_2$C(O)$R^{\dagger}$, —$S(O)_2R^{\dagger}$, —$S(O)_2NR^{\dagger}_2$, —C(S)$NR^{\dagger}_2$, —C(NH)$NR^{\dagger}_2$, or —N($R^{\dagger}$)$S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —O$R^{\bullet}$, —O(halo$R^{\bullet}$), —CN, —C(O)OH, —C(O)O$R^{\bullet}$, —$NH_2$, —NH$R^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2$Ph, —O$(CH_2)_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

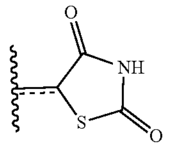

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

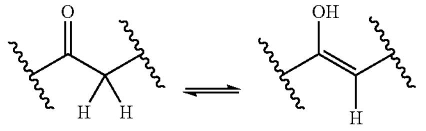

keto form enol form

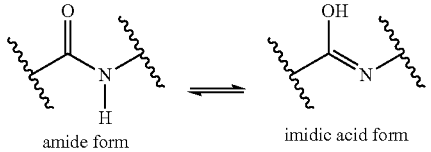

amide form imidic acid form

Likewise, amides with an N-hydrogen can exist in an equilibrium of the amide form and the imidic acid form. Unless stated to the contrary, the disclosure includes all such possible tautomers.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

In some aspects, a structure of a compound can be represented by a formula:

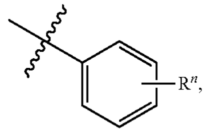

which is understood to be equivalent to a formula:

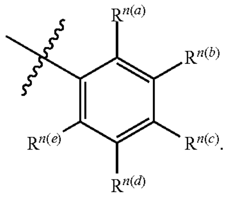

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Cannabinoid Biology

Opioid overdose is the leading cause of unintentional drug-related deaths in the U.S. Several studies suggest that decreased prescription opioid use and overdose deaths may be linked to medical marijuana legalization. In response to the opioid epidemic and growing support for the medicinal value of cannabis, phytocannabinoids (e.g. (−)-trans-A-tetrahydrocannabinol (THC)) and phytocannabinoid analogs remain viable candidate analgesic medications. Generally speaking, cannabinoids are attractive treatments for a variety of central nervous systems disorders. THC produces its effects, both therapeutic and recreational, by interaction with the cannabinoid $CB_1$ and $CB_2$ G-protein-coupled receptors. Recent discoveries also show that cannabinoids act on a variety of other GPCRs, too. Dibenzopyran numbering used throughout the specification and claims is shown in FIG. 1A.

A more thorough analysis of three-dimensional cannabinoid chemical space enabled by novel synthetic chemistry approaches could foster much-needed breakthroughs in the development of new cannabinoid-inspired therapeutics. In this regard, without wishing to be bound by a particular theory, it is believed that axially-chiral cannabinols (ax-CBNs) can allow for conceptually novel approaches to cannabinoid-inspired drug discovery, including analgesic development. First, ax-CBNs will have three-dimensionality akin to THC, but are biaryl. Moreover, they can exhibit restricted/biased biaryl conformations that can prevent ax-CBNs from occupying their planar state engendering three-dimensionality in their ground state. Second, because ax-CBNs are biaryl, they can have increased bench stability/shelf-life compared to THC, which is sensitive to aerobic and metabolic oxidation. Finally, because ax-CBNs are can be prepared via the development of new chemical methods/strategies, they are an untapped chemical space for accessing cannabinoid-inspired drug candidates with potential as ligands for cannabinoid receptors, and as such, potential for positive clinical intervention for a myriad of CNS disorders including, but not limited to, pain, weight management, nausea, and epilepsy. The data herein supports that ax-CBNs are accessible with the hypothesized physical properties (shape and stability) and that they bear analgesic properties.

Described here are axially-chiral cannabinols (ax-CBNs) and three-dimensional cannabinoid architectures, as attractive new scaffolds for cannabinoid-inspired drug discovery, including analgesic drug development. In this regard, it is believed, without wishing to be bound by a particular theory, that ax-CBNs will can provide unique opportunities due to the three-dimensionality and structural stability imparted by the conformationally restricted biaryl motif.

Figure 1B:
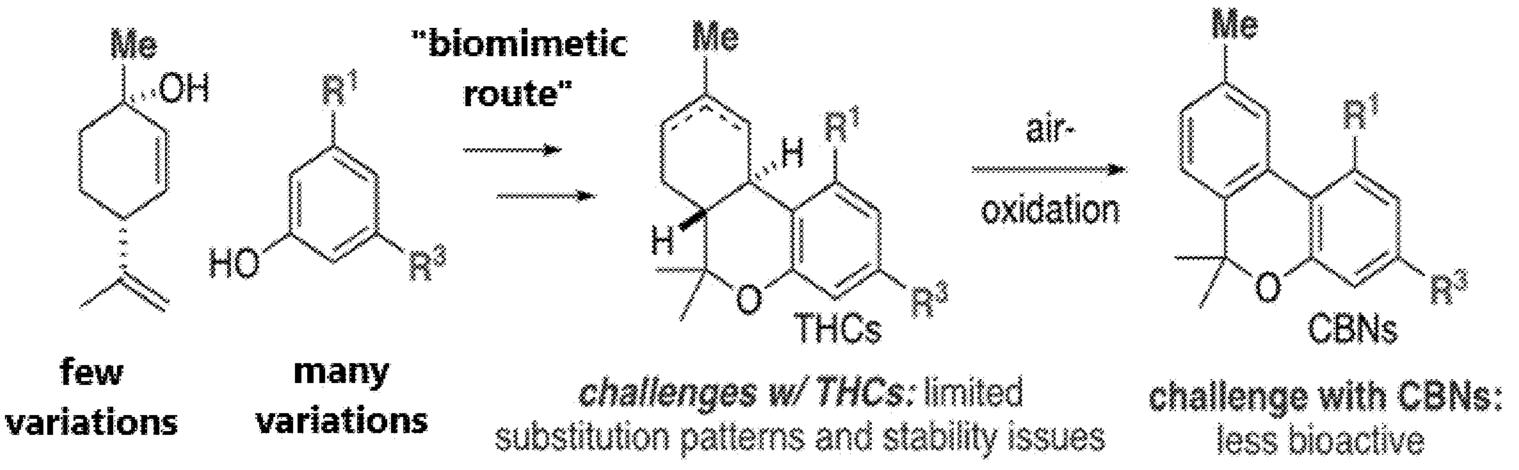
FIG. 1B shows a conventional biomimetic route to cannabinoids that is exclusively used for preparing cannabinoid analogs; however, this route presents several challenges for preparation of diverse cannabinoid analogs.

Cannabinoid receptor ligands hold promise as remedies for a myriad of CNS disorders including pain, weight management, nausea, and epilepsy. In particular, the current opioid crisis has fueled renewed focus on non-opioid analgesics, including cannabinoid receptor ligands, to be administered alone or in combination with other pain medications including opioids, to provide effective, safe pain relief, thereby mitigating the adverse effects of opioids including death. Since the discovery of (−)-trans-$\Delta^9$-tetrahydrocannabinol (THC) by Mechoulam and colleagues in the 1960s, THC-based analog development has been dominated by one general method, the "biomimetic route," (FIG. 1B) where a cyclic monoterpene derivative and a phenolic component serve as starting materials. Though effective for certain core substitution patterns, other patterns are inaccessible with this established method, thereby limiting insights into structure-activity relationships and clinical development of cannabinoid receptor ligands. These longstanding approaches to creating cannabinoid architectures, while still promising, have not unlocked the full potential of THC-based drug development. A more thorough analysis of cannabinoid chemical space enabled by novel synthetic chemistry approaches could foster much-needed breakthroughs in the development of new THC-inspired therapeutics.

Drug discovery at $CB_1$ and $CB_2$ receptors remains an underexploited opportunity to develop novel therapeutics for a variety of disorders including pain, immune function, spasticity, nausea, weight loss/gain, neurodegenerative disorders, anxiety, depression, and substance use disorders. $CB_1$ receptors, which are the most abundant G protein-coupled receptor type in the CNS, are implicated in most of these diseases, whereas $CB_2$ receptors are primarily implicated in pain, immune function, and neuroinflammation. Different strategies are being developed to selectively activate subsets of CB receptors or different signaling pathways emanating from CB receptors. This includes ligands that vary in efficacy (i.e., agonists, neutral antagonists, and inverse agonists) and binding affinity (i.e., selectivity) for $CB_1$ versus $CB_2$ receptors. Ligands that do not readily cross the blood-brain-barrier, so-called peripherally selective, are being developed to avoid CNS actions while impacting diseases mediated by peripheral CB receptors (i.e., neuropathic pain). Multiple different sites on the same G protein-coupled receptor complex also provide numerous drug targets. Many of the plant-derived and endogenous cannabinoid ligands bind to the orthosteric site of CB receptors; other sites (i.e., allosteric sites) can be targeted by drugs to either modify the affinity or efficacy of orthosteric ligands (i.e., allosteric modulators), or directly impact signaling independent of orthosteric actions. Biased signaling is yet another potential avenue for developing novel therapeutics with unique properties. CB receptors preferentially couple to $G_{i/o}$-type G proteins, thereby inhibiting adenylyl cyclase and cyclic adenosine monophosphate. G protein-dependent mechanisms include activation of mitogen-activated protein kinases, as well as positive and negative coupling to a variety of calcium and potassium channels. While many CB receptor ligands interact with $G_{i/o}$-type G protein pathways, other ligands may signal preferentially through $G_s$ and $G_q$ G proteins, or through pathways independent of G proteins such as β-arrestin. Although relationships between the various CB receptor signaling pathways and function have yet to be fully established, this richness has generated considerable enthusiasm for developing ligands that differentially impact these pathways and the specific diseases to which they are linked.

Disclosed herein are new synthesis platforms for cannabinoid-inspired drug discovery that can provide compounds that further validate bioactivity at cannabinoid receptors. Numerous challenges to increasing the diversity of chemical space for cannabinoid compounds exist. First, most phytocannabinoid analogs are prepared by one method. This renders certain substitution patterns and diversification unobtainable. Cannabinoid synthesis is most commonly achieved by variation of the "classic"/"biomimetic route," (FIG. 1B) where a cyclic monoterpene derivative and a phenolic component serve as starting materials. Thus, due to the abundance of phenols, the majority of analogs prepared to date are diversified in the benzenoid-portion of the scaffold. There are modern total synthesis approaches that are also being developed, but few studies have yielded testable analogs. Second, tetrahydrocannabinols have limited stability, which limits shelf-life and drug discovery. Tetrahydrocannabinols and analogs (THCs) are unstable and tend to isomerize and oxidize, ultimately ending up at the planar cannabinol state (CBNs). Third, cannabinols (CBNs), in limited studies, tend to be less bioactive than their more studied parent tetrahydrocannabinol variants (THCs). In direct comparison, in a variety of studies, THC is consistently measured to have low nanomolar (20-40 nM) binding affinity for cannabinoid receptors whereas CBN is always significantly higher. Furthermore, THC has been examined in many studies (in vivo, in vitro, and clinical), CBN has not been examined nearly as intensely; there is only a handful of papers that the authors are aware of that examine CBN and its analogs. The synthesis methods disclosed herein provide methods for the facile synthesis of axially-chiral cannabinoids that can address challenges noted herein above and represent a new opportunity for cannabinoid-inspired drug discovery.

Compounds

Disclosed herein are compounds having a structure represented by a formula:

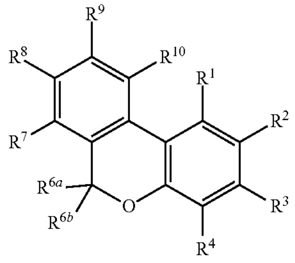

wherein $R^1$ is selected from hydrogen, halo, cyano, amino, hydroxyl, methoxy, acetoxy, —$OC_6H_5$, and —$OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alky-heterocycloalkyl; wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alky-heteroaryl, optionally substituted —(C0-C12 alky-cycloalkyl, and optionally substituted —(C0-C12 alky-heterocycloalkyl; and wherein $R^{10}$ is selected from hydrogen, halo, cyano, amino, hydroxyl, —$CH_2OH$, —$CH_2OAc$, —$CH_2NH_2$, —$CH_2X$, —C(O)H, —C(O)$NR^{21a}R^{21b}$, —C(O)$OR^{20}$, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alky-cycloalkyl, and optionally substituted —(C0-C12 alky-heterocycloalkyl; wherein X is halogen; wherein $R^{20}$ is selected from hydrogen and C1-C6 alkyl; wherein each of $R^{21a}$ and $R^{21b}$ is selected from hydrogen and C1-C6 alkyl; or a pharmaceutically acceptable salt thereof.

In some aspects, disclosed herein are compounds represented by a structure having a formula:

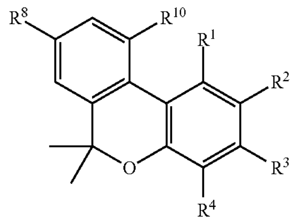

wherein substituents ($R^1$, $R^2$, and so forth, as applicable) are described as above.

In some aspects, disclosed herein are compounds represented by a structure having a formula:

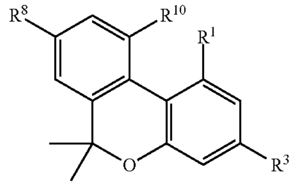

wherein substituents ($R^1$, $R^2$, and so forth, as applicable) are described as above.

In some aspects, disclosed herein are compounds represented by a structure having a formula:

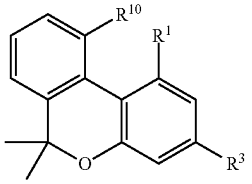

wherein substituents ($R^1$, $R^2$, and so forth, as applicable) are described as above.

In some aspects, disclosed herein are compounds represented by a structure having a formula:

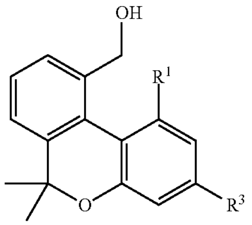

wherein substituents ($R^1$, $R^2$, and so forth, as applicable) are described as above.

In some aspects, disclosed herein are compounds represented by a structure having a formula:

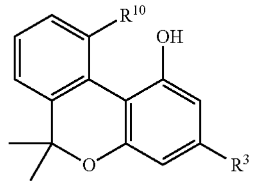

wherein substituents ($R^1$, $R^2$, and so forth, as applicable) are described as above.

In some aspects, disclosed herein are compounds represented by a structure having a formula:

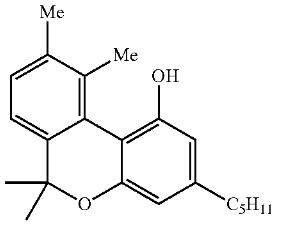

In some aspects, disclosed herein are compounds represented by a structure having a formula:

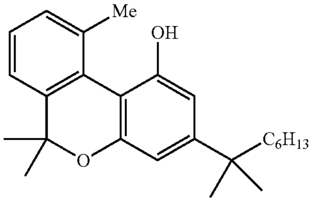

In some aspects, disclosed herein are compounds represented by a structure having a formula:

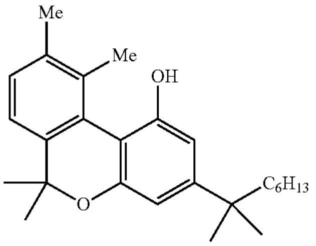

In one aspect, disclosed herein are axially chiral cannabinoid analogs having a biaryl structure but lacking a pyran ring. In a further aspect, bulky substituents on the biaryl structures prevent free rotation about the carbon-carbon bond linking the two aryl groups.

In some aspects, disclosed herein are compounds represented by a structure having a formula:

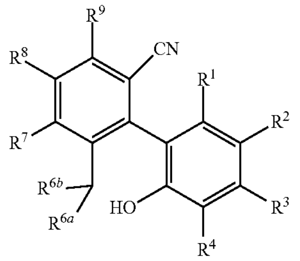

In some aspects, disclosed herein are compounds represented by a structure having a formula:

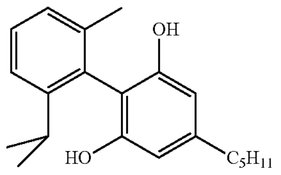

In various aspects, it is contemplated herein that the disclosed compounds further comprise their bioisosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York. 1970, 64-80; (ii) Burger, A.: "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thomber C W. "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Methods of Making the Compounds

In one aspect, the disclosure relates to methods of making compounds useful for controlling pain, inflammation, and related conditions, which can be useful in the treatment of cancer patients, post-surgical patients, patients with allergies and autoimmune diseases, and the like. In one aspect, the disclosure relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the disclosure comprises a pharmaceutical composition comprising a therapeutically effective amount of the product of the disclosed methods and a pharmaceutically acceptable carrier. In a still further aspect, the disclosure comprises a method for manufacturing a medicament comprising combining at least one product of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the disclosure might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

Disclosed herein are methods of synthesizing an axially chiral cannabinol analog. In some aspects, the disclosed methods can comprise preparing a substituted ((alkynyl)oxy)benzaldehyde analog, the method comprising: reacting in the presence of a base and a metal salt a substituted chloroalkyne analog having a structure represented by a formula I:

I

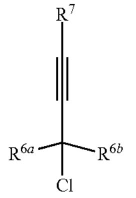

substituted 2-hydroxybenzaldehyde analog having a structure represented by a formula II:

II

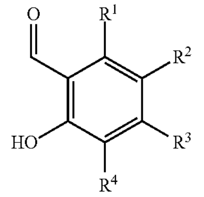

thereby providing a substituted ((alkynyl)oxy)benzaldehyde analog having a structure represented by a formula III:

III

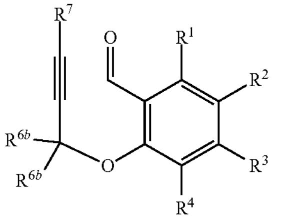

wherein $R^1$ is selected from hydrogen, halo, cyano, amino, hydroxyl, methoxy, acetoxy, —$OC_6H_5$, and —$OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alkyl)-heterocycloalkyl; and wherein $R^7$ is selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alky-cycloalkyl, and optionally substituted —(C0-C12 alkyl-heterocycloalkyl.

In some aspects, the disclosed methods can comprise preparing a substituted ((alkynyl)oxy)benzylidene)alkenylnitrile analog, the method comprising: reacting in the presence of a tertiary amine and a Lewis acid a substituted ((alkynyl)oxy)benzaldehyde analog having a structure represented by a formula III:

III

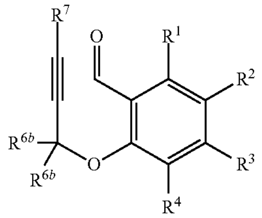

with a substituted alkenyl nitrile analog having a structure represented by a formula IV:

IV

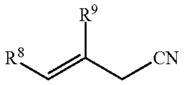

thereby providing the substituted ((alkynyl)oxy)benzylidene)alkenylnitrile analog having a structure represented by a formula V:

V

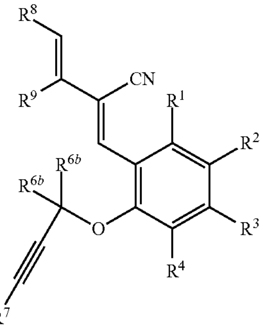

wherein $R^1$ is selected from hydrogen, halo, cyano, amino, hydroxyl, methoxy, acetoxy, —$OC_6H_5$, and —$OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; and wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl.

In some aspects, the disclosed methods can comprise preparing a substituted 8,10a-dihydro-6H-benzo[c]chromene-10-carbonitrile analog, the method comprising:

carrying out a Diels-Alder cyclization of a compound having a structure represented by a formula V:

V

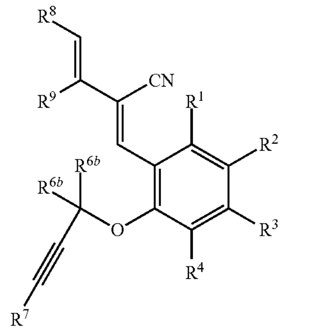

thereby providing the substituted 8,10a-dihydro-6H-benzo[c]chromene-10-carbonitrile analog having a structure represented by a formula VI:

VI

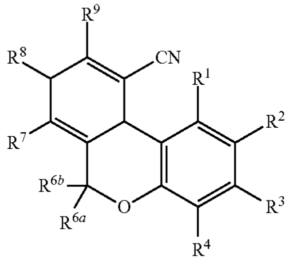

wherein $R^1$ is selected from hydrogen, halo, cyano, amino, hydroxyl, methoxy, acetoxy, —$OC_6H_5$, and —$OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; and wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl.

In some aspects, the disclosed methods can comprise preparing a substituted 6H-benzo[c]chromene-10-carbonitrile analog, the method comprising: reacting a dehydration agent with a substituted 8,10a-dihydro-6H-benzo[c]chromene-10-carbonitrile analog having a structure represented by a formula VI:

VI

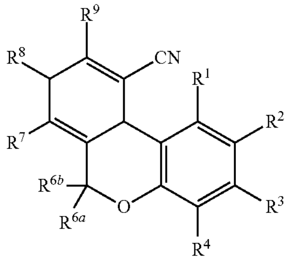

thereby providing the substituted 6H-benzo[c]chromene-10-carbonitrile analog having a structure represented by a formula VII:

VII

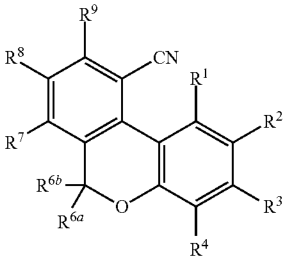

wherein $R^1$ is selected from hydrogen, halo, cyano, amino, hydroxyl, methoxy, acetoxy, —$OC_6H_5$, and —$OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; and wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl.

In one aspect, the base in step (a) can be 1,8-diazabicyclo(5.4.0)undec-7-ene (DBU), 1,5-diazabicyclo(4.3.0)non-5-ene (DBN), 1,4-diazabicyclo[2.2.2]octane, or a combination thereof. In another aspect, the metal salt in step (a) can be $CuCl_2$, $Cu_3(NO_3)_2$, $CuSO_4$, a combination thereof, or a hydrate thereof.

In a further aspect, the tertiary amine in step (b) can be N,N,N',N'-tetraethyl-1,3-propanediamine, N,N,N',N'-tetraethyl-1,3-butanediamine, N,N,N',N'-tetraethyl-1,3-hexanediamine, or a combination thereof. In a still further aspect, the Lewis acid in step (b) can be $TiCl_4$ or $SnCl_4$.

In one aspect, the Diels-Alder cyclization of step (c) can be performed at a temperature of from about 30° C. to about 150° C., or at about 30, 40, 50, 60, 70, 80, 90, 100, 110, 120, 130, 140, or about 150° C., or a combination of any of the foregoing values, or a range encompassing any of the foregoing values. In one aspect, the Diels-Alder cyclization is performed at about 110° C.

In another aspect, the dehydrogenation agent of step (d) can be a quinone such as, for example, 2,3-dichloro-5,6-dicyano-1,4-benzoquinone (DDQ).

In one aspect, when $R^1$ is methoxy, the method disclosed herein can further include: (e) reacting the product of formula VII with a nucleophile to produce a product of formula VIII:

VIII

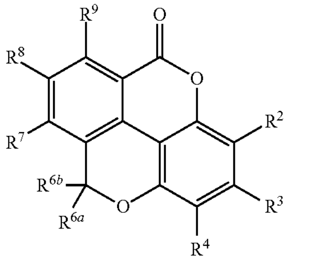

In one aspect, the nucleophile can be the ethanethiolate anion and can be present in the reaction vessel as sodium ethanethiolate (NaSEt).

In another aspect, the method disclosed herein can further include: (f) reacting the product of formula Viii with a reducing agent to produce a product of formula IX:

IX

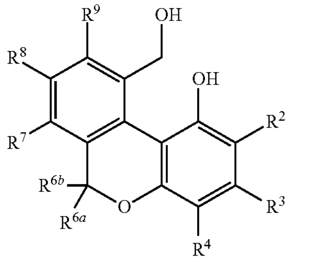

In one aspect, the reducing agent can be $LiAlH_4$, $NaBH_4$, NaH, LiH, $CaH_2$, or a combination thereof. In a further aspect, the reducing agent is $LiAlH_4$.

In an alternative aspect, following production of a product of formula VII after step (d), the method can include: (g) reacting the product of formula VII with a nucleophile to produce a product of formula X:

X

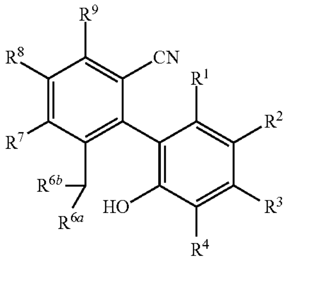

In one aspect, the nucleophile can be the ethanethiolate anion and can be present in the reaction vessel as sodium ethanethiolate (NaSEt).

Non-limiting general and exemplary schemes for preparing the disclosed compounds are presented below. Any substituent (e.g., $R^1$, $R^{6a}$, —CN, —OH, etc.) can be post-synthetically modified by methods known in the art. Exemplary and non-limiting methods for post-synthetic modification are presented in FIG. 4, FIGS. 8A-8B, and FIGS. 9A-9C.

Synthesis Route 1

In one aspect, a useful intermediate for the preparation of substituted axially-chiral cannabinol analogs of the present disclosure can be prepared generically by the synthesis scheme as shown below. All positions are defined herein.

Scheme 1A

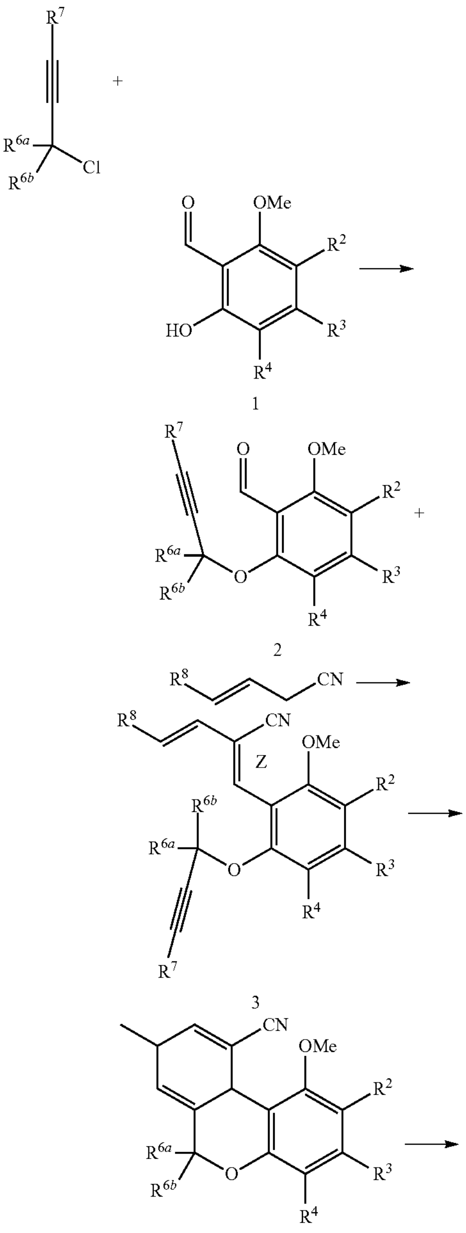

1

2

3

4

-continued

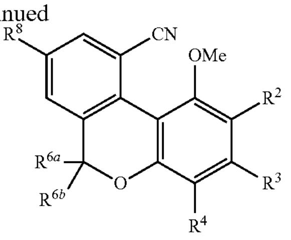

5

Compounds are represented in generic form, with substituents as noted in compound descriptions elsewhere herein. A more specific example is set forth below.

Scheme 1B

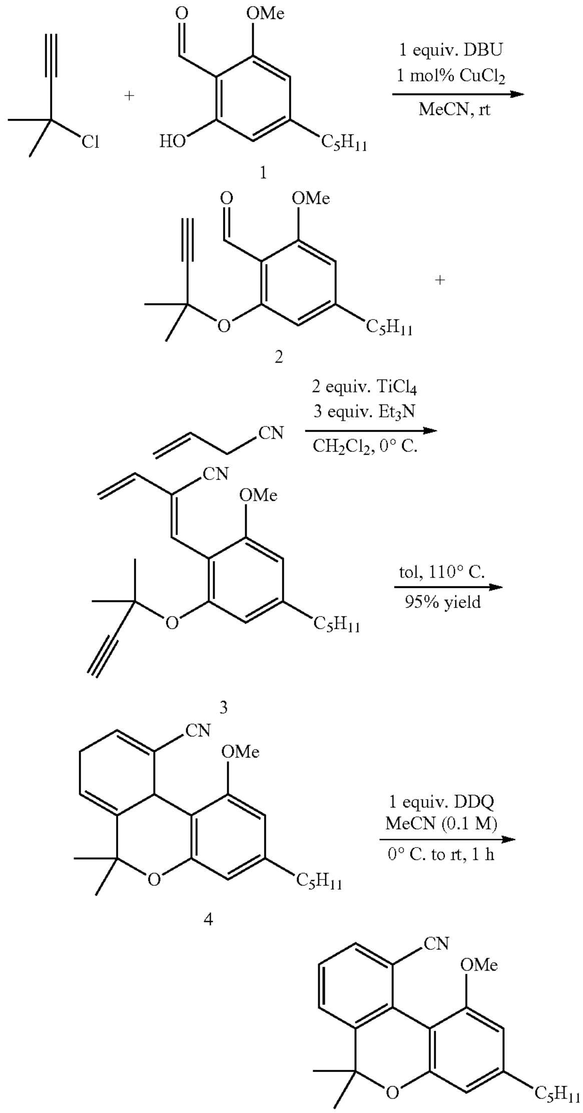

5

In one aspect, a useful intermediate for the preparation of substituted axially-chiral cannabinol analogs of the present disclosure can be prepared generically by the synthesis scheme as shown below by modification of the cyano and/or methoxy groups, e.g., as shown in the general structure above or in specifically in compound 5 above. All positions are defined herein.

Synthesis Route 2

In one aspect, a substituted axially-chiral cannabinol analogs of the present disclosure can be prepared generically by the synthesis scheme as shown below. All positions are defined herein.

Scheme 2A

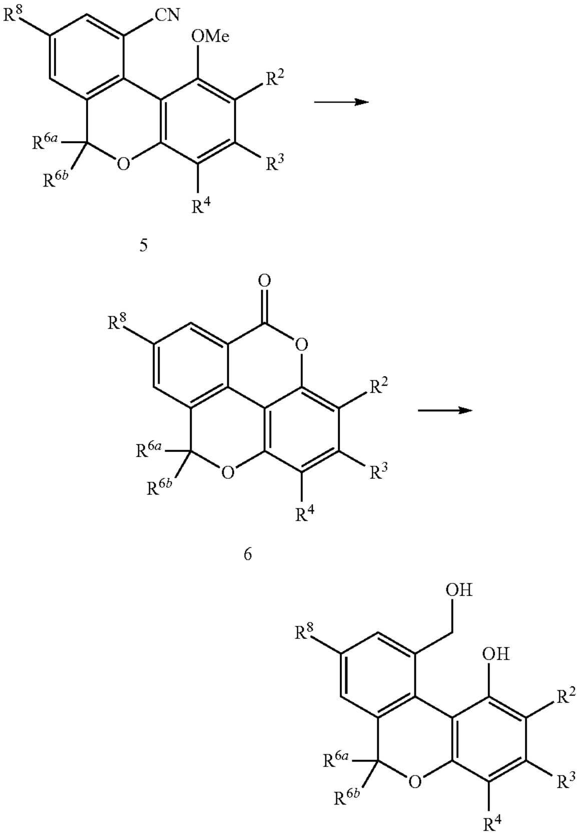

(±)-ax-CBN

Compounds are represented in generic form, with substituents as noted in compound descriptions elsewhere herein. A more specific example is set forth below.

Scheme 2B

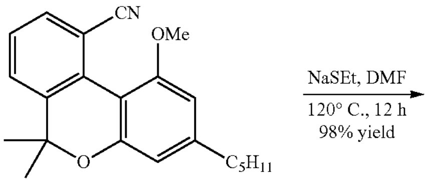

5

-continued

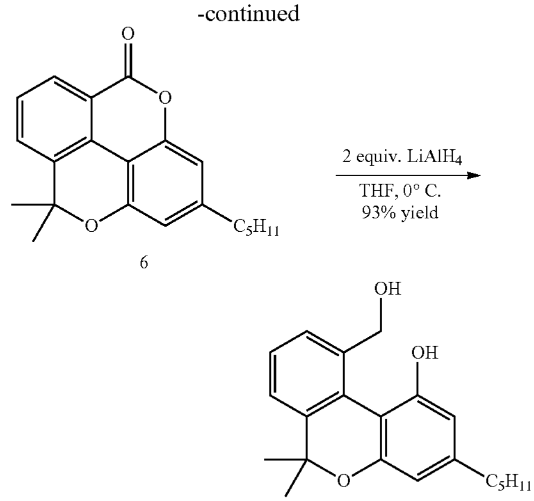

6

(±)-ax-CBN

Scheme 2C

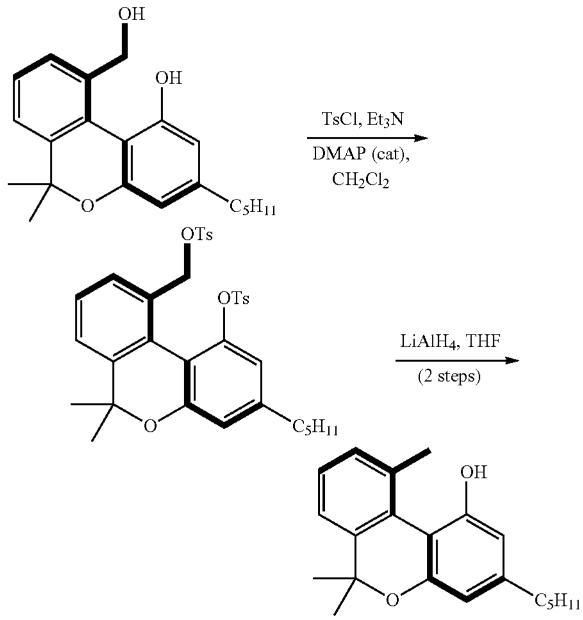

In some aspects, when a (±)-ax-CBN is the final product of a reaction as disclosed above, the reaction shown in Scheme 2C, or any other reaction known in the literature, can be performed in order to change substituents as desired to achieve different solubilities, substituent polarity, activity for a biological target, and other properties.

Synthesis Route 3

In some aspects, the disclosed schemes, reactions, and conditions outlined above can generally proceed in a modular manner using analogous starting materials in order to achieve different substituents on the benzopyran ring structure. An exemplary generalized scheme is presented below.

Scheme 3A

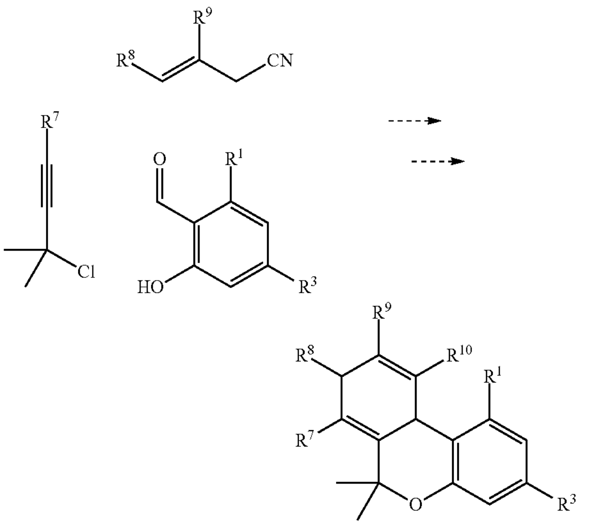

A specific example of the process in Scheme 3A is presented below:

Scheme 3B

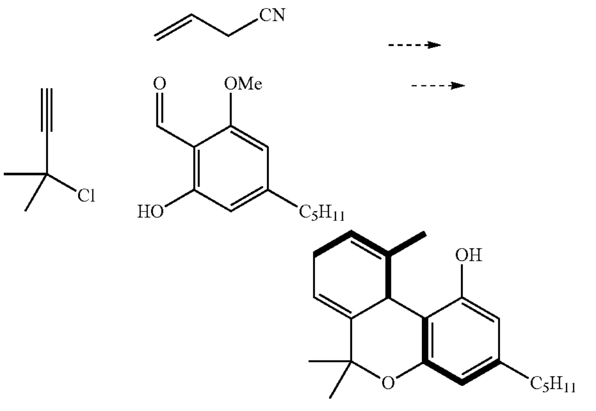

Synthesis Route 3

In some aspects, a reaction intermediate from Scheme 2B can be isolated and modified by the procedure shown in Scheme 4 or any other procedure known in the art in order to prepare analogs as disclosed herein with different substituents in the 9 position on the benzopyran ring system as shown below.

Scheme 4

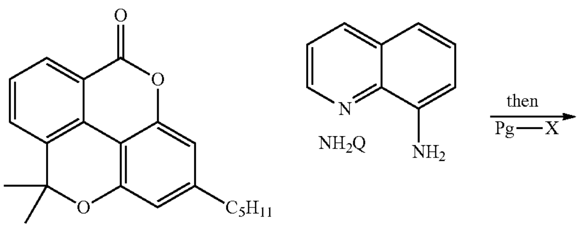

-continued

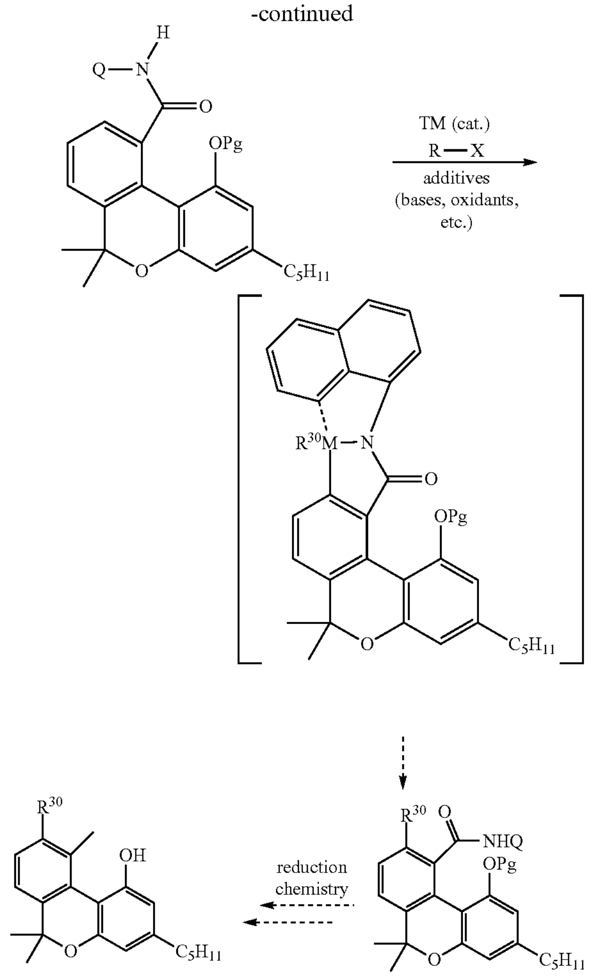

where $R^{30}$ can be any desired substituent including methyl (forming 9,10-dimethyl-ax-CBN), hydroxyl (forming 9-OH-10-methyl-ax-CBN), trifluoromethyl (forming 9-$CF_3$-10-methyl-ax-CBN), fluoro (9-F-10-methyl-ax-CBN), iodo (forming 9-I-10-methyl-ax-CBN), an aromatic group (forming 9-Ar-10-methyl-ax-CBN, where Ar can be a substituted or unsubstituted aromatic or heteroaromatic group as described previously), or the like. Example non-limiting structures are presented in FIG. 8B.

Synthesis Route 5

In some aspects, a reaction intermediate or starting material from Scheme 2A or 2B can be isolated and modified by the procedure shown in Scheme 5 or any other procedure known in the art in order to prepare biaryl analogs lacking the pyran ring seen in cannabinols but retaining restricted rotation and three-dimensionality as shown below.

Scheme 5

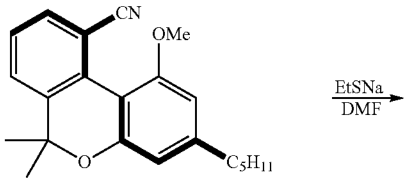

-continued

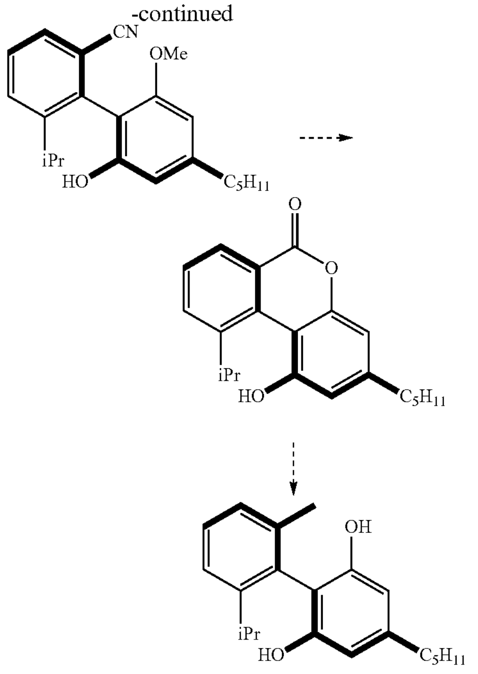

where other possible substituents on the biaryl ring system are not shown for purposes of clarity; however, any analogous substituents for $R^1$, $R^2$, $R^3$, $R^7$, $R^8$, $R^9$, and $R^{10}$ compatible with the disclosed chemistry and discussed previously are possible on the biaryl ring system shown in Scheme 5, wherein numbering ($R^1$, $R^2$, etc.) is analogous to the benzopyran substituent numbering used throughout this disclosure.

Synthesis Route 6

In some aspects, a reaction product from Scheme 2B can be isolated and modified by the procedure shown in Scheme 6 or any other procedure known in the art in order to prepare analogs as disclosed herein with additional carbon-carbon bonds, where $R^{31}$ can be any substituent, radical, or residue described above that is compatible with the disclosed reactions as shown below.

Scheme 6

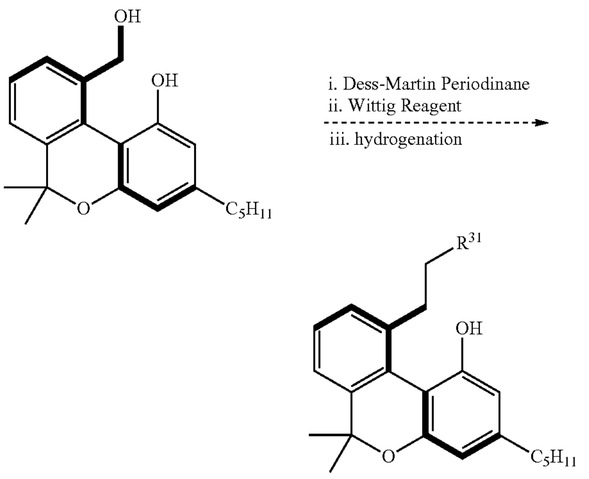

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, “pharmaceutically-acceptable carriers” means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, “parenteral administration” includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherifled with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherifled, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyttartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulfoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

The disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-s-cyclodextrin or sulfobutyl-s-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidyicholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringers dextrose, dextrose and sodium chloride, lactated Ringers and fixed oils. Intravenous vehicles include fluid and nutrient replenishers, electrolyte replenishers such as those based on Ringers dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the 'Bag-in-a-can' formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of modulation of cannabinoid receptor, $CB_1$ and/or $CB_2$, activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating cannabinoid receptor, $CB_1$ and/or $CB_2$, activity (e.g., treatment of one or more disorders as described herein below) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and an additional therapeutic agent, e.g., a therapeutic agent that is anti-inflammatory or can treat acute or chronic pain. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds

In a further aspect, the present disclosure provides methods of treatment comprising administration of a therapeutically effective amount of a disclosed axially-chiral cannabinol compound or pharmaceutical composition as disclosed herein above to a subject in need thereof.

In some aspects, the method of treatment is a method of treatment of diseases, conditions, syndromes, disorders, and other forms of illness in which modulation of a cannabinoid receptors, $CB_1$ and/or $CB_2$, can provide a therapeutic benefit. For example, as explained above, patients suffering from illnesses, such as cancer and AIDS, often experience symptoms, such as lack of appetite, which can be relieved with the method of the present disclosure. Patients suffering from neuropathy experience chronic pain and other symptoms which can be relieved with the method of the present disclosure. Patients suffering from multiple sclerosis or spinal cord injury experience spasticity and other symptoms that can be relieved with the method of the present disclosure. The methods of the present disclosure can also be used to relieve symptoms associated with dystonia and malignant tumors. The methods of the present disclosure can also be used to relieve symptoms of stroke, head injuries, neurodegenerative disorders, and other conditions, diseases, and disorders associated with the N-methyl-D-aspartate receptor. Still other diseases and disorders that the present disclosure may prove useful in treating include Huntington's disease, arthritis, nervous-tissue inflammation, vascular inflammation, inflammatory bowel disease, and other inflammation-related conditions. The mechanism by which symptoms are relieved is not particularly critical to the practice of the present disclosure. Illustratively, symptoms can be relieved by directly treating the underlying illness or by blocking the biological pathways by which the illness produces the symptoms.

Moreover, the methods of treatment of the present disclosure can be used to relieve discomfort associated with the treatment of illness. Illustratively, the method of the present disclosure can be used to relieve nausea, vomiting, and/or other discomforts associated with chemotherapy and other treatment regimens used to treat cancer and other illnesses.

In further aspects, the disclosed axially-chiral cannabinol compounds can be used to treat arthritis, a nervous-tissue inflammation, vascular inflammation, inflammatory bowel disease, and other inflammation-related conditions.

"Relieve," as used herein, is meant to include complete elimination as well as any clinically or quantitatively measurable reduction in the subject's symptoms and/or discomfort.

In some aspects, the subject treated is experiencing a loss of appetite, acute pain, chronic pain, spasticity, dystonia, and nausea and/or vomiting.

Kits

In a further aspect, the present disclosure relates to kits comprising at least one disclosed compound, or a pharmaceutically acceptable salt, hydrate, solvate, or polymorph thereof, and one or more of: (a) at least one agent known to increase pain; (b) at least one agent known to decrease pain; (d) instructions for treating pain; or (f) instructions for administering the compound in connection with a clinical procedure associated with pain.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In a further aspect, the disclosed kits can include at least one agent known to increase cannabinoid receptor activity; at least one agent known to decrease cannabinoid receptor activity; at least one agent known to treat Huntington's disease, arthritis, nervous tissue inflammation, vascular inflammation, inflammatory bowel disease, another inflammation-related condition; and combinations thereof.

It is contemplated that the disclosed kits can be used in connection with the disclosed methods of making, the disclosed methods of using or treating, and/or the disclosed compositions.

Research Tools

The disclosed compounds and pharmaceutical compositions have activity as modulators of cannabinoid receptors, CB1 and/or CB2. As such, the disclosed compounds are also useful as research tools. Accordingly, one aspect of the present disclosure relates to a method of using a compound of the disclosure as a research tool, the method comprising conducting a biological assay using a compound of the disclosure. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a compound of the disclosure to provide a second assay value; wherein step (a) is conducted either before, after or concurrently with step (b); and (c) comparing the first assay value from step (a) with the second assay value from step (b). Exemplary biological assays include a cannabinoid receptor assay that can be conducted in vitro or in a cell culture system. Still another aspect of the disclosure relates to a method of studying a biological system, e.g., a model animal for a clinical condition, or biological sample comprising a cannabinoid receptor, the method comprising: (a) contacting the biological system or sample with a compound of the disclosure; and (b) determining the effects caused by the compound on the biological system or sample.

The disclosed compounds and pharmaceutical compositions have activity as modulators of pain, either acute or chronic, in a subject. As such, the disclosed compounds are also useful as research tools. Accordingly, one aspect of the present disclosure relates to a method of using a compound of the disclosure as a research tool, the method comprising conducting a biological assay using a compound of the disclosure. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a compound of the disclosure to provide a second assay value; wherein step (a) is conducted either before, after or concurrently with step (b); and (c) comparing the first assay value from step (a) with the second assay value from step (b). An aspect of the disclosure relates to a method of studying a biological system, e.g., a model animal of pain, the method comprising: (a) contacting the biological system or sample with a compound of the disclosure; and (b) determining the effects caused by the compound on the biological system or sample.

Aspects

Aspect 1. A compound having a structure represented by a formula:

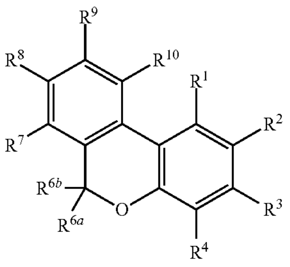

wherein $R^1$ is selected from hydrogen, halo, cyano, amino, hydroxyl, methoxy, acetoxy, $-OC_6H_5$, and $-OCH_2C_6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alky-cycloalkyl, and optionally substituted —(C0-C12 alky-heterocycloalkyl; wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alky-heteroaryl, optionally substituted —(C0-C12 alky-cycloalkyl, and optionally substituted —(C0-C12 alky-heterocycloalkyl; and wherein $R^{10}$ is selected from hydrogen, halo, cyano, amino, hydroxyl, —CH2OH, —CH2OAc, —CH2NH2, —CH2X, —C(O)H, —C(O)NR21aR21b, —C(O)OR20, optionally substituted alkyl, optionally substituted alkenyl, optionally substituted alkynyl, optionally substituted —(C0-12 alkyl)-aryl, optionally substituted —(C0-C12 alky-heteroaryl, optionally substituted —(C0-C12 alky-cycloalkyl, and optionally substituted —(C0-C12 alky-heterocycloalkyl, wherein X is halogen; wherein $R^{20}$ is selected from hydrogen and C1-C6 alkyl; wherein each of $R^{21a}$ and $R^{21b}$ is selected from hydrogen and C1-C6 alkyl; or a pharmaceutically acceptable salt thereof.

Aspect 2. The compound of Aspect 1, wherein $R^1$ is selected from hydroxyl, methoxy, and acetoxy.

Aspect 3. The compound of Aspect 1, wherein $R^1$ is selected from hydroxyl and methoxy.

Aspect 4. The compound of Aspect 1, wherein $R^1$ is hydroxyl.

Aspect 5. The compound of Aspect 1, wherein $R^3$ is selected from C1-C6 alkyl, —(C0-C12 alkyl)-phenyl, and phenyl.

Aspect 6. The compound of Aspect 1, wherein $R^3$ is selected from methyl, ethyl, propyl, isopropyl, tert-butyl, sec-butyl, isobutyl, neopentyl, isopentyl, sec-pentyl, and tert-pentyl.

Aspect 7. The compound of Aspect 1, wherein $R^3$ is pentyl.

Aspect 8. The compound of Aspect 1, wherein $R^{10}$ is selected from cyano, amino, $—CH_2OH$, $—CH_2OAc$, $—CH_2NH_2$, and $—CH_2Br$.

Aspect 9. The compound of Aspect 1, having a structure represented by a formula:

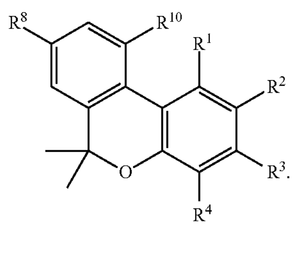

Aspect 10. The compound of Aspect 1, having a structure represented by a formula:

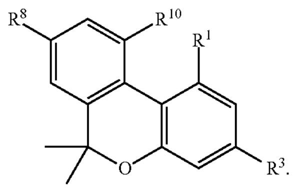

Aspect 11. The compound of Aspect 1, having a structure represented by a formula:

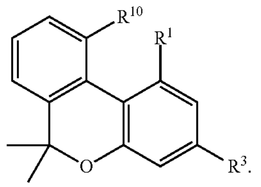

Aspect 12. The compound of Aspect 1, having a structure represented by a formula:

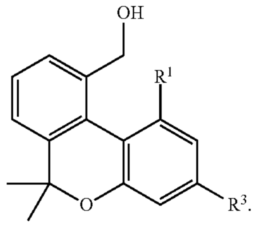

Aspect 13. The compound of Aspect 1, having a structure represented by a formula:

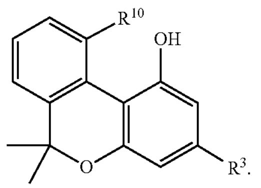

Aspect 14. The compound of Aspect 1, having a structure represented by a formula:

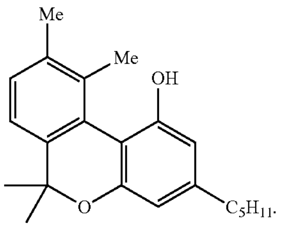

Aspect 15. The compound of Aspect 1, having a structure represented by a formula:

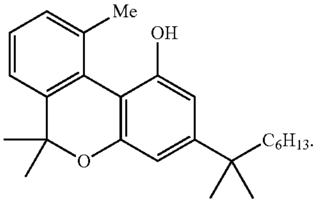

Aspect 16. The compound of Aspect 1, having a structure represented by a formula:

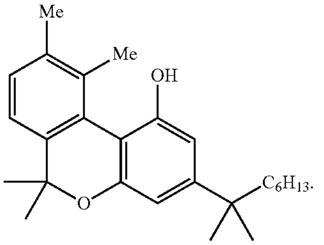

Aspect 17. A pharmaceutically composition comprising a therapeutically effective amount of a compound of any of Aspects 1-13, or a pharmaceutically acceptable salt, solvate, or polymorph thereof, and a pharmaceutically acceptable carrier.

Aspect 18. A method for the treatment of a disorder in a mammal, comprising the step of administering to the mammal a therapeutically effective amount of at least one compound of any of aspects 1-13, or a pharmaceutically acceptable salt thereof, or the pharmaceutical composition of aspect 14.

Aspect 19. The method of Aspect 18, wherein the mammal is a human.

Aspect 20. The method of Aspect 18, wherein the mammal has been diagnosed with a need for treatment of the disorder prior to the administering step.

Aspect 21. The method of Aspect 18, further comprising the step of identifying a mammal in need of treatment of the disorder.

Aspect 22. The method of Aspect 18, wherein the disorder is selected from Huntington's disease, arthritis, nervous tissue inflammation, vascular inflammation, inflammatory bowel disease, and other inflammation-related conditions.

Aspect 23. A method for modulating cannabinoid receptor activity in a mammal, comprising the step of administering to the mammal a therapeutically effective amount of at least one compound of any of aspects 1-13, or a pharmaceutically acceptable salt thereof, or the pharmaceutical composition of aspect 14.

Aspect 24. The method of Aspect 23, wherein the mammal is a human.

Aspect 25. The method of Aspect 23, wherein the cannabinoid receptor is cannabinoid receptor CB1, cannabinoid receptor CB2, or both.

Aspect 26. The method of Aspect 23, wherein the mammal has been diagnosed with a need for modulating cannabinoid receptor activity prior to the administering step.

Aspect 27. The method of Aspect 23, further comprising the step of identifying a mammal in need of modulating cannabinoid receptor activity.

Aspect 28. A kit comprising at least one compound of any of aspects 1-13, or a pharmaceutically acceptable salt thereof, and one or more of: (a) at least one agent known to increase cannabinoid receptor activity; (b) at least one agent known to decrease cannabinoid receptor activity; and (c) at least one agent known to treat Huntington's disease, arthritis, nervous tissue inflammation, vascular inflammation, inflammatory bowel disease, and other inflammation-related conditions.

Aspect 28. The kit of Aspect 28, further comprising instructions for treating Huntington's disease, arthritis, nervous tissue inflammation, vascular inflammation, inflammatory bowel disease, and other inflammation-related conditions.

Aspect 29. The method of Aspect 28, wherein the at least one compound and the at least one agent are co-formulated.

Aspect 30. The method of Aspect 28, wherein the at least one compound and the at least one agent are co-packaged.

Aspect 31. A method of synthesizing an axially chiral cannabinol analog, the method comprising: (a) reacting a compound of formula I with a substituted benzene molecule of formula II in the presence of a base and a metal salt to produce a product of formula III:

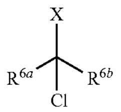

I

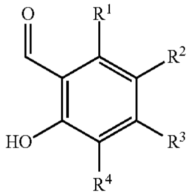

II

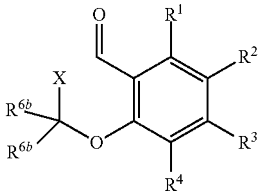

III wherein X comprises a carbon-carbon or carbon-nitrogen triple bond; (b) reacting the product of formula III with a compound of formula IV in the presence of a tertiary amine and a Lewis acid to produce a product of formula V:

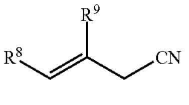

IV

-continued

V

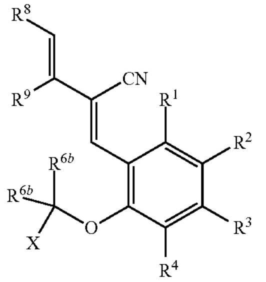

(c) performing a Diels-Alder cyclization on the product of formula V to produce a product of formula VI:

VI

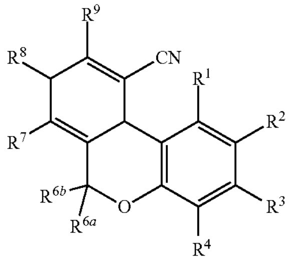

(d) using a dehydration agent to produce a product of formula VII:

VII

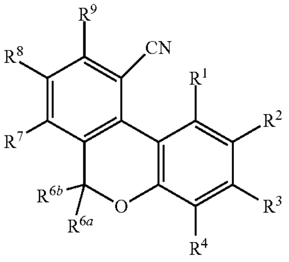

wherein $R^1$ is selected from hydrogen, halo, cyano, amino, hydroxyl, methoxy, acetoxy, —$OC_6H_5$, and —$OCH_2C6H_5$, optionally substituted alkyl, optionally substituted alkenyl, optionally substituted alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; wherein each of $R^2$, $R^4$, $R^{6a}$, and $R^{6b}$ is independently selected from hydrogen and C1-C6 alkyl; wherein $R^3$ is selected from hydrogen, halo, cyano, amino, hydroxyl, optionally substituted C1-C12 alkyl, optionally substituted alkenyl, optionally substituted C1-C12 alkynyl, optionally substituted —(C0-C12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl; and wherein each of $R^7$, $R^8$, and $R^9$ is independently selected from hydrogen, halo, cyano, amino, hydroxyl, optionally substituted alkyl, optionally substituted alkenyl, optionally substituted alkynyl, optionally substituted —(C0-12 alkyl)-aryl, optionally substituted —(C0-C12 alkyl)-heteroaryl, optionally substituted —(C0-C12 alkyl)-cycloalkyl, and optionally substituted —(C0-C12 alkyl)-heterocycloalkyl.

Aspect 32. The method of Aspect 31, wherein the compound of formula I is selected from IA and IB:

IA

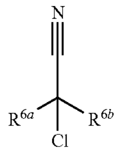

or

IB

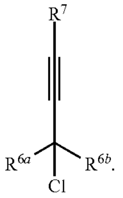

Aspect 33. The method of Aspect 31, wherein the base comprises 1,8-diazabicyclo(5.4.0)undec-7-ene (DBU), 1,5-diazabicyclo(4.3.0)non-5-ene (DBN), or 1,4-diazabicyclo [2.2.2]octane.

Aspect 34. The method of Aspect 31, wherein the metal salt comprises $CuCl_2$, $Cu_3(NO_3)_2$, $CuSO_4$, a combination thereof, or a hydrate thereof.

Aspect 35. The method of Aspect 31, wherein the tertiary amine comprises trimethylamine, N,N,N',N'-tetraethyl-1,3-propanediamine, N,N,N',N'-tetraethyl-1,3-butanediamine, N,N,N',N'-tetraethyl-1,3-hexanediamine, or a combination thereof.

Aspect 36. The method of Aspect 31, wherein the Lewis acid comprises $TiCl_4$ or $SnCl_4$.

Aspect 37. The method of Aspect 31, wherein Diels-Alder cyclization is performed at a temperature of from about 30 to about 150° C.

Aspect 38. The method of Aspect 31, wherein the Diels-Alder cyclization is performed at about 110° C.

Aspect 39. The method of Aspect 31, wherein the dehydrogenation agent comprises a quinone.

Aspect 40. The method of Aspect 39, wherein the quinone comprises 2,3-dichloro-5,6-dicyano-1,4-benzoquinone (DDQ).

Aspect 41. The method of Aspect 31, wherein $R^1$ is selected from hydroxyl, methoxy, and acetoxy.

Aspect 42. The method of Aspect 31, wherein $R^1$ is selected from hydroxyl and methoxy.

Aspect 43. The method of Aspect 31, wherein $R^1$ is hydroxyl.

Aspect 44. The method of Aspect 31, wherein $R^3$ is selected from C1-C6 alkyl, —(C0-C12 alkyl)-phenyl, and phenyl.

Aspect 45. The method of Aspect 31, wherein $R^3$ is selected from methyl, ethyl, propyl, isopropyl, tert-butyl, sec-butyl, isobutyl, neopentyl, isopentyl, sec-pentyl, and tert-pentyl.

Aspect 46. The method of Aspect 31, wherein $R^3$ is pentyl.

Aspect 47. The method of Aspect 31, wherein $R^1$ is methoxy, and further comprising: (e) reacting the product of formula VII with a nucleophile to produce a product of formula VIII:

VIII

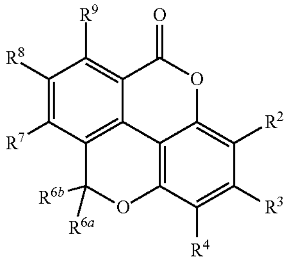

Aspect 48. The method of Aspect 47, wherein the nucleophile is sodium ethanethiolate (NaSEt).

Aspect 49. The method of Aspect 47, further comprising: (f) reacting the product of formula VIII with a reducing agent to produce a product of formula IX:

IX

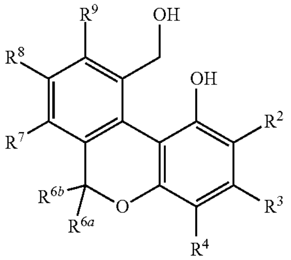

Aspect 50. The method of Aspect 49, wherein the reducing agent comprises $LiAlH_4$, $NaBH_4$, NaH, LiH, $CaH_2$, or a combination thereof.

Aspect 51. The method of aspect 50, wherein the reducing agent is $LiAlH_4$.

Aspect 52. The method of any of aspects 31-51, further comprising post-synthetic modification of $R^1$, $R^2$, $R^3$, $R^4$, $R^{6a}$, $R^{6b}$, $R^7$, $R^8$, $R^9$, or a combination thereof.

Aspect 53. An axially chiral cannabinol analog produced by the method of any of aspects 31-52.

Aspect 54. The method of aspect 49, further comprising: (g) reacting the product of formula VII with a nucleophile to produce a product of formula X:

X

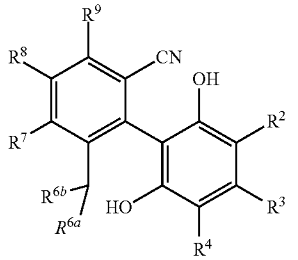

Aspect 55. The method of Aspect 54, wherein the nucleophile is sodium ethanethiolate (NaSEt).

Aspect 56. The method of Aspect 54 or 55, further comprising post-synthetic modification of $R^1$, $R^2$, $R^3$, $R^4$, $R^{6a}$, $R^{6b}$, $R^7$, $R^8$, $R^9$, or a combination thereof.

Aspect 57. A biaryl compound produced by the method of any of aspects 54-56.

Aspect 58. The biaryl compound of Aspect 57, having a structure represented by a formula:

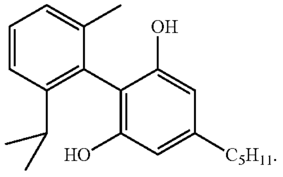

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

General Experimental Methods

All commercial materials were used without further purification. $^1H$ NMR and $^{13}C$ NMR spectra were recorded in $CDCl_3$ (with $CHCl_3$ residual peak as an internal standard) or toluene-da using a 500 MHz spectrometer. All $^{13}C$ NMR spectra were recorded with complete proton decoupling. HRMS data were recorded on Agilent Time of Flight 6200 spectrometer. Reaction progress was monitored by thin-layer chromatography (TLC) and visualized by UV light, phosphomolybdic acid stain, and $KMnO_4$ stain. All reactions were carried out using anhydrous solvents obtained dried by passing through activated alumina columns.

Exemplary Synthesis

Figure 10:
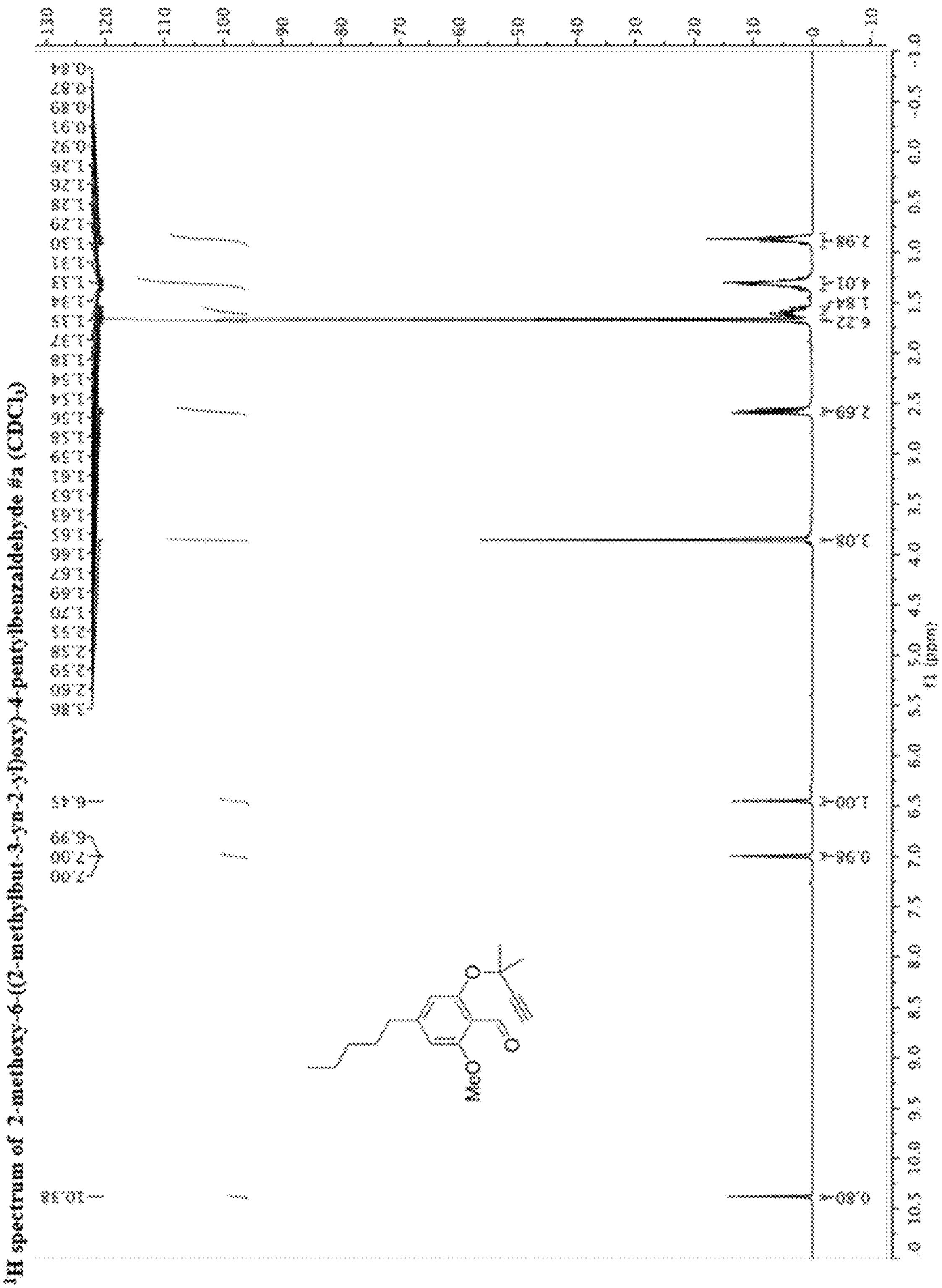
FIG. 10 shows a representative $^1$H NMR spectrum of a representative disclosed compound, 2-methoxy-6-((2-methylbut-3-yn-2-yl)oxy)-4-pentylbenzaldehyde, obtained using $CDCl_3$ as a solvent.
Figure 11:
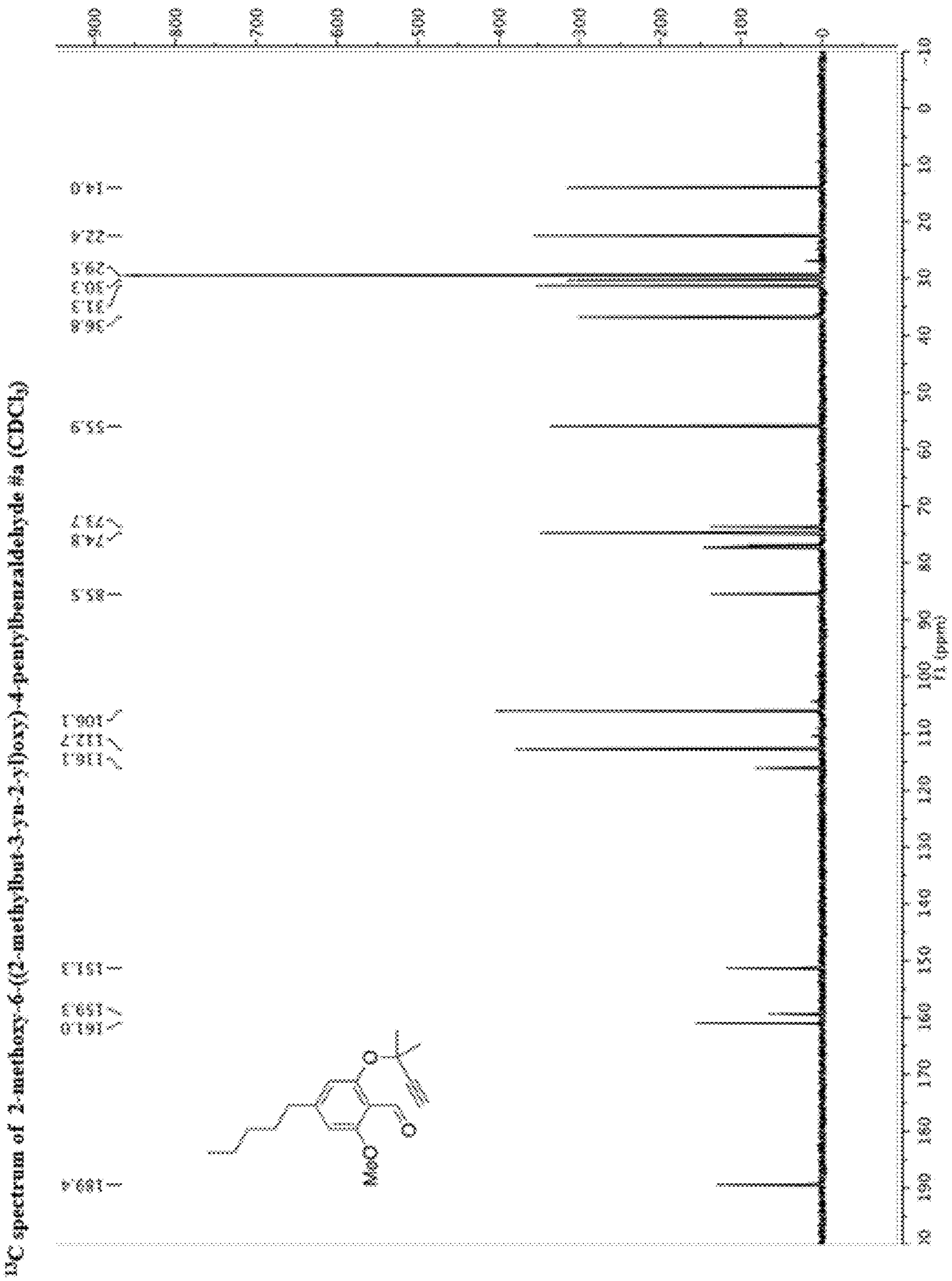
FIG. 11 shows a representative $^{13}$C NMR spectrum of a representative disclosed compound, 2-methoxy-6-((2-methylbut-3-yn-yl)oxy)-4-pentylbenzaldehyde, obtained using $CDCl_3$ as a solvent.

An exemplary synthesis for the disclosed compounds is immediately below (and also shown in FIG. 3A). Briefly, salicylaldehyde 1 was reacted with 1,1-dimethylpropargyl chloride via copper-catalysis to yield the phenyl propargyl ether 2 (see $^1H$ NMR in FIG. 10, $^{13}C$ NMR in FIG. 11). Aldol-like condensation of 2 with allylnitrile yielded an inseparable mixture 2.5:1 mixture of Z:E dienes 3. Only the major diastereomer underwent intramolecular Diels-Alder cycloaddition to 4. The 1,4-dihydrocannabinol 4 was converted to the biaryl scaffold 5 by DDQ-promoted oxidation. Treatment of the biaryl with sodium ethanethiolate promoted a demethylation/intramolecular Pinner sequence, which ultimately resulted in an achiral/planar lactone 6 post imidate hydrolysis. The targeted ax-CBN is prepared by $LiAlH_4$ reduction. The overall synthesis from salicylaldehydes, propargyl electrophiles, and allylnitriles is scalable: over a gram of ax-CBN was prepared using the reaction conditions described herein below. The disclosed synthesis is convergent, thus allowing\r structural analogs to be generated by choice of starting material. For example, crotyl nitrile in lieu of allyl nitrile yields 8-Me-ax-CBN via the standard route (see FIG. 3B). The sequence can also be diverted to make unique axially-chiral scaffolds. For example, we found that mild bases promote an elimination/aromatization sequence on the 1,4-dihydrocannabinol scaffolds to yield substituted biaryls. Further details for each reaction step are provided herein below.

Figure 7:
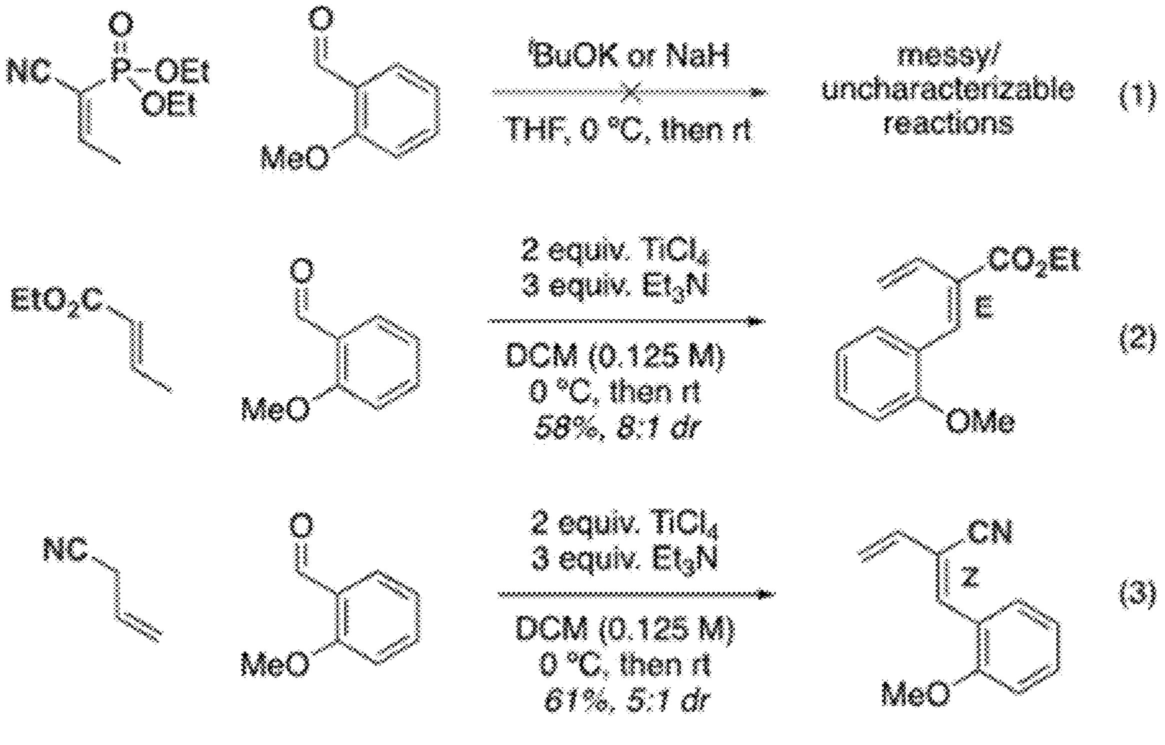
FIG. 7 shows representative disclosed syntheses showing the usefulness of (E)-alk-3-enenitriles and (E)-alk-3-eneesters in the disclosed methods of preparing substituted axially-chiral cannabinols.

Other synthesis methods were examined as alternatives to use of the allyl nitrile. For example, Homer-Wadsworth-Emmons (HWE) conditions were explored for establishing the diene (FIG. 7, eq 1). Under these conditions, the model system did not yield clean transformations. Without wishing to be bound by a particular theory, it is possible that the reaction carried out using HWE conditions did not proceed satisfactorily because of steric issues as well as undesired vinylogous-HWE reactions, which is known in the art to

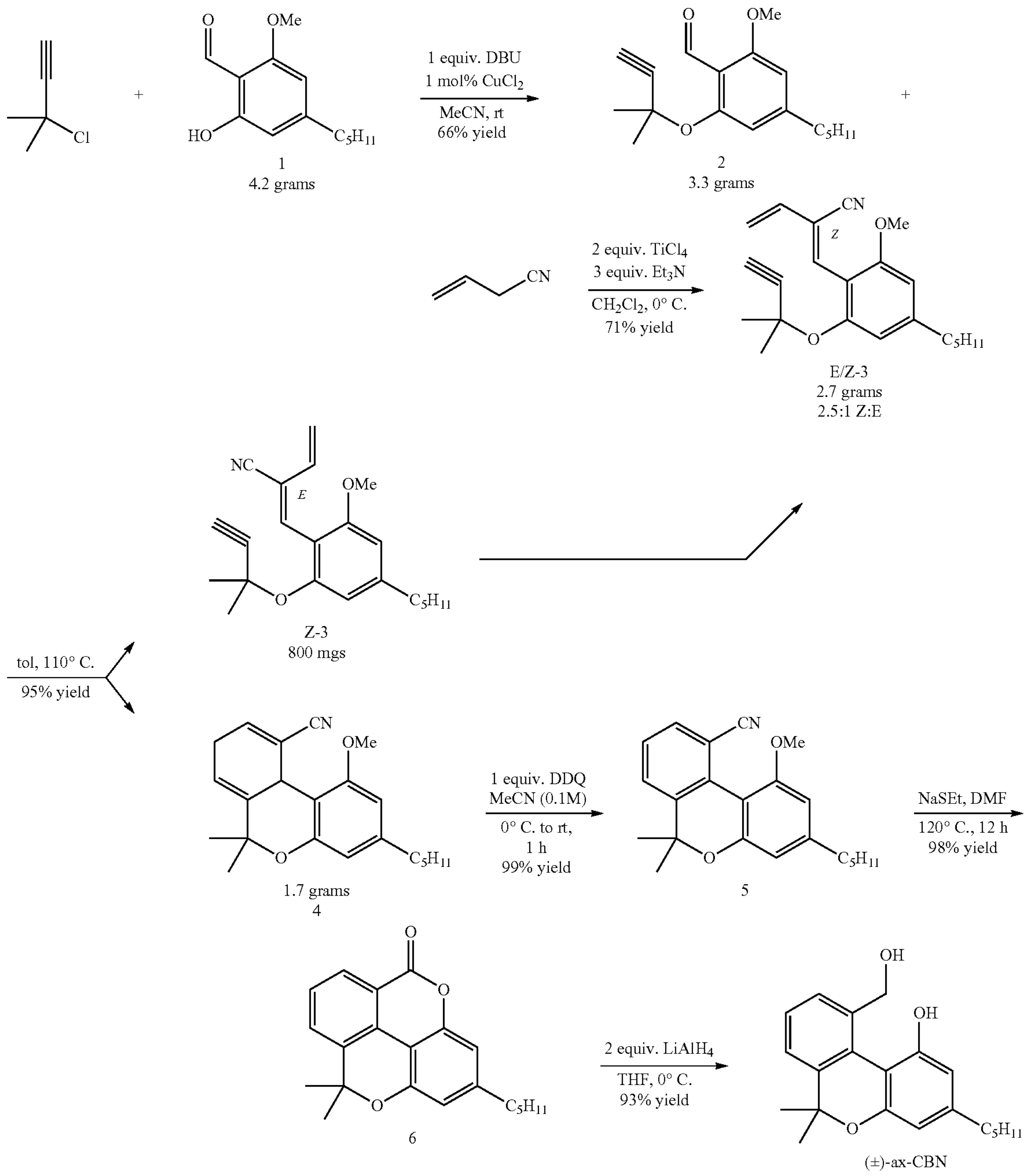

In the synthesis presented above, allylnitrile yields the desired Z-diene diastereomer as the major project. The minor E-diastereomer byproduct does not undergo Diels-Alder cycloaddition. However, it can be recycled back to the Z-diene by acid catalyzed isomerization as shown above.

yield undesired regiochemical outcome. A further alternative explored was able to achieve vinylogous aldol-condensation using ethyl crotonate with the model benzaldehyde, however, the undesired E-diene geometry was major (FIG. 7, eq 2). Based on these studies, the nitrile, being sterically small, is a preferred choice for both desired reactivity and E-diene diastereoselectivity in both model (FIG. 7, eq 3) and target studies (as shown above).

Procedure for Propargylation

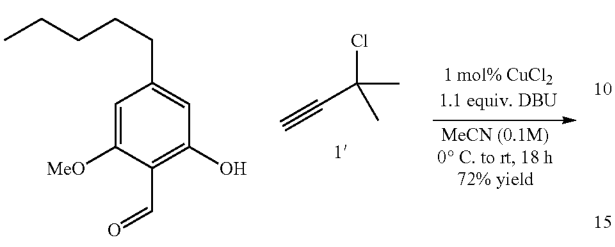

1

1'

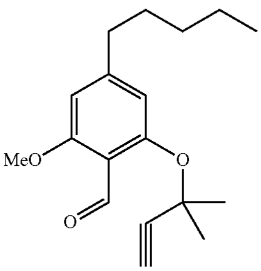

2

To an oven dried Schlenk flask, aldehyde 1 (5 g, 22.5 mmol, 1 equiv.), 1,8-diazabicyclo[5.4.0]undec-7-ene (3.7 ml, 24.7 mmol, 1.1 equiv.), 3-chloro-3-methylbut-1-yne 1' (2.5 mL, 22.5 mmol, 1 equiv.) and acetonitrile (225 mL, 0.1 M with respect to 1) was transferred and stirred for 5 minutes at 0° C. (ice bath) while blanketing with an inert gas. Then, copper(II) chloride dihydrate catalyst (38 mg, 225 μmol, 0.01 equiv.) was transferred at 0° C. The ice bath was removed and the reaction mixture was stirred overnight at room temperature. Upon completion via TLC, the reaction mixture was quenched with 100 ml of 1 M NaOH and transferred to a separatory funnel and extracted with ethyl acetate (2×50 mL). The combined organic layers were washed with 1 M HCl (1×50 mL), saturated $NaHCO_3$ (1×50 mL), brine (1×50 mL) and dried over $Na_2SO_4$. The crude solution was evaporated and purified using column chromatography (hexanes-ethyl acetate 90:10) which gave 2-methoxy-8-((2-methylbut-3-yn-2-yl)oxy)-4-pentylbenzaldehyde (4.7 g, 72%) as a yellow oil.

Procedure for Aldol-Like Condensation

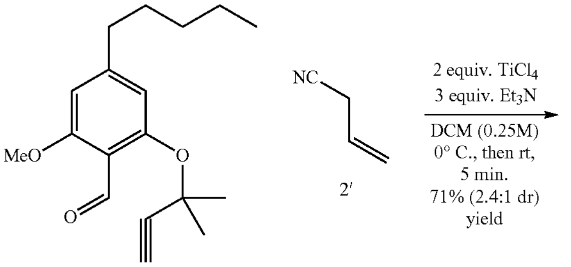

2

2'

-continued

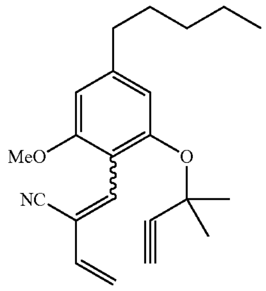

Z/E-3

To an oven dried Schlenk flask, aldehyde 2 (4.7 g, 16.2 mmol, 1 equiv.), triethylamine (6.8 mL, 48.7 mmol, 3 equiv.), allyl cyanide 2' (2.6 mL, 32.5 mmol, 2 equiv.) and dichloromethane (65 mL, 0.25 M with respect to 2) was transferred and stirred for 5 minutes at 0° C. (ice bath) while blanketing with an inert gas. Then, titanium(IV) tetrachloride (3.6 mL, 32.5 mmol, 2 equiv.) was transferred drop wise over 5 minutes and stirred for another 5 minutes at 0° C. Upon completion via TLC, the reaction mixture was quenched with 15 mL of water and transferred to a separatory funnel and extracted with dicloromethane (2×10 ml). The combined organic layers were washed with brine (1×20 mL) and dried over $Na_2SO_4$. The crude solution was evaporated and purified using column chromatography (hexanes-ethyl acetate 95:5) which gave 2-(2-methoxy-6-((2-methylbut-3-yn-2-yl)oxy)-4-pentylbenzylidene)but-3-enenitrile (3.3 g, 71%, 2.4:1 dr) as a yellow oil.

Procedure for [4+2] Cycloaddition

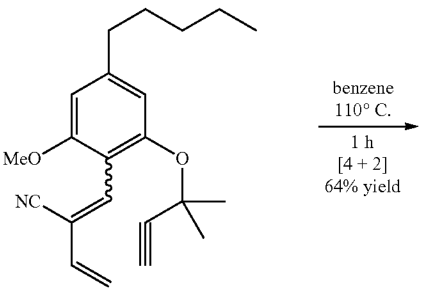

Z/E-3

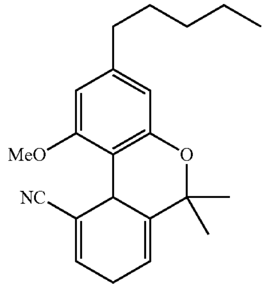

4

-continued

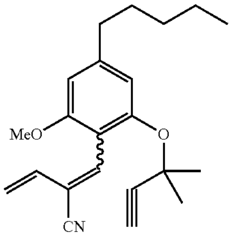

E-3

To an oven dried pressure flask, Z/E-3 (3.3 g, 9.8 mmol, 1 equiv.) and dry toluene (98 mL, 0.1 M with respect to Z/E-3) was transferred and heated at 110° C. for 1 hour. The crude solution was evaporated and purified using column chromatography (hexanes-ethyl acetate 90:10) which gave 1-methoxy-6,6-dimethyl-3-pentyl-8,10a-dihydro-6H-benzo[c]chromene-10-carbonitrile (2 g, 64%) as a yellow oil and starting material E-3 (1 g, 30% of Z/E-3).

Procedure for Oxidation Reaction

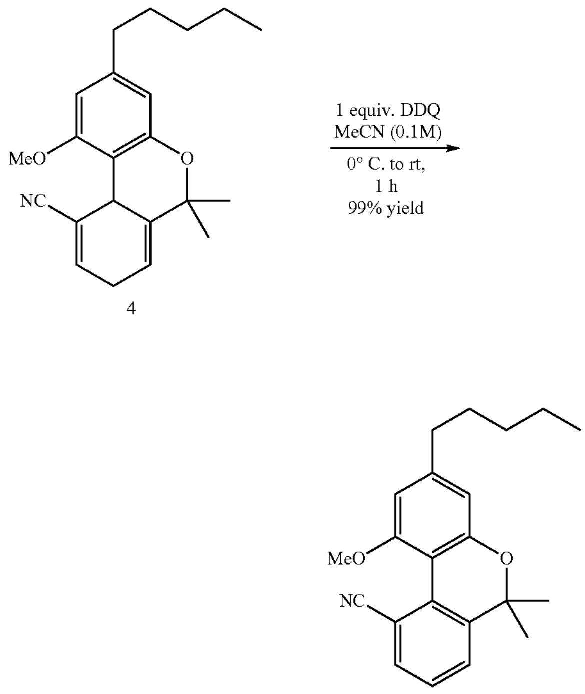

4

(±)-5

To an oven dried Schlenk flask, 4 (2 g, 6 mmol, 1 equiv.), 2,3-Dichloro-5,6-dicyano-1,4-benzoquinone (1.4 g, 24.7 mmol, 1 equiv.) and acetonitrile (59 mL, 0.1 M with respect to 4) was transferred and stirred for 1 hour at 0° C. (ice bath) while blanketing with an inert gas. Upon completion via TLC, the reaction mixture was passed through a short plug of silica. The crude solution was evaporated and purified using column chromatography (hexanes-ethyl acetate 90:10) which gave 1-methoxy-6,6-dimethyl-3-pentyl-6H-benzo[c]chromene-10-carbonitrile (2 g, 99%) as a yellow oil.

Procedure for Demethylation

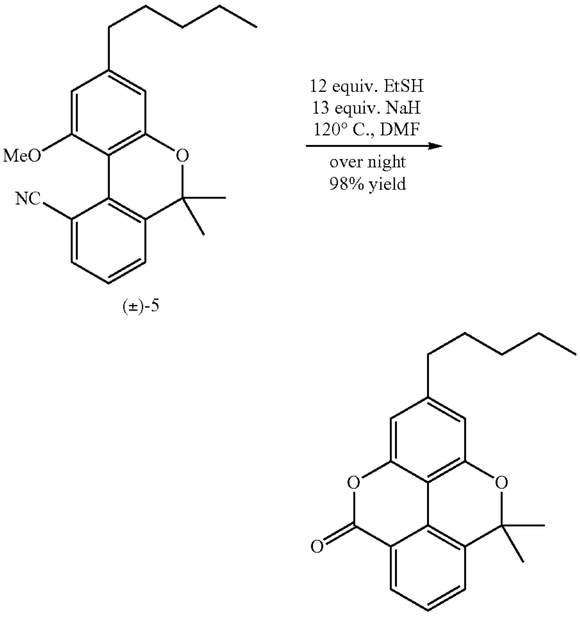

(±)-5

6

To an oven dried Schlenk flask, NaH (1.9 g, 77.5 mmol, 13 equiv.) and dimethylformamide (15.6 mL, 5 M with respect to NaH) was transferred and cooled to 0° C. (ice bath) while blanketing with an inert gas. Then, EtSH (5.2 mL, 71.6 mmol, 12 equiv.) was transferred drop wise at 0° C. and stirred at room temperature for 30 minutes. 1-methoxy-6,6-dimethyl-3-pentyl-6H-benzo[c]chromene-10-carbonitrile (2 g, 6 mmol, 1 equiv.) was transferred with dimethylformamide (23.4 mL, 0.15 M overall concentration with respect to carbonitrile) and stirred over night at 120° C. The reaction mixture was quenched with 20 mL of water and transferred to a separatory funnel and extracted with ethyl acetate (3x20 mL). The combined organic layers were washed with brine (1x20 mL) and dried over $Na_2SO_4$. The crude solution was evaporated and purified using column chromatography (hexanes-ethyl acetate 90:10). The imidate was hydrolyzed during the chromatography process and gave lactone 6 (1.9 g, 98%) as yellow oil. As required, excess EtSH in water following the reaction work-up can be quenched using 5% bleach (5% NOCl in water).

Procedure for Reduction

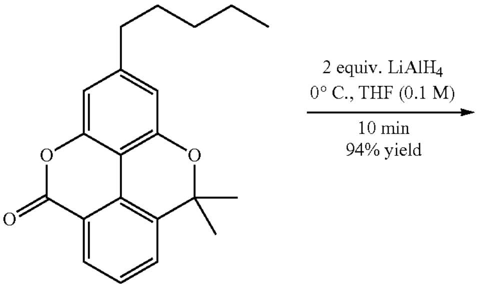

6

-continued

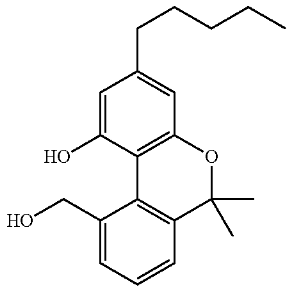

(±)-ax-CBN

To an oven dried Schlenk flask, lactone 6 (1.9 g, 5.9 mmol, 1 equiv.) and THF (59 mL, 0.1 M with respect to 6) was transferred and cooled to 0° C. (ice bath) while blanketing with an inert gas. Then, $LiAlH_4$ (447 mg, 11.8 mmol, 2 equiv.) was transferred at 0° C. and stirred for 10 minutes. Upon completion via TLC, the reaction mixture was quenched with 25 mL of saturated Rochelle's salt for 1 hour and transferred to a separatory funnel and extracted with ether (3×20 mL). The combined organic layers were washed with brine (1×20 mL) and dried over $Na_2SO_4$. The crude solution was evaporated and purified using column chromatography (hexanes-ethyl acetate 80:20) which gave 10-(hydroxymethyl)-6,6-dimethyl-3-pentyl-6H-benzo[c]chromen-1-ol (1.8 g, 94%) as a white solid.

2-methoxy-6-((2-methylbut-3-yn-2-yl)oxy)-4-pentylbenzaldehyde (2)

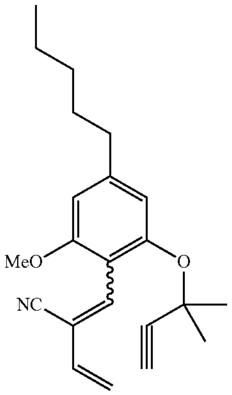

Figure 12:
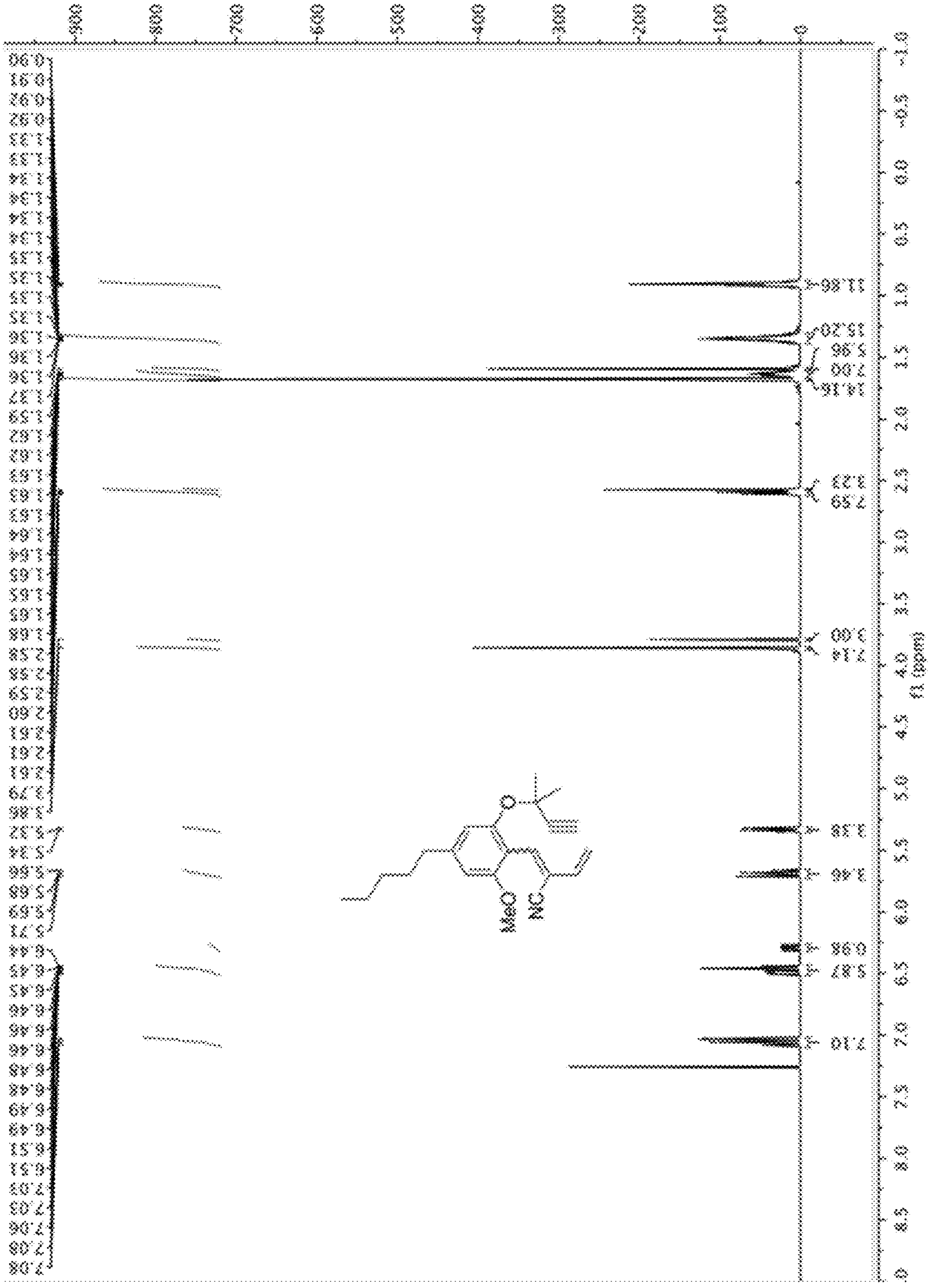
FIG. 12 shows a representative $^1$H NMR spectrum of a representative disclosed compound, 2-(2-methoxy-8-((2-methylbut-3-yn-2-yl)oxy)-4-pentylbenzylidene)but-3-enenitrile, obtained using $CDCl_3$ as a solvent.
Figure 13:
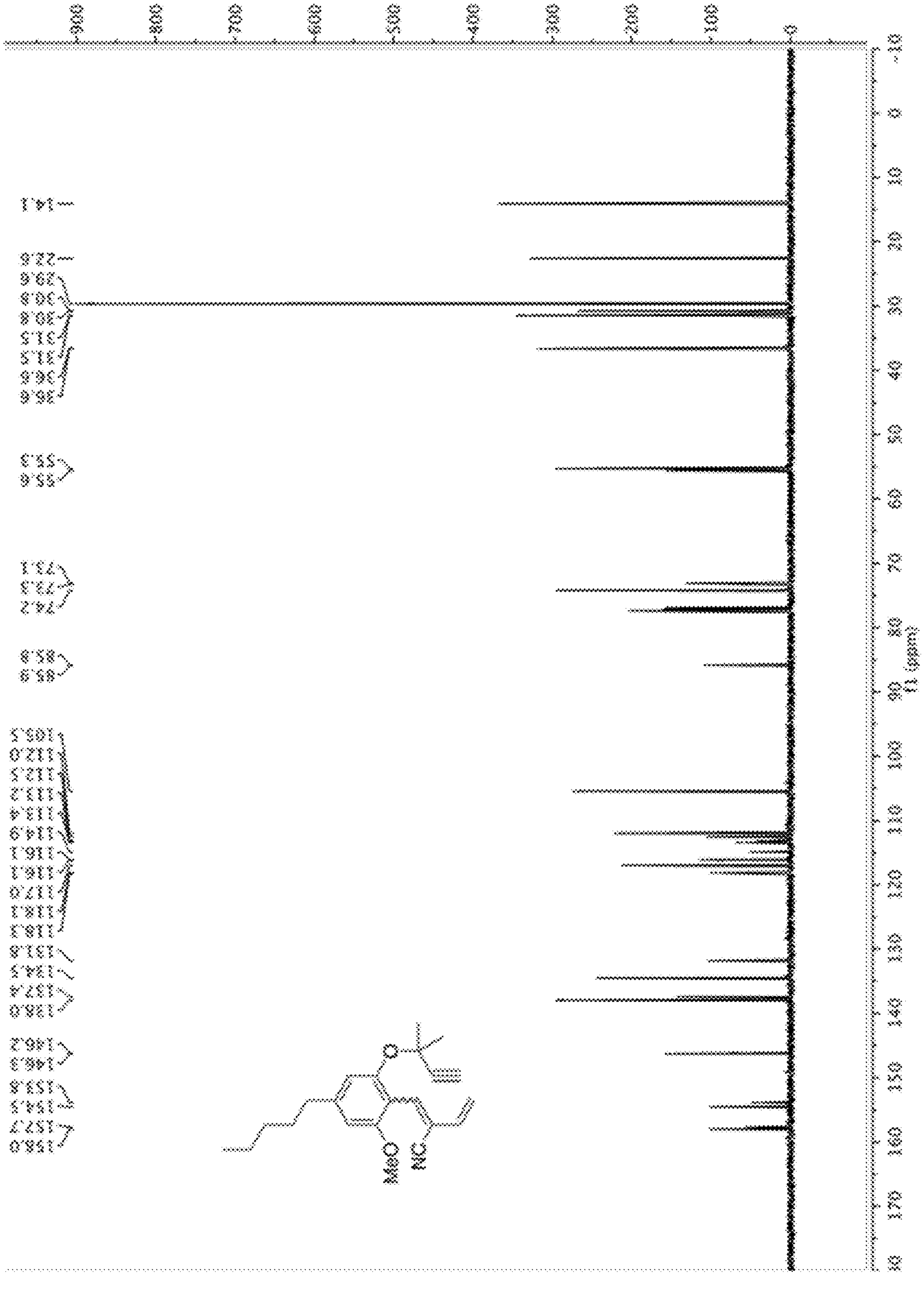
FIG. 13 shows a representative $^{13}$C NMR spectrum of a representative disclosed compound, 2-(2-methoxy-6-((2-methylbut-3-yn-2-yl)oxy)-4-pentylbenzylidene)but-3-enenitrile, obtained using $CDCl_3$ as a solvent.

Obtained as a yellow liquid, 4.7 g, 72%. $^1$H NMR (FIG. 12) (500 MHz, $CDCl_3$) δ 10.38 (s, 1H), 7.00 (s, 1H), 6.45 (s, 1H), 3.86 (s, 3H), 2.62-2.54 (m, 3H), 1.67 (s, 6H), 1.62-1.54 (m, 2H), 1.31 (dq, J=7.6, 3.5 Hz, 4H), 0.89 (t, J=6.9 Hz, 3H). $^{13}$C NMR (FIG. 13) (125 MHz, $CDCl_3$) δ 189.4, 161.0, 159.3, 151.3, 116.1, 112.7, 106.1, 85.5, 74.8, 73.7, 55.9, 36.8, 31.3, 30.3, 29.5, 22.5, 14.0. Rr: 0.6 (hexanes-ethyl acetate 85:15)

1-methoxy-6,6-dimethyl-3-pentyl-8,10a-dihydro-6H-benzo[c]chromene-10-carbonitrile (4)

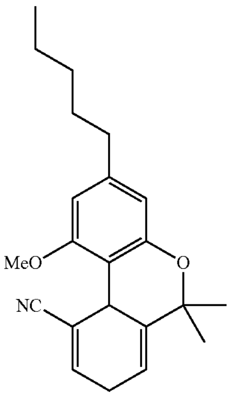 [SMILES: CCCCCc1cc(OC)c2c(c1)OC(C)(C)C1=CCC=C(C#N)C12]

Figure 14:
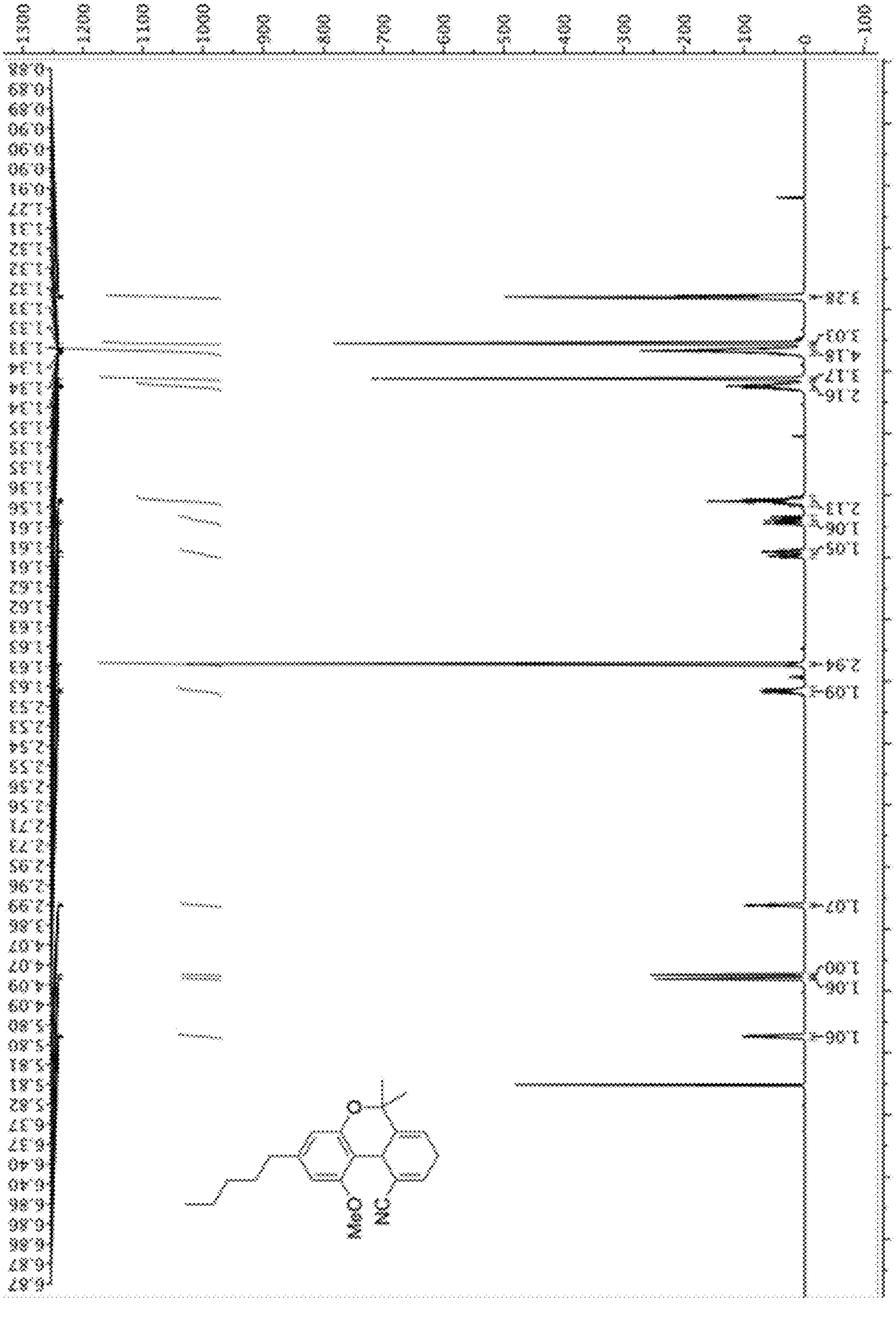
FIG. 14 shows a representative $^1$H NMR spectrum of a representative disclosed compound, 1-methoxy-6,6-dimethyl-3-pentyl-8,10a-dihydro-6H-benzo[c]chromene-10-carbonitrile, obtained using $CDCl_3$ as a solvent.
Figure 15:
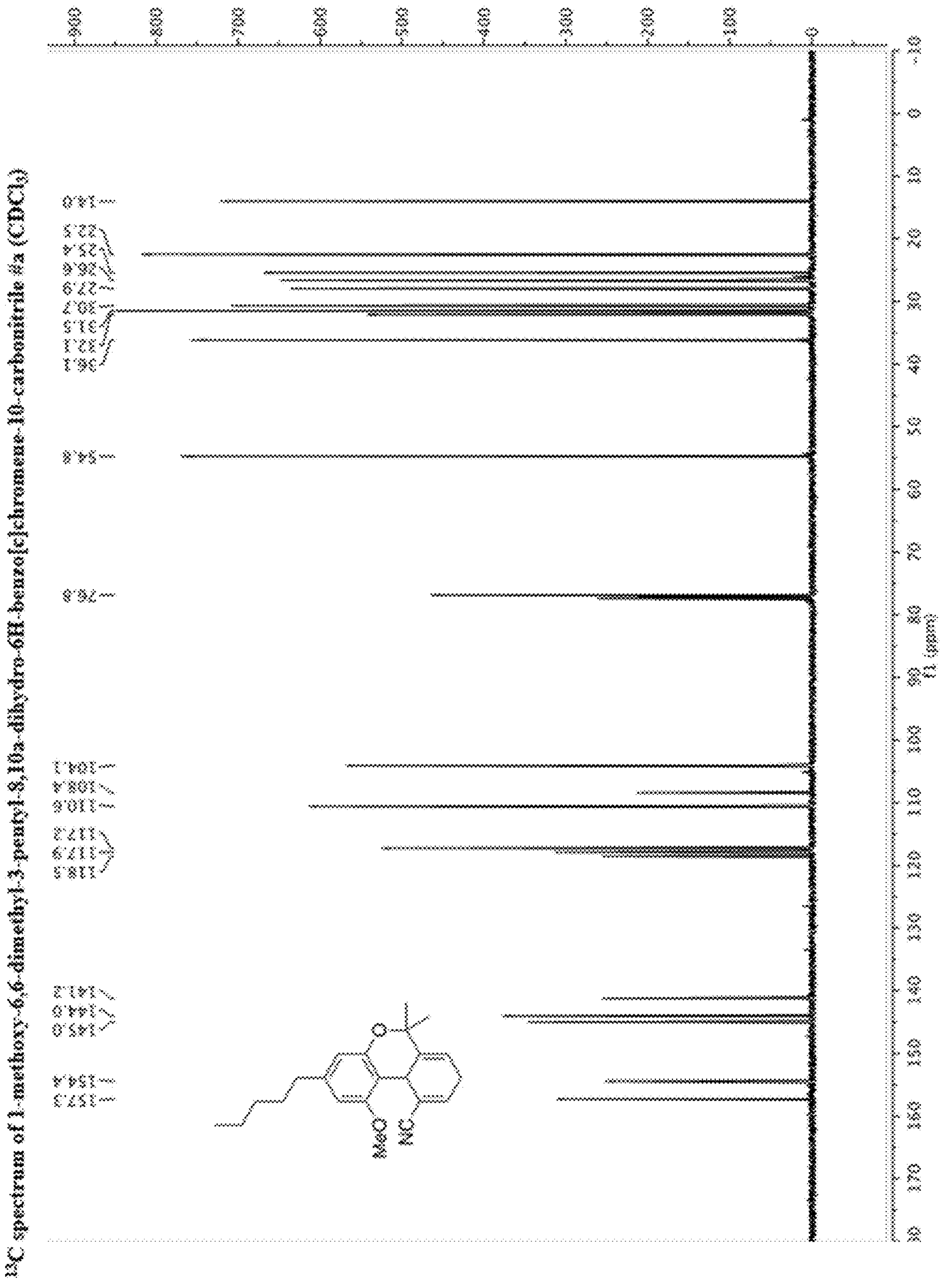
FIG. 15 shows a representative $^{13}$C NMR spectrum of a representative disclosed compound, 1-methoxy-6,6-dimethyl-3-pentyl-8,10a-dihydro-6H-benzo[c]chromene-10-carbonitrile, obtained using $CDCl_3$ as a solvent.

Obtained as a yellow liquid, 2 g, 68%. $^1$H NMR (FIG. 14) (500 MHz, $CDCl_3$) δ 6.86 (ddd, J=5.6, 3.1, 1.0 Hz, 1H), 6.40 (d, J=1.5 Hz, 1H), 6.37 (d, J=1.5 Hz, 1H), 5.81 (dt, J=5.2, 2.4 Hz, 1H), 4.08 (dt, J=4.1, 2.1, 1.6 Hz, 1H), 3.86 (s, 3H), 2.97 (dtd, J=21.8, 5.9, 4.2 Hz, 1H), 2.70 (ddt, J=21.5, 11.8, 2.5 Hz, 1H), 2.54 (td, J=7.5, 2.6 Hz, 2H), 1.65-1.59 (m, 2H), 1.56 (s, 3H), 1.37-1.31 (m, 4H), 1.27 (s, 3H), 0.90 (t, J=6.9 Hz, 3H). $^{13}$C NMR (FIG. 15) (125 MHz, $CDCl_3$) δ 157.3, 154.4, 145.0, 144.0, 141.2, 118.5, 117.9, 117.2, 110.6, 108.4, 104.1, 76.8, 54.8, 36.1, 32.1, 31.5, 30.7, 27.9, 26.6, 25.4, 22.5, 14.0. Re: 0.6 (hexanes-ethyl acetate 90:10)

1-methoxy-6,6-dimethyl-3-pentyl-6H-benzo[c]chromene-10-carbonitrile (5)

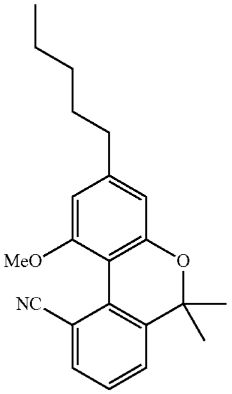 [SMILES: CCCCCc1cc(OC)c2c(c1)OC(C)(C)c1cccc(C#N)c1-2]

Figure 16:
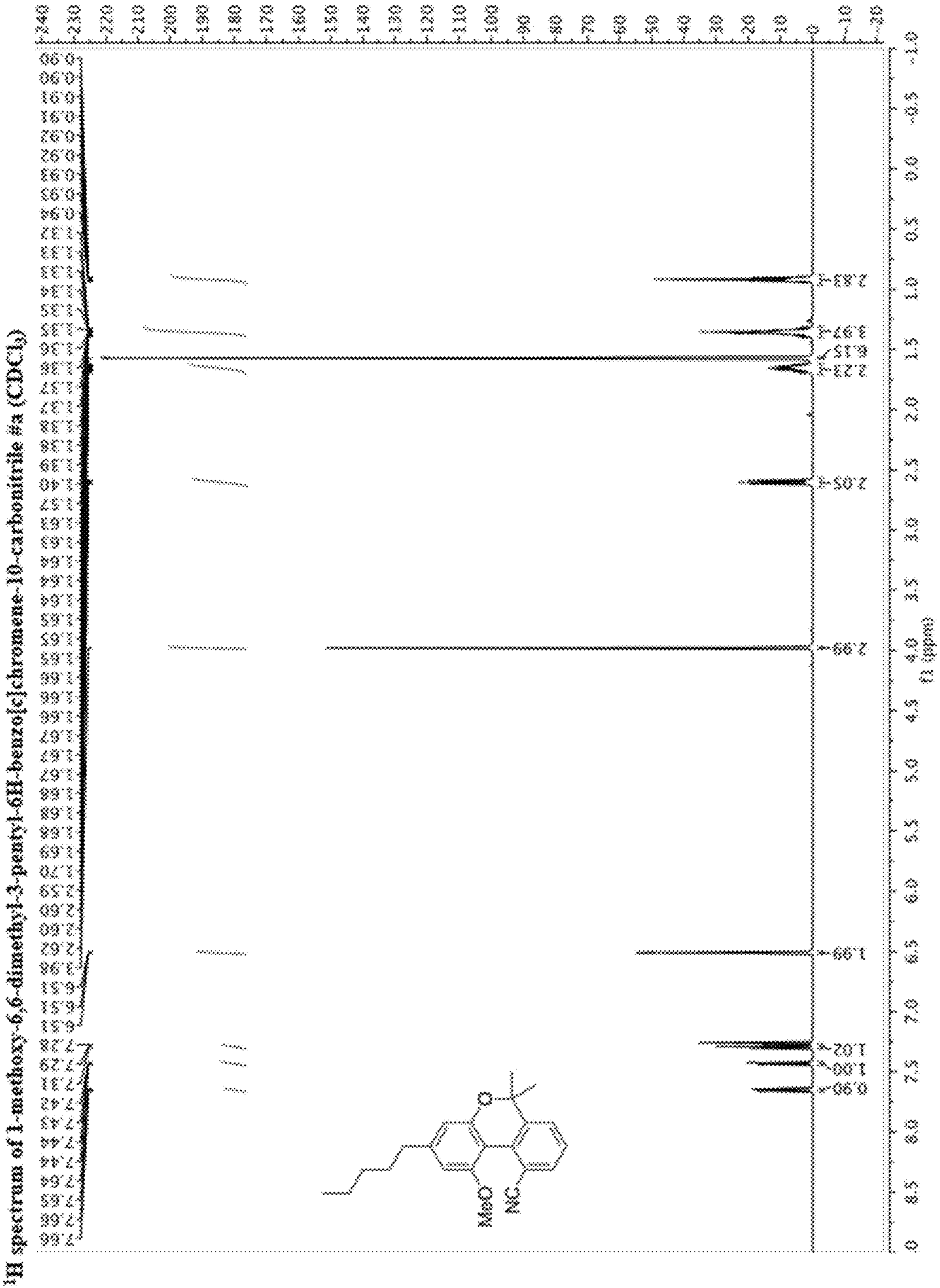
FIG. 16 shows a representative $^1$H NMR spectrum of a representative disclosed compound, 1-methoxy-6,6-dimethyl-3-pentyl-6H-benzo[c]chromene-10-carbonitrile, obtained using $CDCl_3$ as a solvent.
Figure 17:
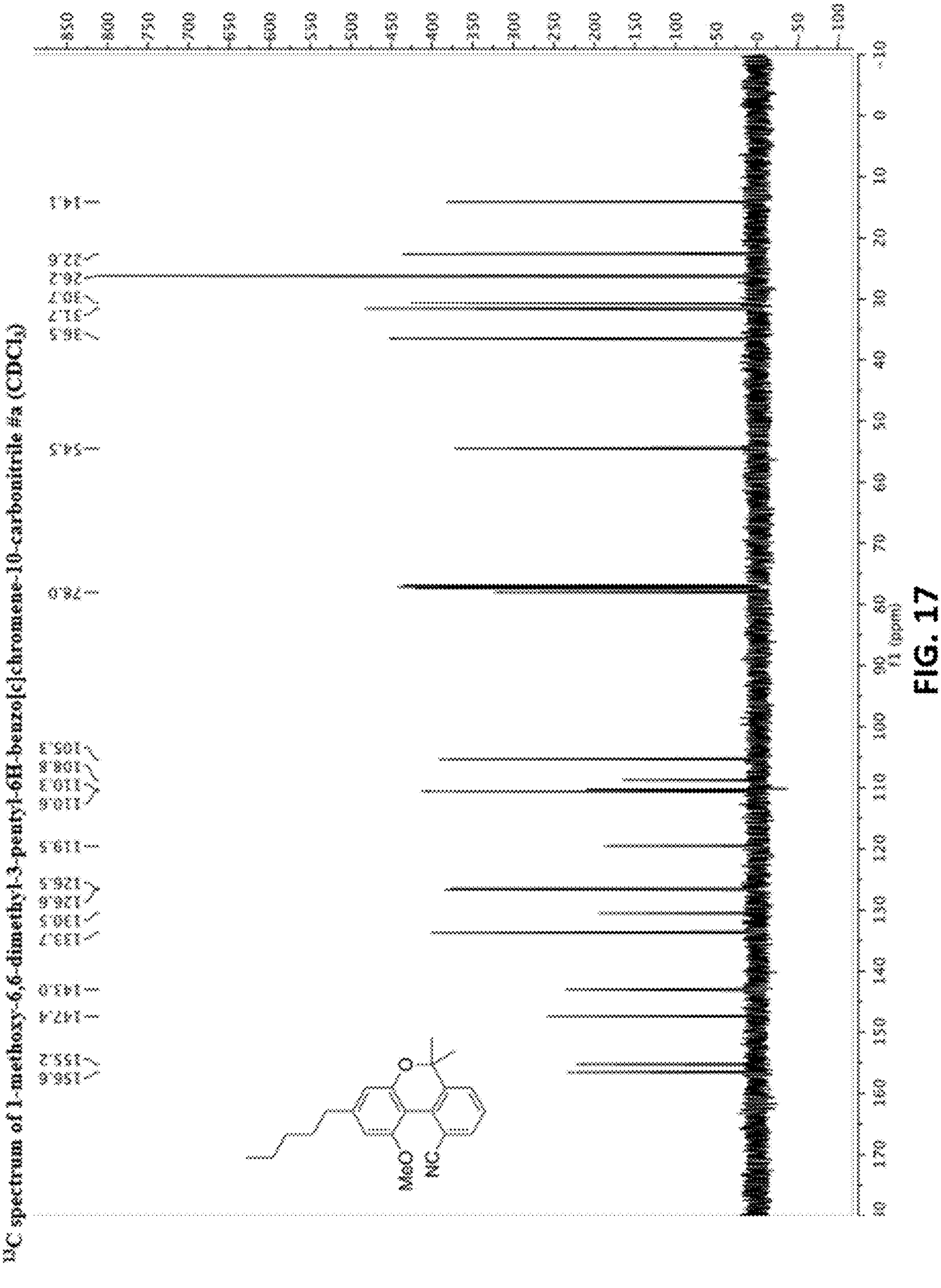
FIG. 17 shows a representative $^{13}$C NMR spectrum of a representative disclosed compound, 1-methoxy-6,6-dimethyl-3-pentyl-6H-benzo[c]chromene-10-carbonitrile, obtained using $CDCl_3$ as a solvent.

Obtained as a yellow liquid, 1.9 g, 99%. $^1$H NMR (FIG. 16) (500 MHz, $CDCl_3$) δ 7.65 (dd, J=7.7, 1.3 Hz, 1H), 7.43 (dd, J=7.8, 1.3 Hz, 1H), 7.29 (t, J=7.7 Hz, 1H), 6.51 (d, J=0.9 Hz, 2H), 3.98 (s, 3H), 2.60 (t, J=7.9 Hz, 2H), 1.71-1.62 (m, 2H), 1.57 (s, 6H), 1.36 (dq, J=7.5, 3.9, 3.5 Hz, 4H), 0.92 (t, J=6.9 Hz, 3H). $^{13}$C NMR (FIG. 17) (125 MHz, $CDCl_3$) δ 156.6, 155.3, 147.4, 143.0, 133.7, 130.5, 126.6, 126.5, 119.5, 110.6, 110.3, 108.8, 105.3, 78.0, 54.5, 36.5, 31.7, 30.7, 26.2, 22.7, 14.1. Rr: 0.65 (hexanes-ethyl acetate 90:10).

9,9-dimethyl-2-pentyl-5H,9H-Isochromeno[5,4,3-cde]chromen-5-one (6)

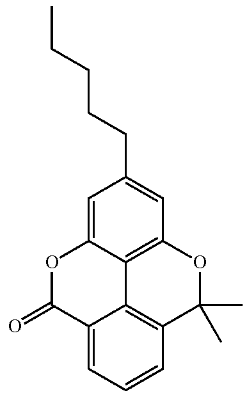 [SMILES: CCCCCc1cc2c3c(c1)oc(=O)c1cccc(c13)C(C)(C)O2]

Figure 18:
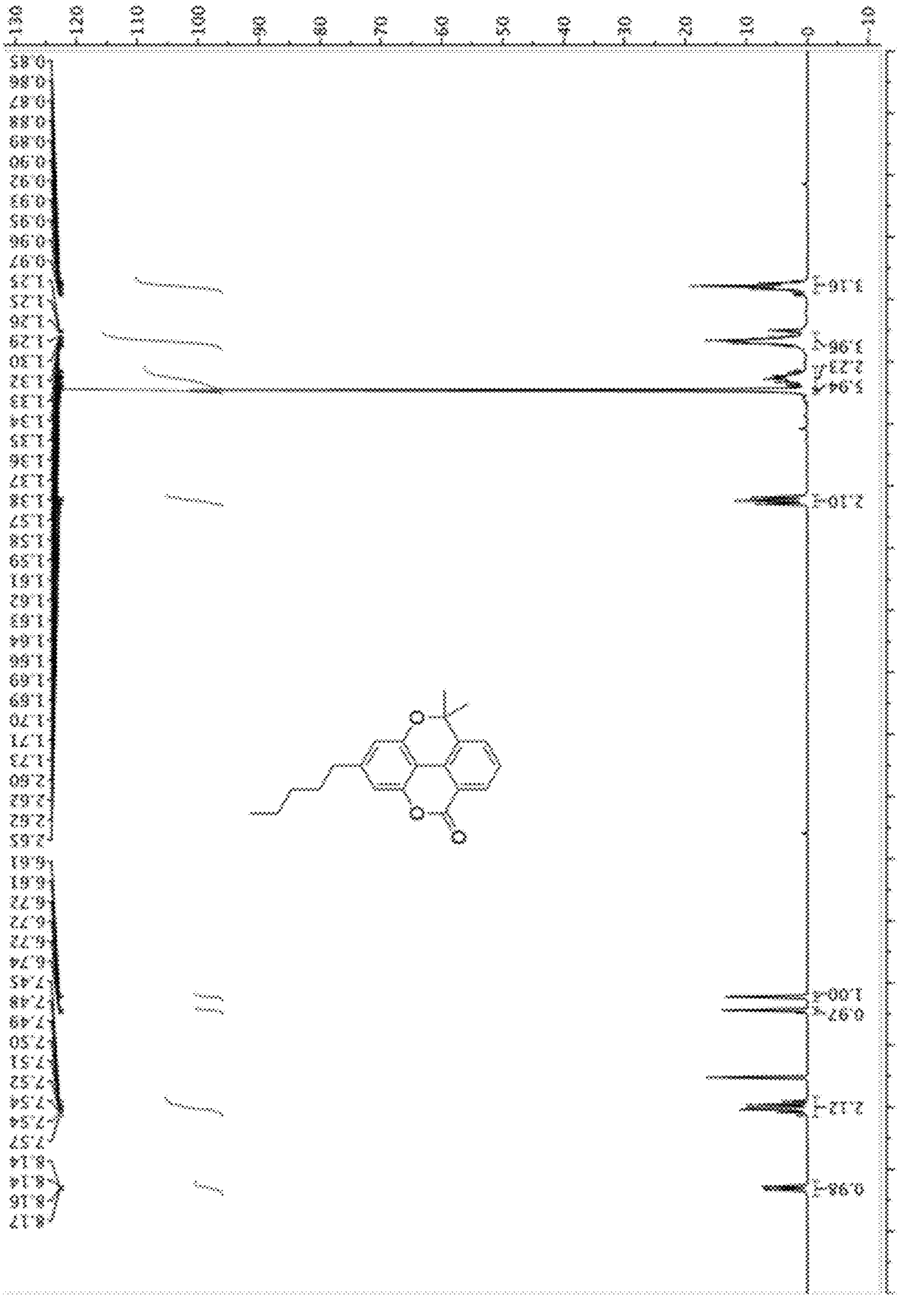
FIG. 18 shows a representative $^1$H NMR spectrum of a representative disclosed compound, 9,9-dimethyl2-pentyl-5H,9H-isochromeno[5,4,3-cde]chromen-5-one, obtained using $CDCl_3$ as a solvent.
Figure 19:
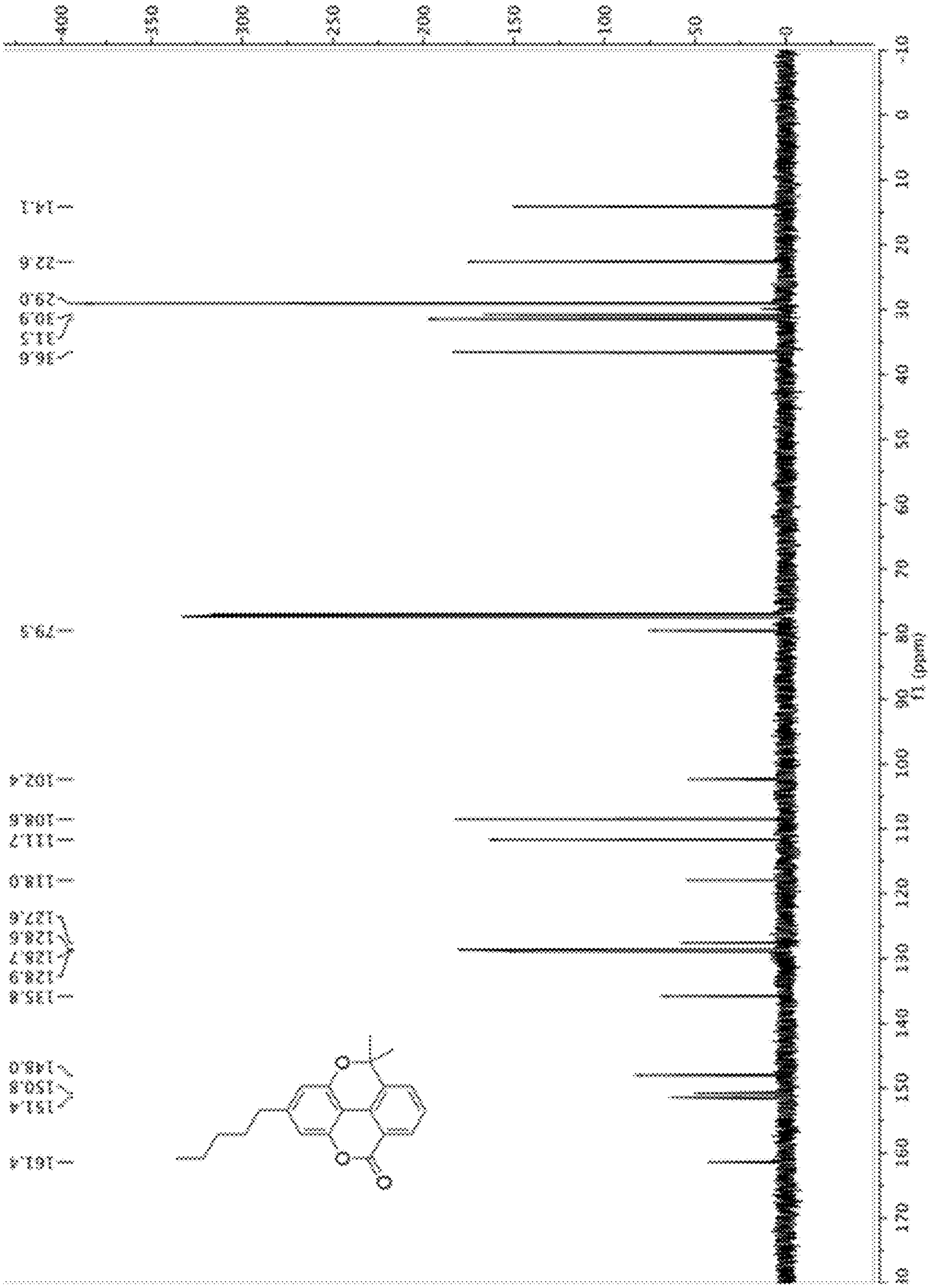
FIG. 19 shows a representative $^{13}$C NMR spectrum of a representative disclosed compound, 9,9-dimethyl-2-pentyl-5H,9H-isochromeno[5,4,3-cde]chromen-5-one, obtained using $CDCl_3$ as a solvent.

Obtained as a yellow liquid, 1.9 g, 98%. $^1$H NMR (FIG. 18) (500 MHz, $CDCl_3$) δ 8.15 (dd, J=7.5, 1.5 Hz, 1H), 7.58-7.42 (m, 2H), 6.72 (s, 1H), 6.61 (s, 1H), 2.62 (dd, J=8.6, 6.8 Hz, 2H), 1.73 (s, 6H), 1.72-1.54 (m, 2H), 1.33 (dq, J=7.2, 3.6, 3.2 Hz, 4H), 0.89 (t, J=6.7 Hz, 3H). $^{13}$C NMR (FIG. 19) (125 MHz, $CDCl_3$) δ 161.4, 151.4, 150.8, 148.1, 135.8, 128.9, 128.7, 128.6, 127.6, 118.0, 111.7, 108.6, 102.4, 79.5, 36.6, 31.5, 30.9, 29.0, 22.6, 14.1. $R_f$: 0.7 (hexanes-ethyl acetate 90:10)

10-(hydroxymethyl)-6,6-dimethyl-3-pentyl-6H-benzo[c]chromen-1-ol (7)

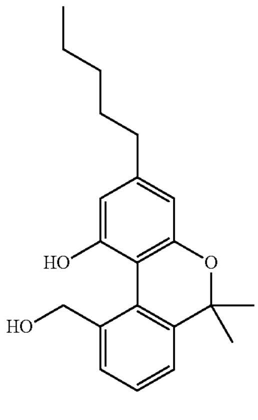 [SMILES: CCCCCc1cc(O)c2c(c1)OC(C)(C)c1cccc(CO)c1-2]

Figure 20:
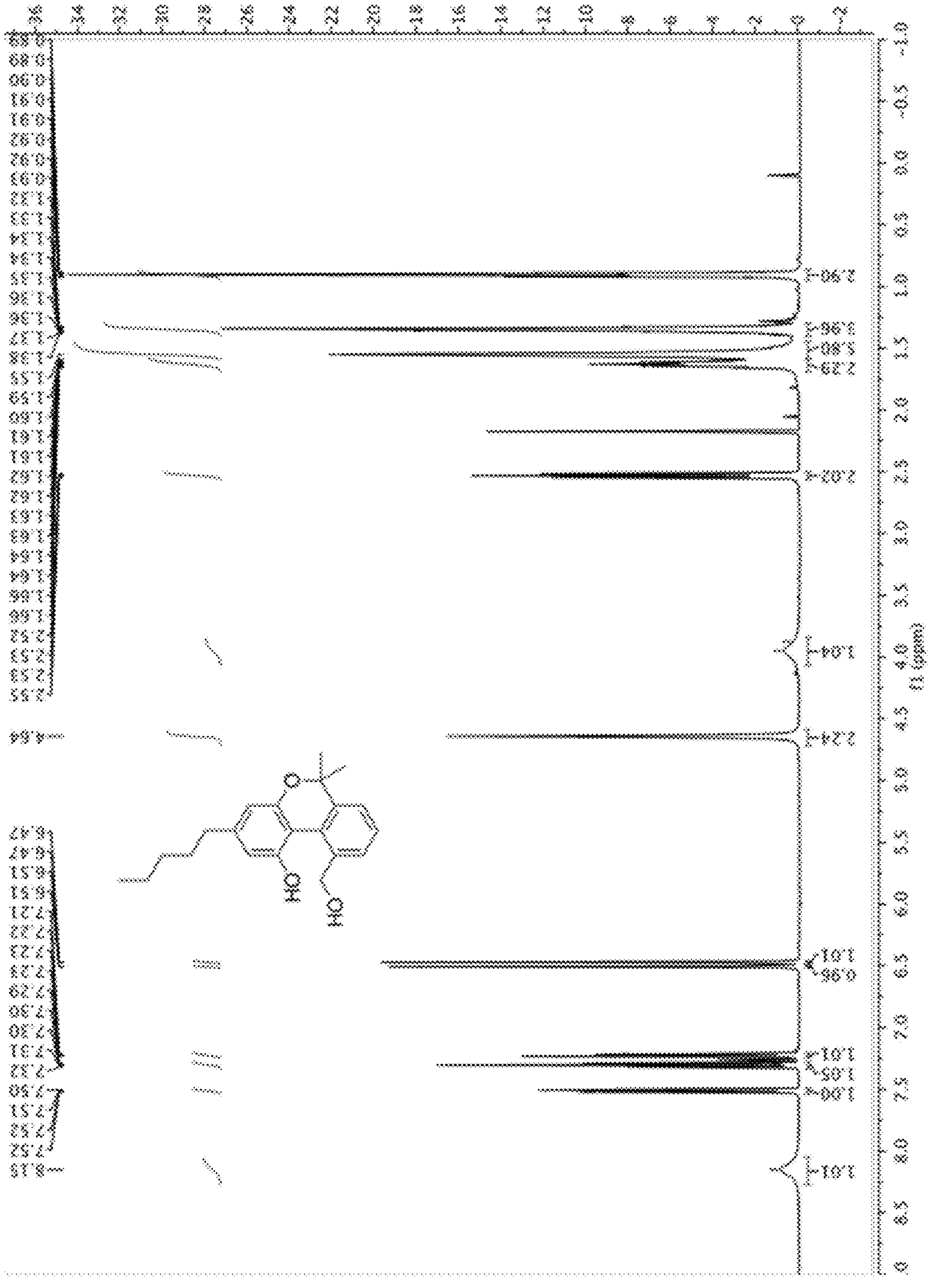
FIG. 20 shows a representative $^1$H NMR spectrum of a representative disclosed compound, 10-(hydroxymethyl)-6,6-dimethyl-3-pentyl-6H-benzo[c]chromen-1-ol, obtained using $CDCl_3$ as a solvent.
Figure 21:
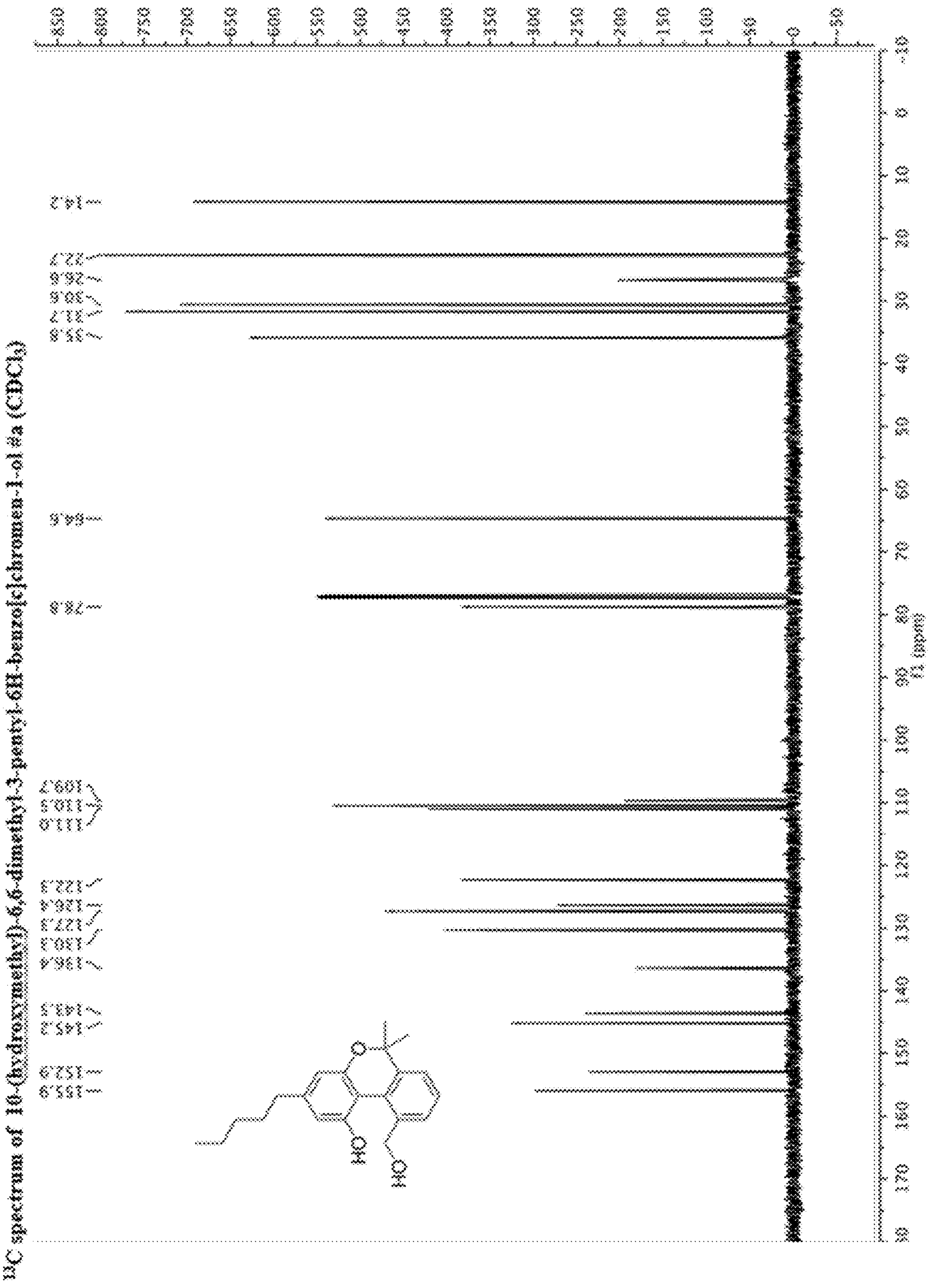
FIG. 21 shows a representative $^{13}$C NMR spectrum of a representative disclosed compound, 10-(hydroxymethyl)-6,6-dimethyl-3-pentyl-6H-benzo[c]chromen-1-ol, obtained using $CDCl_3$ as a solvent.
Figure 22:
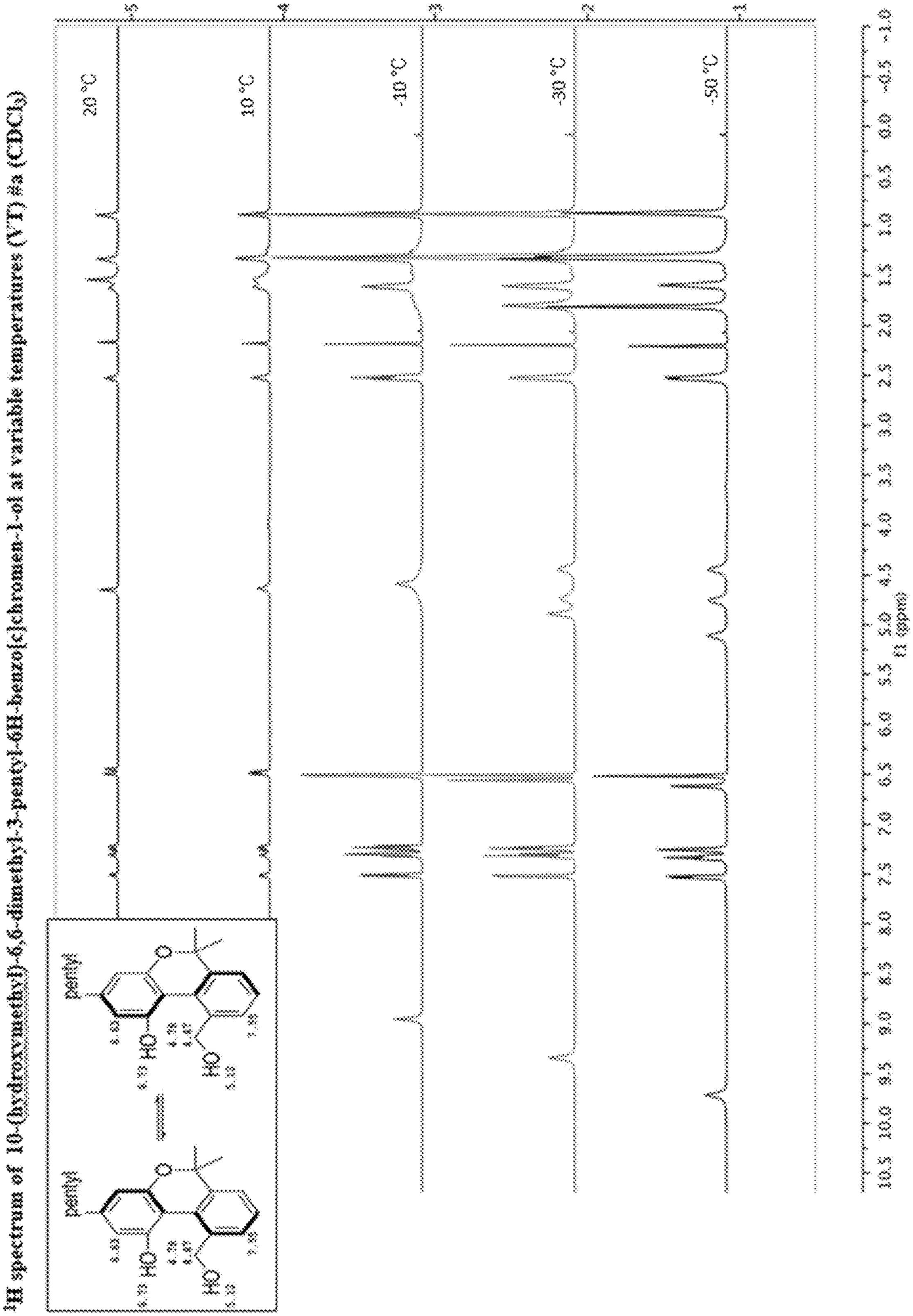
FIG. 22 shows a representative $^1$H NMR spectrum of a representative disclosed compound, 10-(hydroxymethyl)-6,6-dimethyl-3-pentyl-6H-benzo[c]chromen-1-ol, obtained using $CDCl_3$ as a solvent and at variable temperatures as indicated.

Obtained as a white solid, 1.8 g, 94%. $^1$H NMR (FIGS. 20 and 22) (500 MHz, $CDCl_3$) δ 8.15 (s, 1H), 7.51 (dd, J=7.7, 1.3 Hz, 1H), 7.30 (t, J=7.6 Hz, 1H), 7.22 (dd, J=7.7, 1.4 Hz, 1H), 6.51 (d, J=1.6 Hz, 1H), 6.47 (d, J=1.6 Hz, 1H), 4.64 (s, 2H), 3.95 (s, 1H), 2.53 (dd, J=8.8, 6.8 Hz, 2H), 1.63 (dq, J=9.4, 7.3 Hz, 2H), 1.55 (s, 6H), 1.35 (dq, J=7.4, 3.8, 3.3 Hz, 4H), 0.91 (t, J=6.8 Hz, 3H). $^{13}$C NMR (FIG. 21) (125 MHz, $CDCl_3$) δ 155.9, 153.0, 145.2, 143.6, 136.4, 130.3, 127.3, 126.4, 122.3, 111.0, 110.6, 109.7, 78.8, 64.6, 35.8, 31.7, 30.6, 26.6, 22.7, 14.1. $R_f$: 0.5 (hexanes-ethyl acetate 85:15)

(1-acetoxy-6,6-dimethyl-3-pentyl-6H-benzo[c]chromen-10-yl)methyl acetate

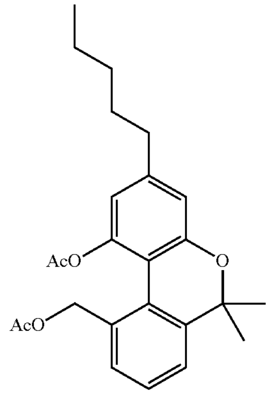 [SMILES: CCCCCc1cc(OC(C)=O)c2c(c1)OC(C)(C)c1cccc(COC(C)=O)c1-2]

Figure 23:
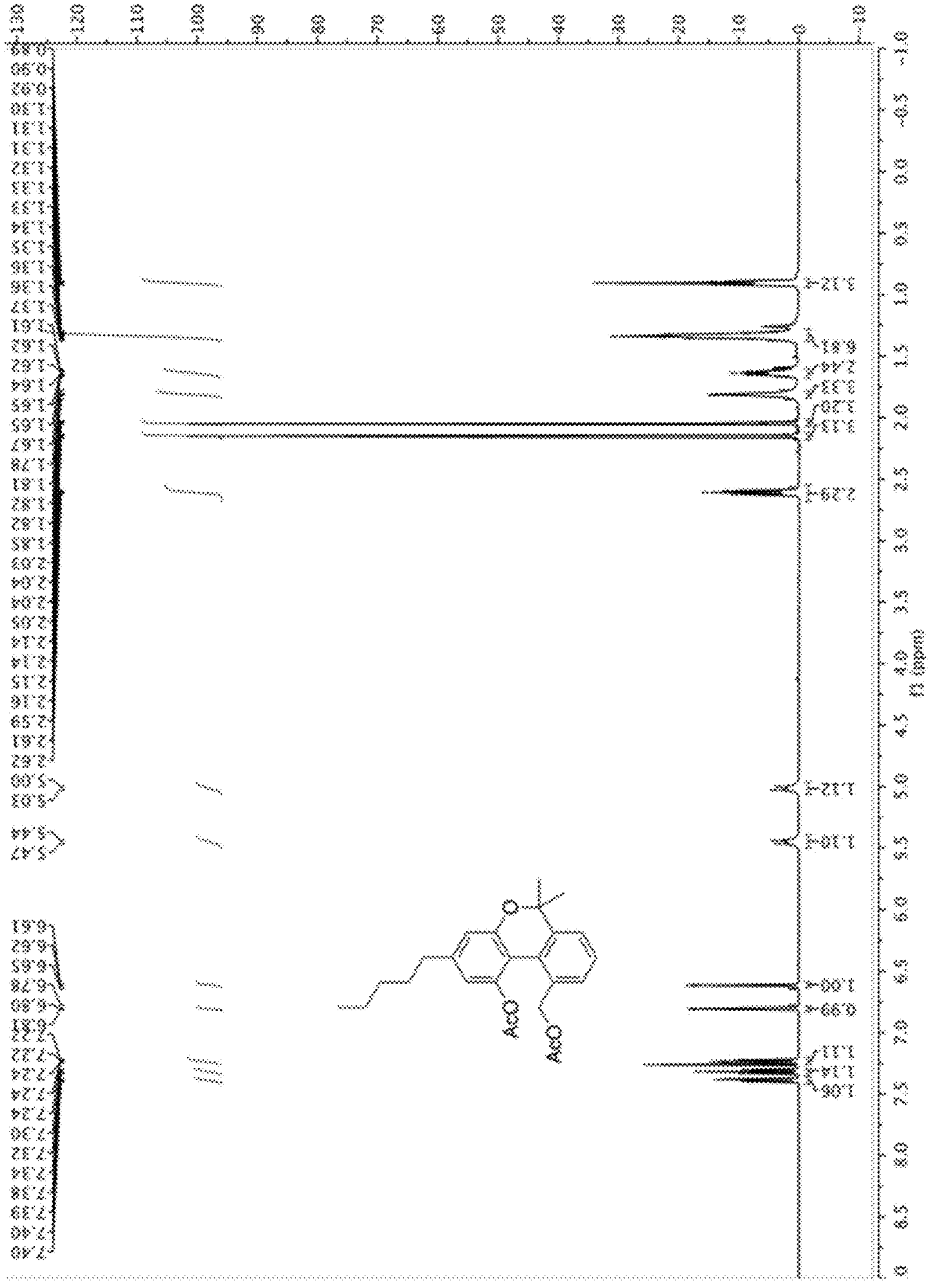
FIG. 23 shows a representative $^1$H NMR spectrum of a representative disclosed compound, 10-(hydroxymethyl)-6,6-dimethyl-3-pentyl-6H-benzo[c]chromen-1-ol, obtained using $CDCl_3$ as a solvent.
Figure 24:
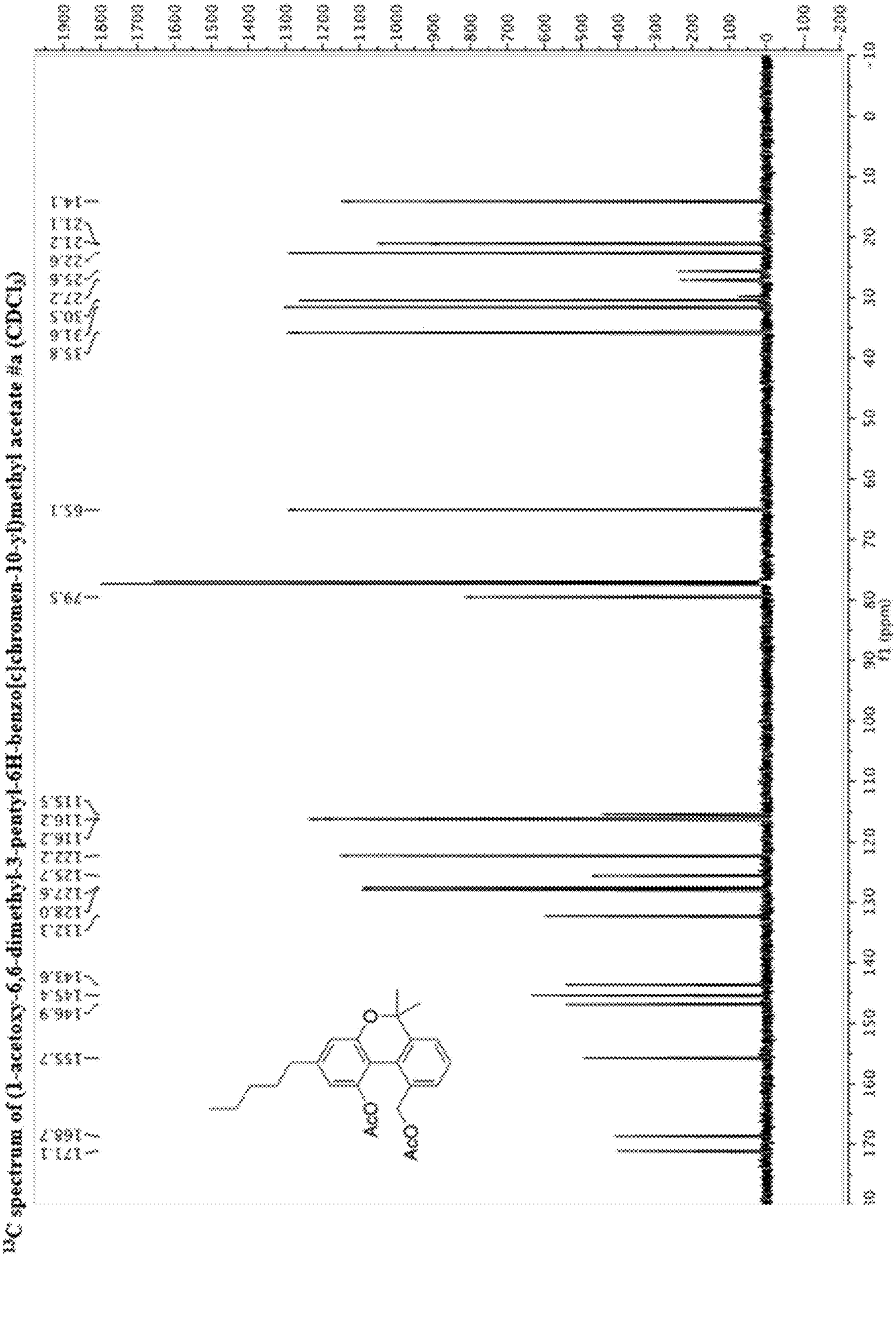
FIG. 24 shows a representative $^{13}$C NMR spectrum of a representative disclosed compound, 10-(hydroxymethyl)-6,6-dimethyl-3-pentyl-6H-benzo[c]chromen-1-ol, obtained using $CDCl_3$ as a solvent.

Obtained as a white solid, 29 mg, 87%. $^1$H NMR (FIG. 23) (500 MHz, $CDCl_3$) δ 7.39 (d, J=7.8 Hz, 1H), 7.32 (t, J=7.7 Hz, 1H), 7.23 (d, J=7.3 Hz, 1H), 6.81 (d, J=1.6 Hz, 1H), 6.62 (d, J=1.6 Hz, 1H), 5.45 (d, J=13.4 Hz, 1H), 5.01 (d, J=13.3 Hz, 1H), 2.60 (t, J=8.0, 7.6 Hz, 2H), 2.15 (s, 3H), 2.05 (s, 3H), 1.84-1.79 (m, 3H), 1.64 (p, J=7.4 Hz, 2H), 1.38-1.28 (m, 7H), 0.90 (t, J=6.9 Hz, 3H). $^{13}$C NMR (FIG. 24) (125 MHz, $CDCl_3$) δ 171.1, 168.7, 155.7, 146.9, 145.4, 143.6, 132.3, 128.0, 127.6, 125.7, 122.3, 116.2, 116.2, 115.5, 79.5, 65.1, 35.8, 31.6, 30.5, 27.2, 25.6, 22.6, 21.2, 21.1, 14.1. Re: 0.5 (hexanes-ethyl acetate 85:15).

Modular Assembly of Axially-Chiral Cannabinoids

Synthetic protocols to modularly assemble cannabinoids with previously inaccessible substitution patterns and structures: axially-chiral cannabinols (ax-CBNs). Without wishing to be bound by theory, ax-CBN and analogs thereof will provide unique opportunities for cannabinoid inspired drug discovery: whereas cannabinol (CBN) is a planar biaryl, ax-CBN and analogs thereof will bear significant three-dimensionality due to conformation restrictions resulting in novel atropisomeric (axially chiral) cannabinoid scaffolds, hence the name axially-chiral cannabinols.

Figure 6A:
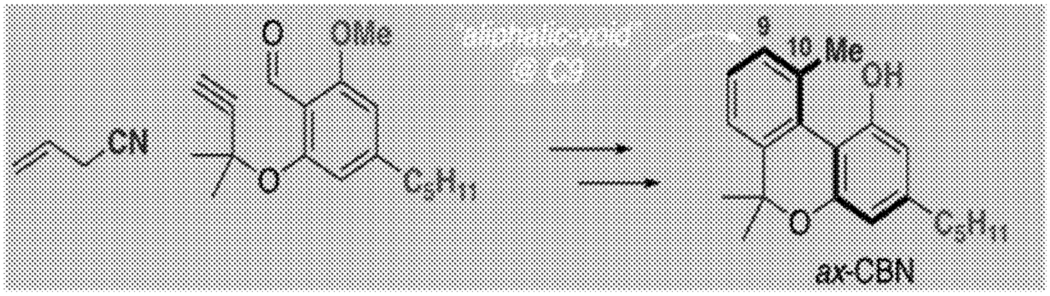
FIGS. 6A-6D show representative synthesis routes disclosed herein.
Figure 6B:
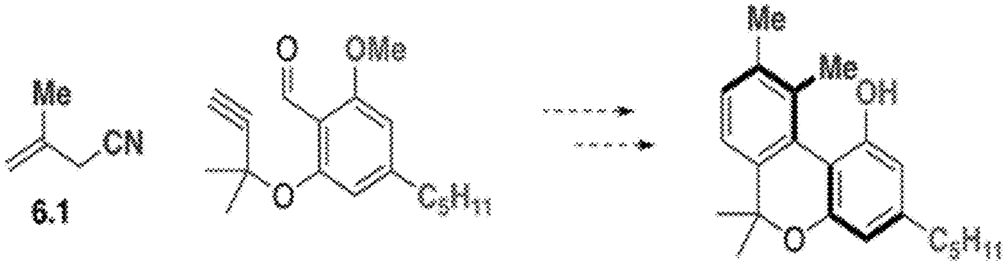
Figure 6C:
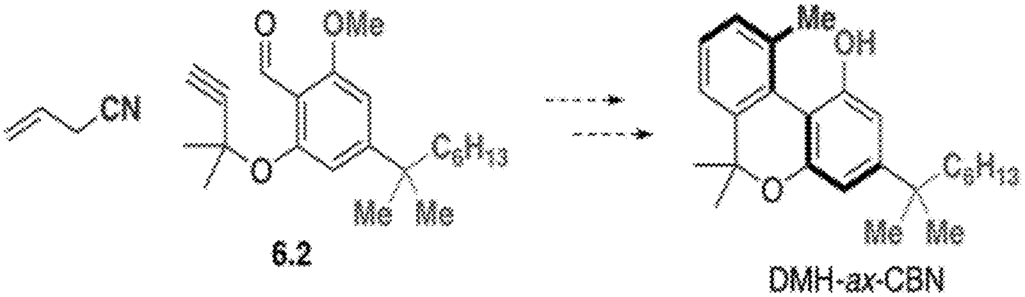
Figure 6D:
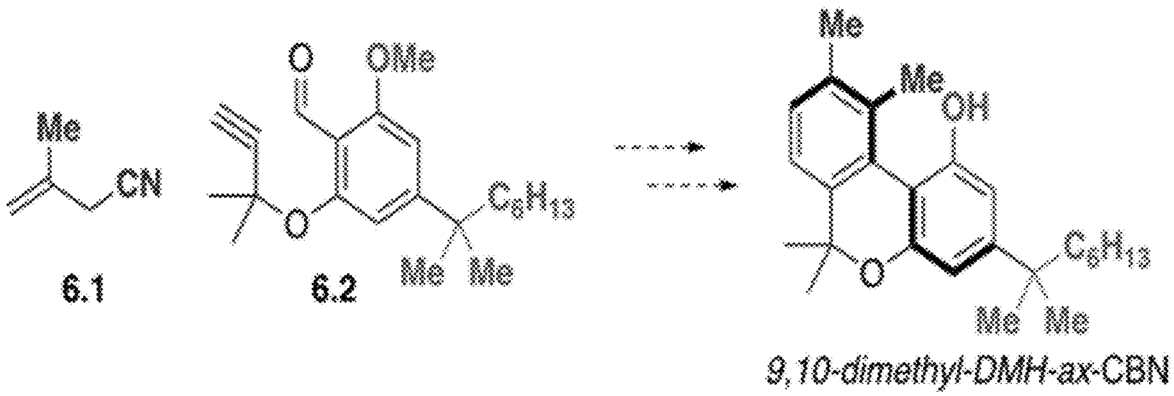

A few analogs can be synthesized via a convergent synthesis approach; by choosing other starting materials via the same sequence described in FIGS. 3A, 3B, 4, 5A, and 5B, analogs can be prepared. For example, in the design of ax-CBN, by moving the C9 methyl group to the C10 position, ground state three dimensionality is engendered, but an "aliphatic-void" is left at the C9 position (FIG. 6A). Thus, it is important to probe the structure-function of 9,10-dimethyl-ax-CBN (FIG. 6B). This can be prepared from 2-methylallylnitrile 6.1. In the phytocannabinoid analog literature, the dimethylheptyl (DMH) group is a standout structural modification; there are hundreds of synthetic cannabinoids with this change that have improved potency or selectivity in cannabinoid receptor binding. Thus, from the DMH-containing salicylaldehyde-derivative 6.2 via the standard sequence, DMH-ax-CBN can be prepared (FIG. 6C). Finally, by taking both of the unique starting materials, 2-methylallyl nitrile 6.1 and the DMH-containing salicylaldehyde-derivative 6.2, a fourth analog, 9,10-dimethyl-DMH-ax-CBN can be prepared (FIG. 6D). These first four analogs can be used to benchmark the activity of ax-CBNs as they bear the most similarity to phytocannabinoids and phytocannabinoid analogs. Compared to CBN, THC, and related analogs, the unique differences of ax-CBNs in FIGS. 6A-6D are (a) their three-dimensionality, provided by the conformationally restricted biaryl, and (b) the hypothesized increase in stability due to the targets having biaryl structure.

Figure 8A:
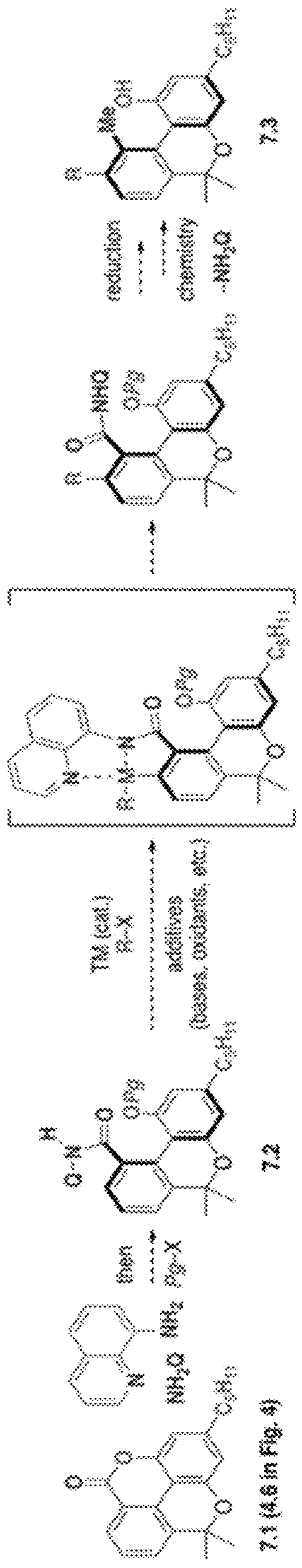
FIGS. 8A-8B show a representative disclosed synthesis and compounds prepared using the same.
Figure 8B:
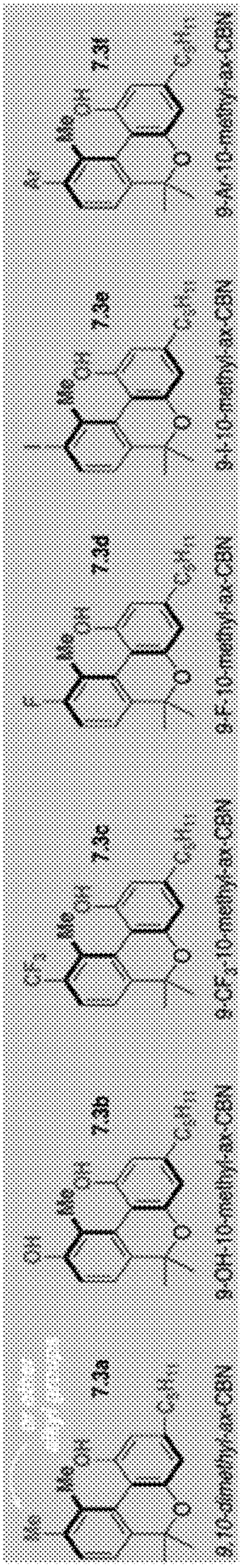
Figure 9A:
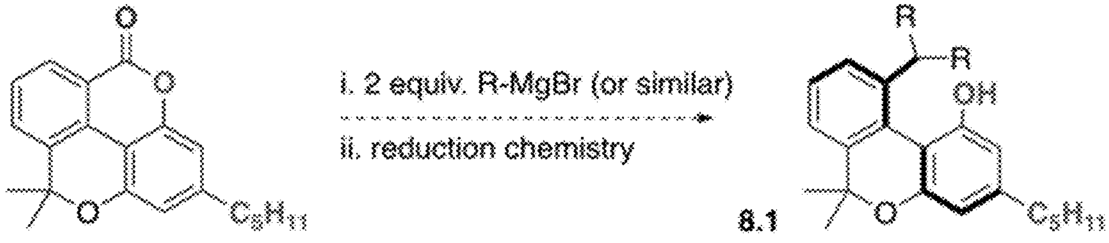
FIGS. 9A-9C show representative disclosed divergent syntheses of representative disclosed biaryl cannabinoid analogs.
Figure 9B:
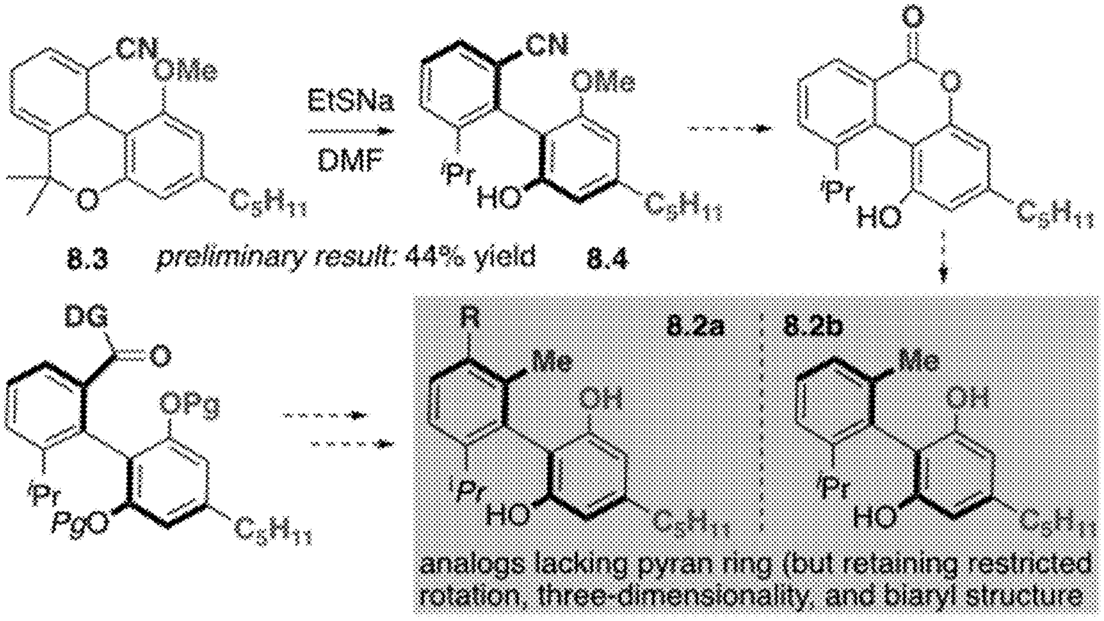
Figure 9C:
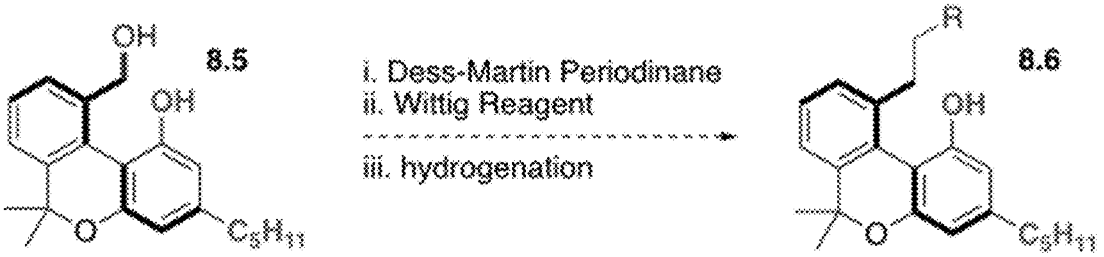

From the foregoing, a few intermediates arise as attractive points of divergence (FIGS. 8A-8B). For example, the lactone 7.1 can be of particular interest. By reacting this intermediate with an 8-aminoquinoline, or one of many other plausible directing groups, followed by alcohol protection, we will arise at a substrate 7.2 that can undergo robust and diverse directed $C^9$—H functionalization. Thus, we will prepare a variety of C-9 substituted ax-CBNs 7.3 by catalytic C—H functionalization then reduction of the amide to the C10 methyl group. For example, this could be an alternative protocol for synthesizing 9,10-dimethyl-ax-CBN or other 9-alkylated ax-CBNs (7.3a). Hydroxylation (7.3b) would be of interest considering that some successful THC-analogs, such as Nabilone, bear C-9 oxygenation. Preparing trifluoromethylated (7.3c) or fluorinated (7.3d) variants would be of value considering the impact that fluorination has on physical properties and drug metabolism (ADMET). Iodination (7.3e) is useful, considering the synthetic value of aryl iodides. As a final example, directed arylation can be performed. This technology yields interesting bis-biaryl cannabinoid analogs (7.3f).

In addition to using the lactone for installation of a directing group for $C^9$-selective C—H functionalization (FIGS. 6A-6D), the lactone can be reacted with a variety of organometallics followed by alcohol reduction to yield ax-CBNs with a variety of C-10 groups (FIGS. 6A-6D). These analogs in FIGS. 9A-9C (8.1) have the potential to alter the dihedral angle and barrier to atropisomerism due to increased sterics. A variety of other intermediates from the route are attractive points of divergence (FIG. 6B-6D). Based on preliminary data, a small collection of analogs 8.2a-b lacking the pyran ring can be prepared, but retaining the other unique features (restricted rotation, ground state three-dimensionality, hypothesized stability, biaryl scaffold). During the development of our route to ax-CBN (FIGS. 3A, 3B, and 4), it was determined that the Diels-Alder product 8.3, when treated with the sodium ethanethiolate (NaSEt), undergoes a tandem C—O cleavage/aromatization reaction to yield the biaryl 8.4. The disclosed reaction can be further optimized and via analogous routes as described in FIGS. 3A, 3B, 4, and 6A-6D, prepare biaryl analogs 8.2a-b. The benzylic alcohol-containing substrate 8.5 (formerly 4.7) is also an attractive substrate for divergence (FIG. 6C). We surmise that oxidation to the benzaldehyde followed by Wittig olefination and hydrogenation would also yield unique C-10 alkyl groups (8.6).

There were other notable observations uncovered during the multi-step route development as seen below in and in FIG. 3C. Notably, cyano-THC (9.1) in the presence of thiolate yielded aromatized products 9.5 and 9.6 as separable products. Mechanistically, 9.1 in the presence of NaSEt, could form an anion intermediate 9.2 which could react in two different pathways. In one pathway, 9-des-methyl-CBN 9.5 could be delivered via diene isomerization and subsequent dehydrocyanation or the novel axially chiral biaryl 9.6 could be constructed via pyran ring opening, phenoxide protonation and double bond isomerization. These preliminary results present an opportunity to access other unique cannabinoid-based biaryl analogues.

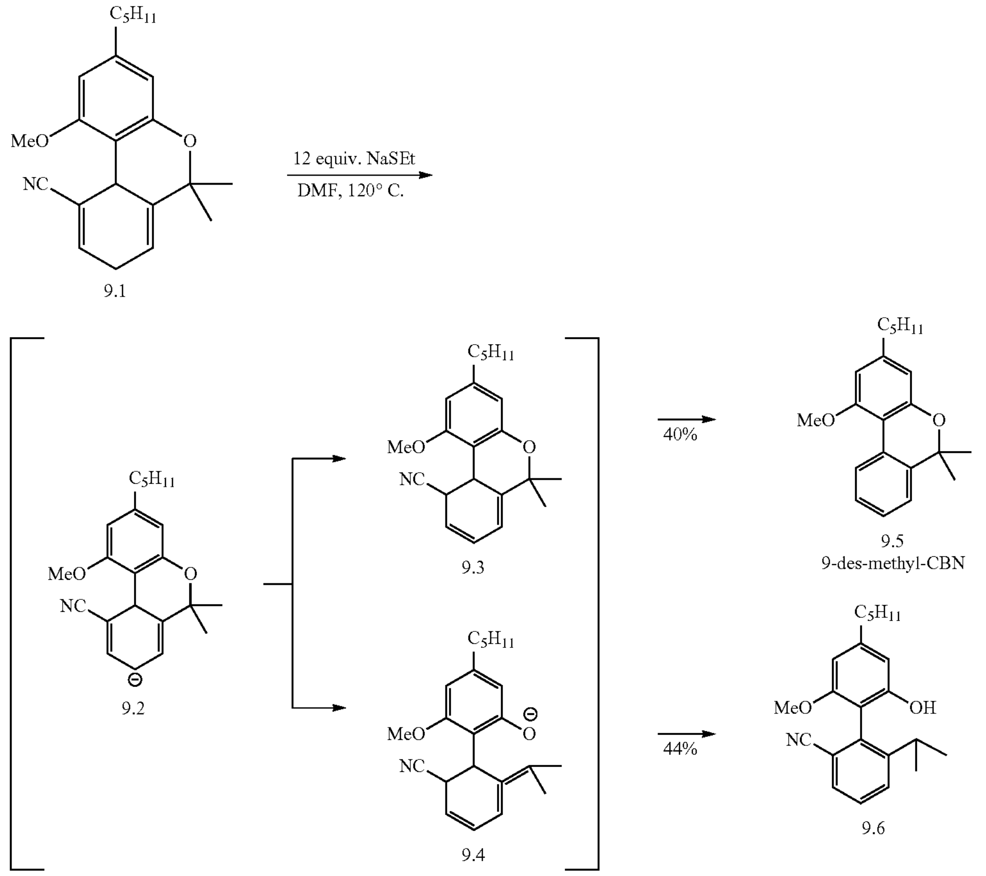

Example Extended Modular Synthesis

Figure 3A:
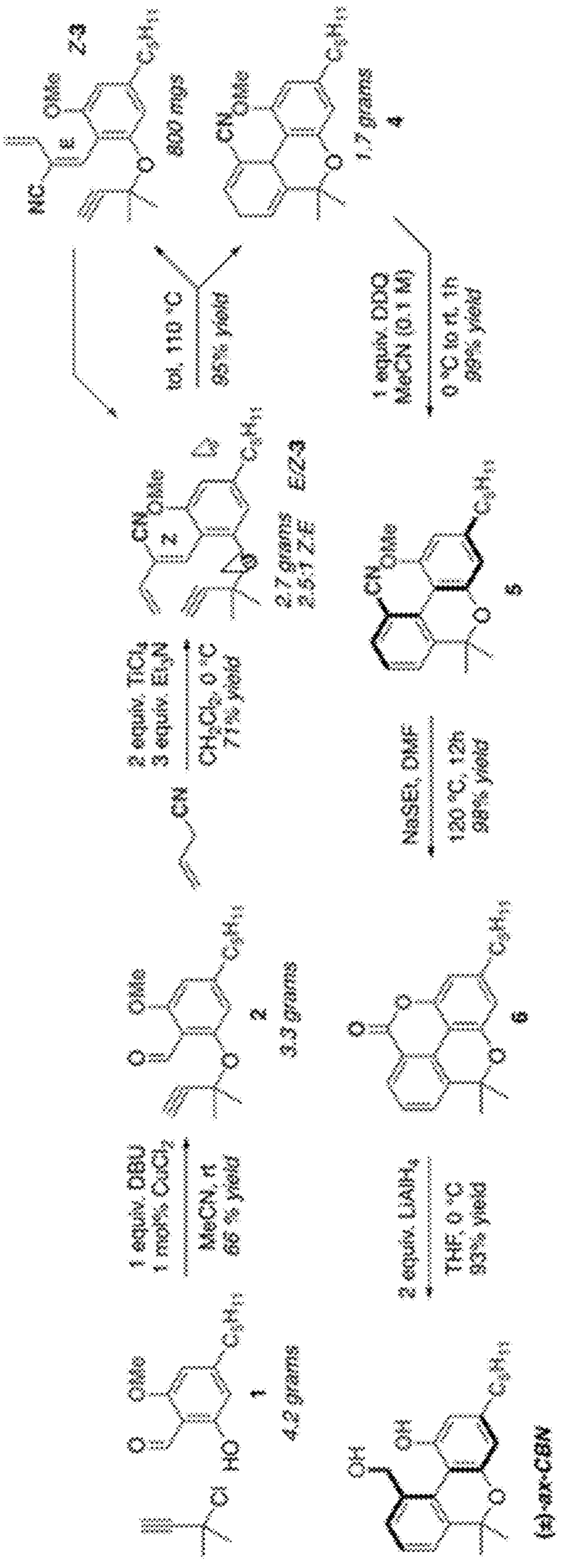
FIG. 3A shows a representative disclosed synthesis showing the usefulness of (E)-alk-3-enenitriles in the disclosed methods of preparing substituted axially-chiral cannabinols.
Figure 3B:
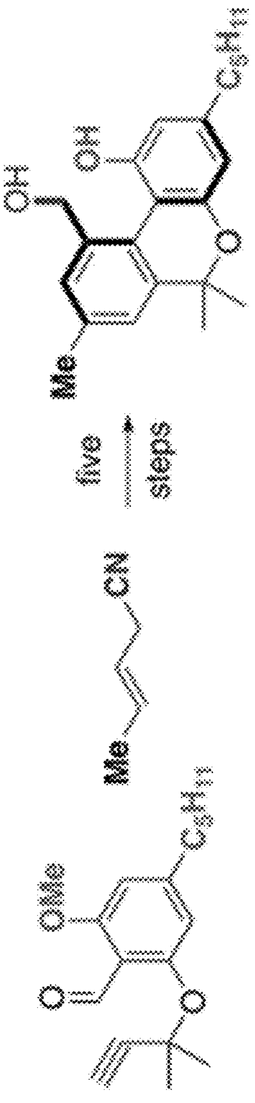
FIG. 3B shows a representative synthesis with a substituent on the 8 position of the benzopyran ring.
Figure 3C:
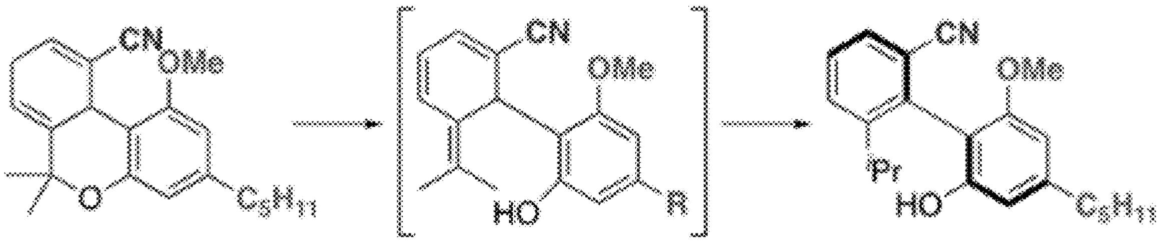
FIG. 3C shows a representative disclosed reaction sequence that shows that a disclosed intermediate can be diverted to various representative disclosed axially chiral biaryl compounds.
Figure 4:
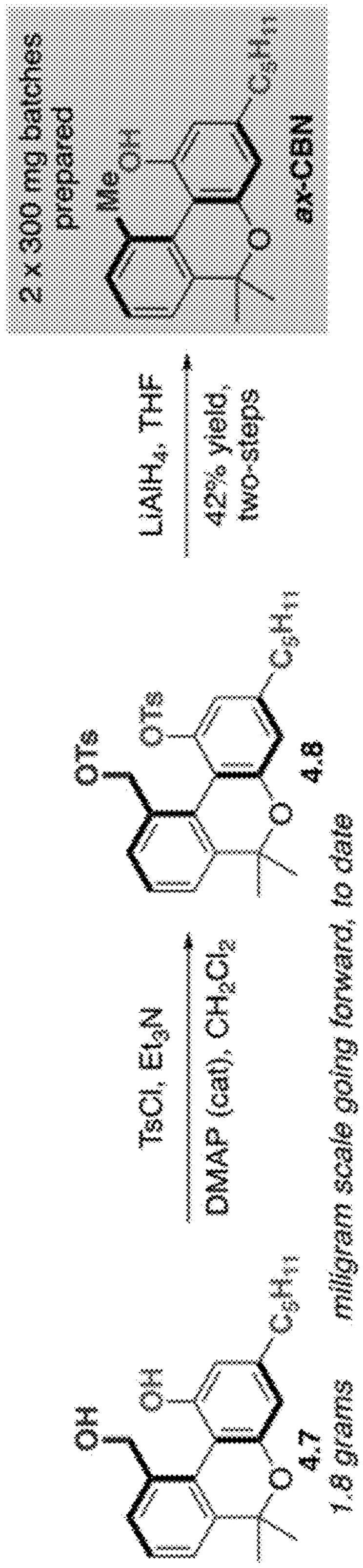
FIG. 4 shows a scalable additional series of steps that can be performed following the reaction of FIG. 3A to post-synthetically modify the substituent at the 10 position of the benzopyran ring. Together with FIG. 3A, these steps represent a total synthesis of an ax-CBN of the present disclosure.
Figure 5A:
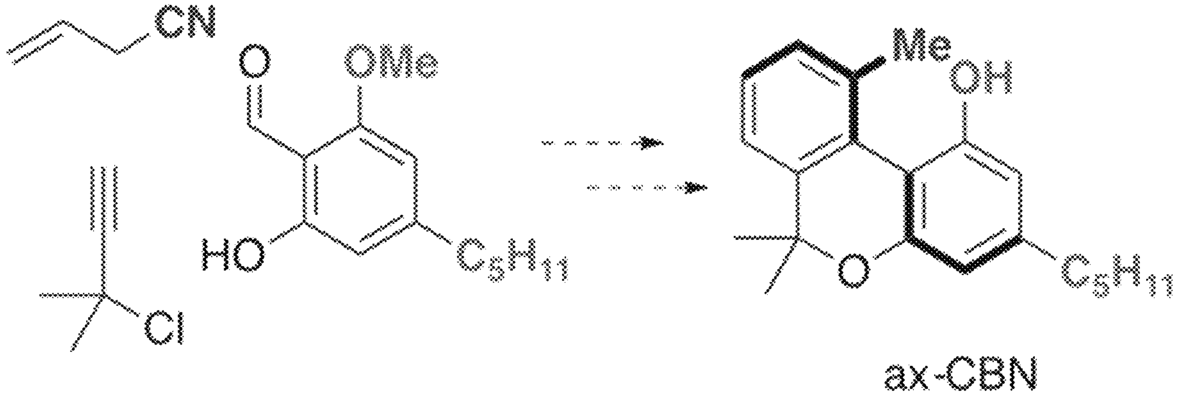
FIGS. 5A-5B show generalized disclosed synthetic schemes.
Figure 5B:
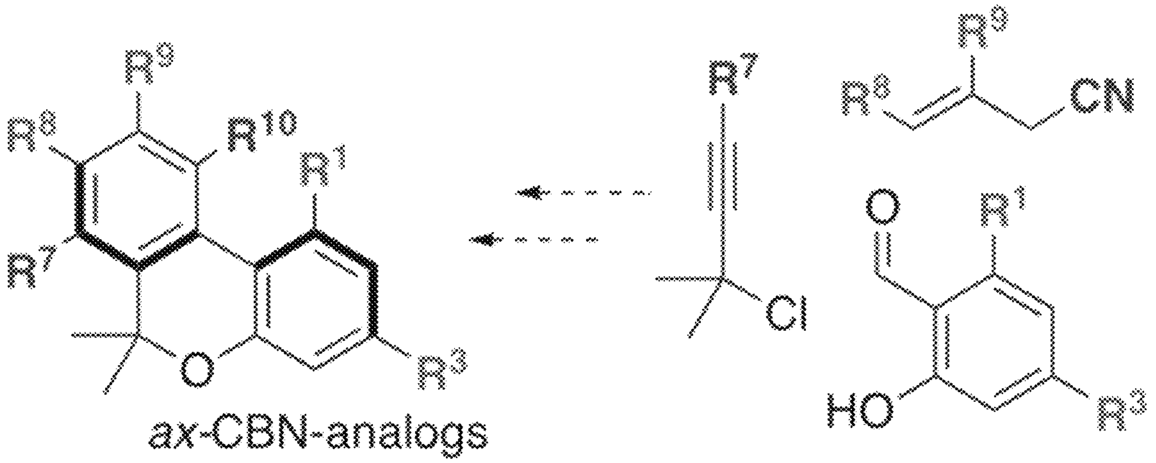

Disclosed herein is 8-step, gram-scale route ax-CBN (see FIGS. 3A, 3B, and 4). Salicylaldehyde 1 can react with 1,1-dimethylpropargyl chloride via copper-catalysis to yield the phenyl propargyl ether 2. $Et_3N/TiCl_4$-mediated aldol condensation yields an inseparable 2.5:1 mixture of Z:E dienes 3. Only the Z-diene reacts via Diels-Alder cycloaddition to yield the dihydrobenzochromene scaffold 4, which is oxidized with DDQ to yield the biaryl 5. The achiral and planar lactone (±)-ax-CBN is established by ethanethiolate-promoted demethylation and intramolecular Pinner reaction. In a straightforward three-step reductive sequence, the lactone is converted to the target ax-CBN by $LiAlH_4$ reduction (4.7), diol activation to the bis-tosylate 4.8, then benzylic reduction. To date, we have prepared multigrams of advanced intermediates and ~600 mgs of ax-CBN. This initial batch of ax-CBN was enough to obtain promising preliminary data on analgesic properties.

Figure 25A:
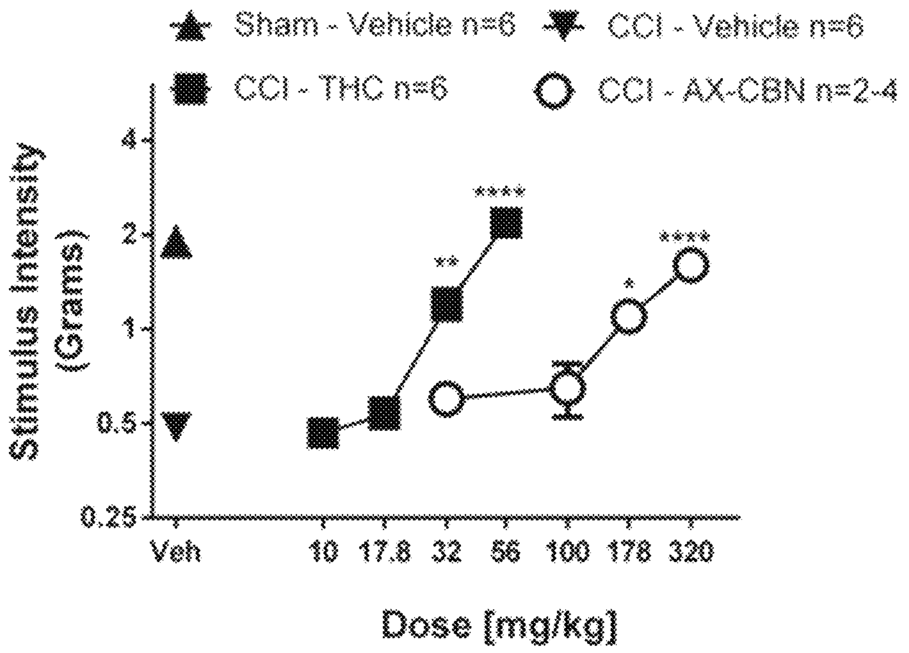
FIG. 25A shows representative in vivo work using ax-CBN versus THC and demonstrating that ax-CBN has a more favorable dosing window than THC; data were obtained in Sham or CCI-surgerized mice which were then tested for mechanical allodynia.
Figure 25B:
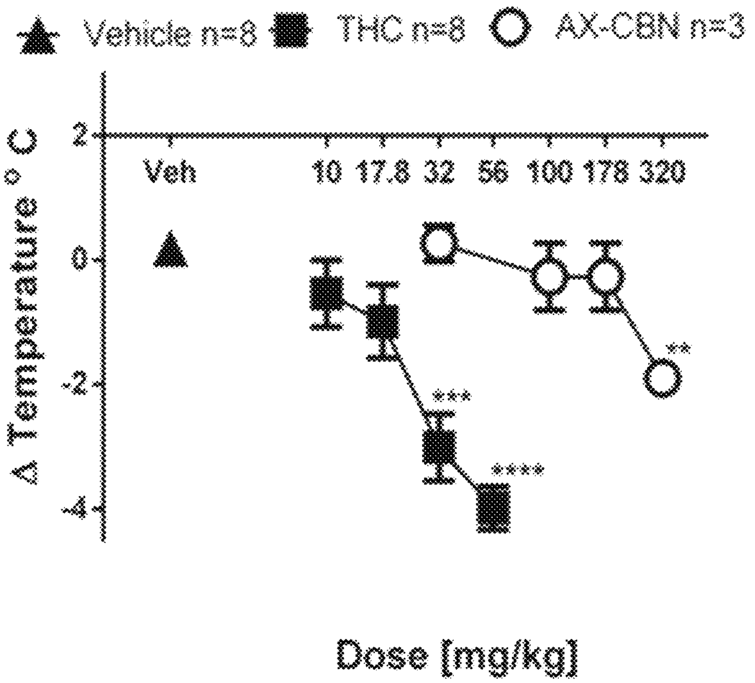
FIG. 25B shows data for a separate cohort of mice tested for changes in body temperature.
Figure 25C:
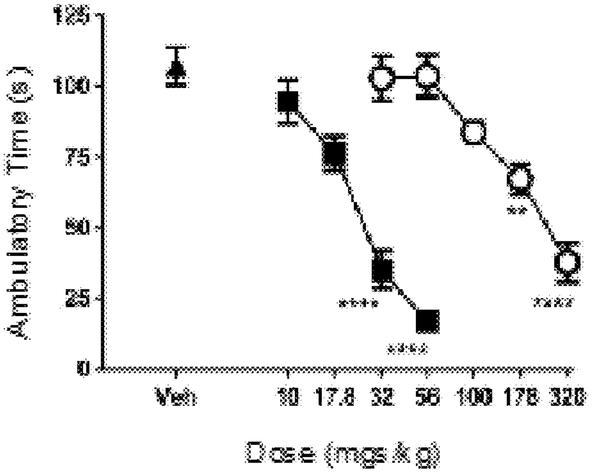
FIG. 25C shows locomotion measured as ambulatory time for a cohort of mice dosed as disclosed above.
Figure 26A:
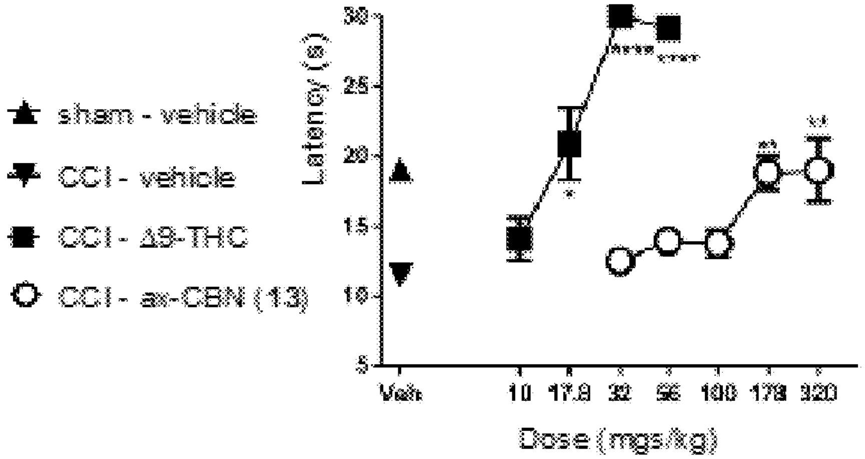
FIG. 26A shows representative data for neuropathic pain-induced thermal hyperalgesia, measured as latency in seconds to respond.
Figure 26B:
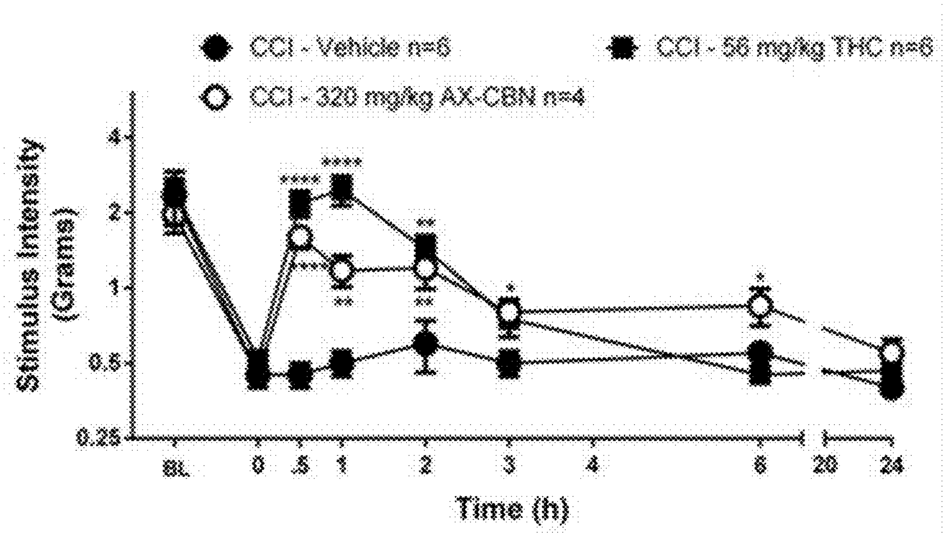
FIG. 26B shows representative data from the same mice as in FIG. 25A after testing for reversal of mechanical allodynia to 24 h post-administration. (Mean±SEM of 2-8 mice/point,  $p<0.01$, * $p<0.001$, **** $p<0.0001$ versus vehicle control groups.)
Figure 27A:
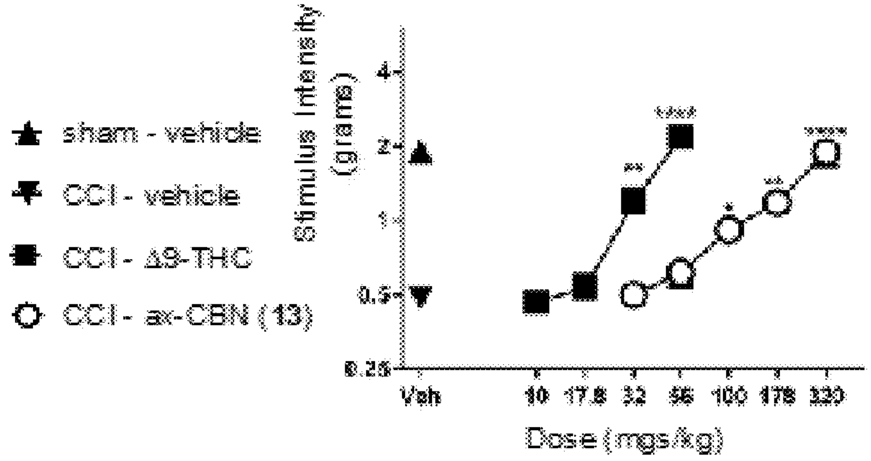
FIGS. 27A-B show representative data for neuropathic pain-induced mechanical allodynia measured as grams of THC or ax-CBN required to produce a stimulus response.
Figure 27B:
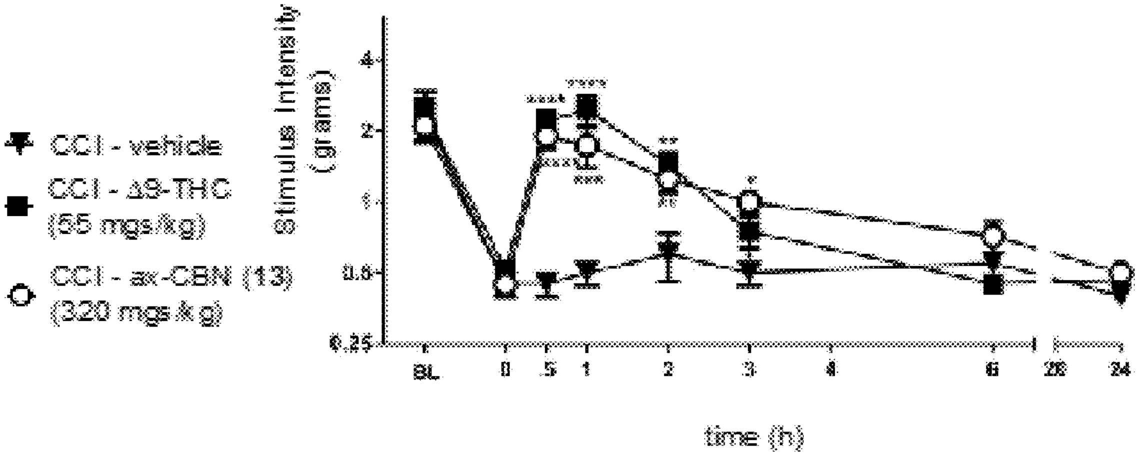
Figure 28:
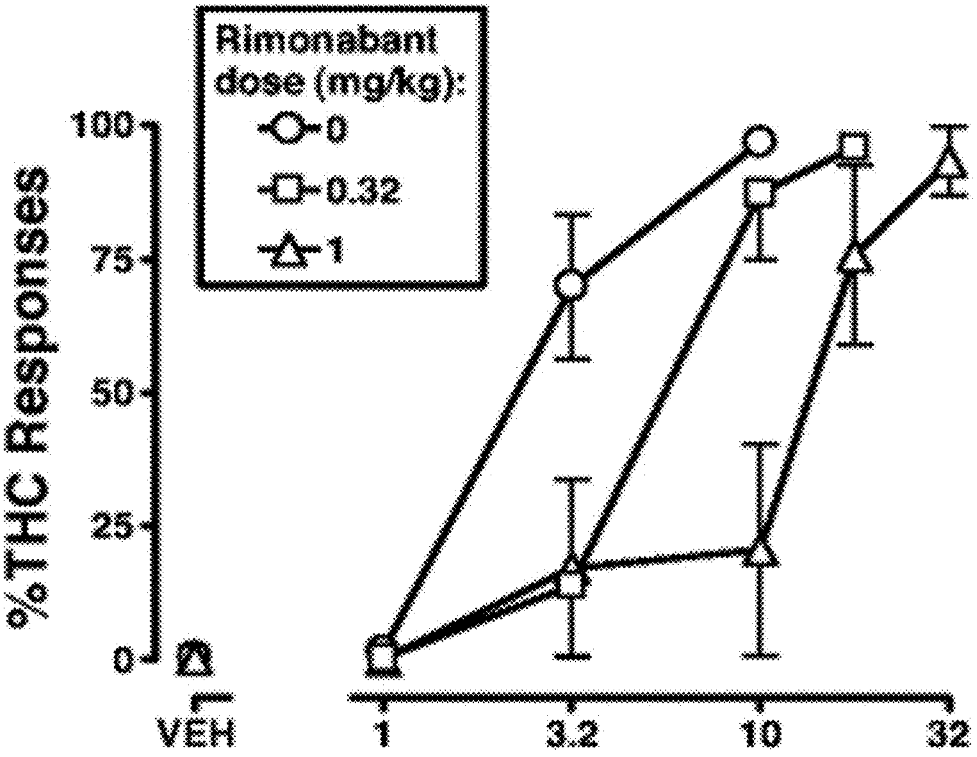
FIG. 28 shows a plot of stimulus intensity overtime in hours.

Preliminary studies were conducted in C57bl/6j mice to examine the analgesic effects of ax-CBN, as compared to THC. Mice underwent the chronic constriction injury of the sciatic nerve (CCI) or sham surgery. After 7 days post-surgery, vehicle or compound was administered, and mice were tested for a behavior associated with neuropathic pain: mechanical allodynia, i.e., increased sensitivity to non-nociceptive light touch via the von Frey assay. In a separate cohort of C57bl/6j mice the same doses of ax-CBN and THC were examined in the reduction of body temperature, an effect considered here to be unwanted or adverse. FIG. 25A demonstrates that ax-CBN and THC administered systemically dose-dependently reverse mechanical allodynia. FIG. 25B demonstrates that THC produces robust depression of body temperature; ax-CBN also decreases body temperature, but the magnitude of decrease up to the largest dose studied is less than that produced by THC. FIG. 26B demonstrates the time course of ax-CBN and THC in the reversal of CCI-induced mechanical allodynia. FIG. 25C shows locomotion measured as ambulatory time. Table 1 (below) summarizes the $ED_{50}$ of ax-CBN and THC in reversing mechanical allodynia and decreasing body temperature, as well as the potency ratio of each drug for these two measures. Ax-CBN produces reversal of mechanical allodynia at a ~2-fold lower dose than required to produce decreases in body temperature. Meanwhile, THC is relatively equipotent to produce effects in both measures. This demonstrates that ax-CBN has a more favorable therapeutic dosing window than THC.

TABLE 1

$ED_{50}$ of Cannabinoids in Reversing Mechanical Allodynia and Decreasing Body Temperature

| | ax-CBN | THC |
|---|---|---|
| Allodynia $ED_{50}$ ((95% CL) mg/kg) | 170.0 (122.0-237.0) | 29.9 (26.3-34.0) |
| Body Temp. $ED_{50}$ ((95% CL) mg/kg) | 318.4 (250.5-404.6) | 21.2 (12.0-37.3) |
| Potency Ratio (Temp./Allodynia) | 1.9 (1.7-2.1) | 0.7 (0.5-1.1) |

Although each of the eight reactions perform well enough to access material, the disclosed steps can be further optimized. For example, the condensation reaction to yield the diene is problematic in that a Z/E diene mixture is obtained. Only the Z-diene proceeds toward ax-CBN and the E-diene is sacrificed. In FIG. 3A, about 1 gram of material is lost to the E-diene. Another series of steps that can be optimized is the final sequence. The benzylic reduction takes two steps and only 42% yield is achieved. This can be done more efficiently either by decreasing the step count (directly convert the benzyl alcohol moiety the methyl benzene) or by further optimizing the current protocol. Once these synthetic bottlenecks are addressed, multigrams of ax-CBN can be made in a short amount of time.

The physical properties of ax-CBN can be characterized, including (1) its ground-state structure (2) barrier to atropisomerism, and (3) and bench stability. Based on in silico calculations and variable-temperature NMR studies, ax-CBN has a barrier to atropisomerism of ~17 kcal·mol$^{-1}$ and a ground state dihedral angle of 38°. The ~17 kcal·mol$^{-1}$ tells us that the atropisomers are rapidly interconverting at room temperature whereas the ground state structure infers that the molecule has significant three-dimensionality in the ground state. Thus, at the moment, there is no need to target a single enantiomer as the atropisomers are rapidly interconverting.

Interestingly, this implies that the rapidly interconverting atropisomers will bind the target with different affinities: a dynamic-kinetic resolution at the protein/receptor. In other words, the receptor-ax-CBN atropisomer complexes are diastereomeric (different energies). Docking studies of ax-CBN (and analogs, vide infra) can be performed with $CB_1$, $CB_2$, or other proteins/receptors that may be of interest. Efforts to compute the ground-state structure of ax-CBNs were previously described. This information, along with the known crystal structure data for $CB_1$ and $CB_2$, can be used to rationally design analogs of ax-CBN (ax-CBNs).

Preliminary data supports that ax-CBNs are be easily accessible via the disclosed synthetic protocol. The disclosed methods can provide specific (FIGS. 6A-6D) and diverse (FIGS. 8A-8B and 9A-9C) analogs to probe the activity of ax-CBNs to cannabinoid-inspired drug discovery. However, by optimizing the chemistry as described herein, it will be possible to prepare a wide variety of cannabinoid analogs with unique three-dimensional ground state biaryl structure.

The studies disclosed herein provide new and accessible methods to a three dimensional biaryl platform (axially-chiral cannabinoids, ax-CBNS) for cannabinoid-inspired drug discovery. The disclosed methods provide a facile approach to accessing the ax-CBN scaffolds, scalable and practical methods for synthesis of ax-CBN and a variety of disclosed ax-CBN analogs. The disclosed ax-CBN and analogs can be validated as cannabinoid receptor ligands via the in vivo and in vitro studies as described herein.

In Vitro Assays

The in vitro cannabinoid receptor binding affinities of the parent ax-CBN and ax-CBN analogs (ax-CBNs) can be assayed and these molecules can be further examined in pre-clinical models of antinociceptive/hypothermic effects, as well as in a well-validated model of $CB_1$ receptor-mediated subjective effects. The in vitro cannabinoid binding affinity of novel chemical entities in cultured HEK293 cells stably expressing either human $CB_1$ or $CB_2$ receptor subtypes can be established and the in vivo cannabinoid activity of novel chemical entities can be identified. First, a pre-clinical model of neuropathic pain, i.e., the chronic constriction injury (CCI) of the sciatic nerve in C57BL/6J mice can be used to screen for effectiveness to produce reductions in pain-evoked mechanical allodynia. Second, drug-induced hypothermia, a well-known effect of $CB_1$ receptor agonists in C57BL/6J mice, can be examined. Third, a pre-clinical model of subjective effects, i.e., C57BL/

6J mice discriminating 5.6 mg/kg THC (i.p.), can be used to screen for $CB_1$ receptor agonist activity. Receptor activity can be further evaluated with the $CB_1$ receptor-selective antagonist rimonabant and the $CB_2$ receptor-selective antagonist SR 144528.

Figure 2A:
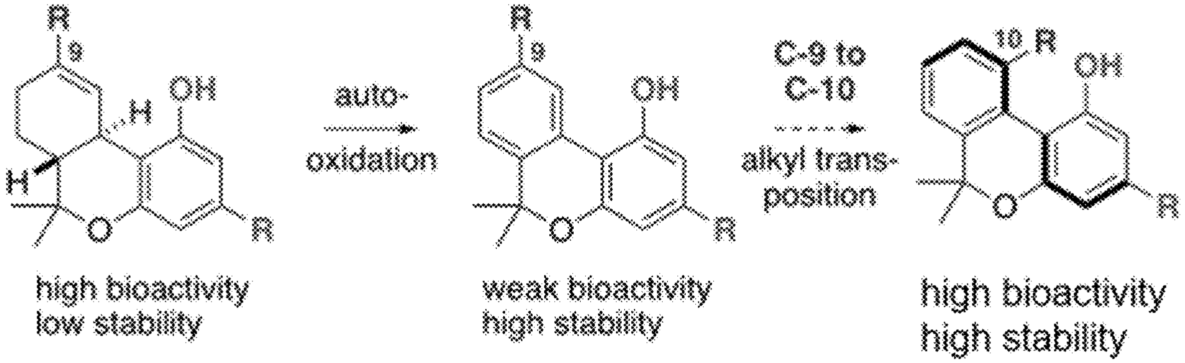
FIGS. 2A-2F show aspects of planar and three-dimensional structure pertaining to the disclosed synthetic routes and compounds.
Figure 2B:
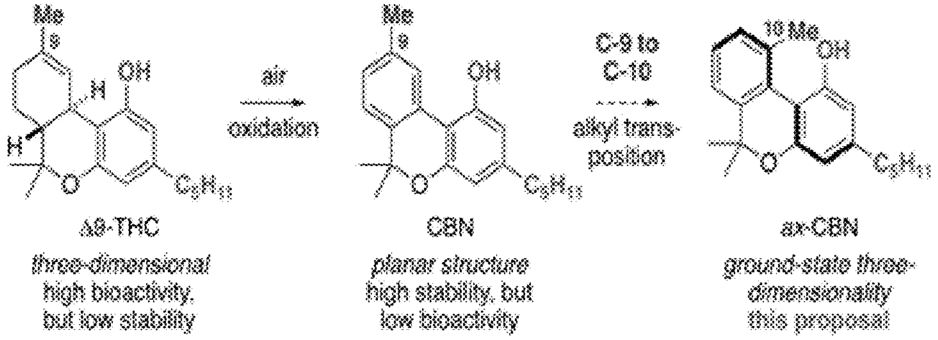
Figure 2C:
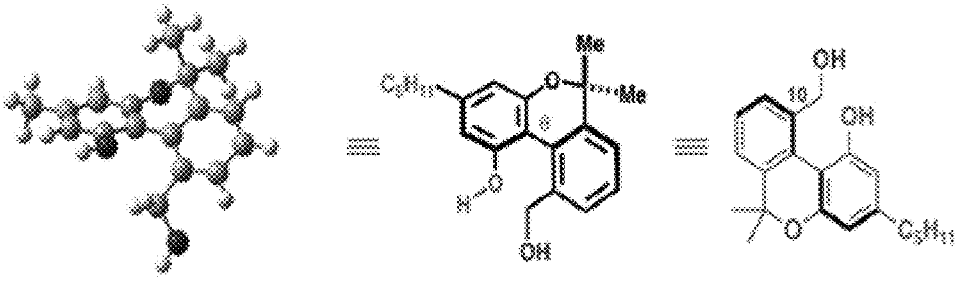
Figure 2D:
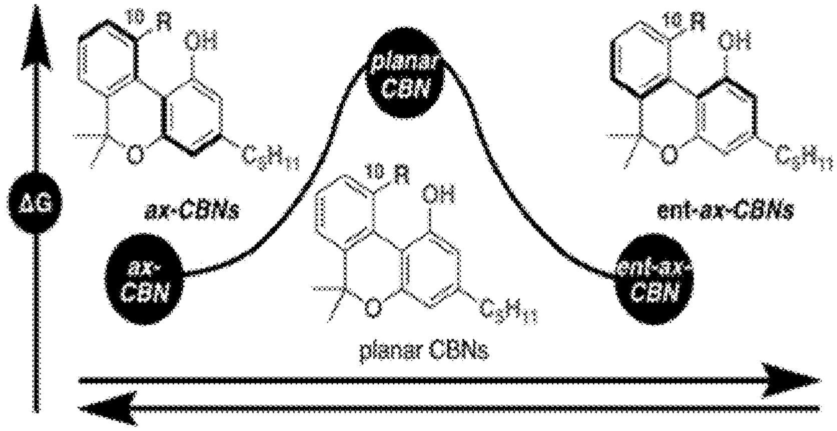

10-methyl-CBN, referred to as "ax-CBN" in the present disclosure is an unnatural isomer of CBN that is believed to have distinct properties from natural CBN, due to a dramatically different ground-state structure; drug structure=drug function. Ax-CBNs can exhibit atropisomerism/axial-chirality in their ground state, which has yet to be explored in cannabinoid-inspired drug discovery, hence the name ax-CBN. In preliminary computational studies, the ground state structure of CBN is ~planar-biaryl whereas ax-CBN has significant three-dimensionality (θ=38°) with a barrier to atropisomerism of 17 kcal·$mol^{-1}$ (FIGS. 2A-2C). As a further comparison, the analogous bonds of THC have a dihedral angle of θ=45°. Thus, it is possible to mimic the three-dimensional shape of THC with axially-chiral cannabinols. As shown in FIG. 2D, whereas CBN is planar in its ground state, ax-CBNs will be three-dimensional in their ground state.

In addition to the dramatic changes in structure that the C-9-to-C-10 methyl transposition can cause (CBN vs. ax-CBN), it is believed that because ax-CBN is a biaryl molecule, it can have increased stability compared to THC. The disclosed methods for preparing the disclosed compounds are believed to comprise the stability of natural CBN and the advantages of the disclosed biaryl structures. That is, in view of how commonplace biaryls are in drug discovery: biaryl motifs are often targeted because they are synthetically accessible by robust chemistry and have attractive ADMET properties, including metabolic and aerobic stability. The disclosed methods to prepare the disclosed compounds provide distinct scaffolds for phytocannabinoid-based drug discovery.

Cell culture Human Embryonic Kidney Cells (HEK293) expressing either the human $CB_1$ or $CB_2$ receptor will be cultured at 37° C. Membranes will be prepared by homogenization and centrifugation and stored at −80° C. until use. [$^3$H]CP55.940 binding Membranes will be incubated with 1 nM [$^3$H]CP55,940 and varying concentrations of a test compound. Non-specific binding will be measured in the presence and absence of 5 μM SR141716A ($CB_1$) or 10 μM WIN55,212-2 ($CB_2$). [$^{35}$S]GTPγS binding Membrane samples will be thawed on ice, centrifuged, incubated with 10 μM GDP, 0.1 nM [$^{35}$S]GTPγS, and various concentrations of a test compound. Nonspecific binding will be measured in the presence of 20 μM GTPγS, and basal [$^{35}$S]GTPγS binding determined in the absence of agonist. After harvesting, net-stimulated [$^{35}$S]GTPγS binding will be defined as agonist-stimulated binding minus basal [$^{35}$S] GTPγS binding. Percentage of maximal stimulation will be defined as [net-stimulated [$^{35}$S]GTPγS binding by test compound/net-stimulated [$^{35}$S]GTPγS binding by CP55,940]× 100%. All data will be normalized as the percentage of maximal stimulation produced by 20 nM CP55,940.

Animals Male and female C57BL/6J mice can be used. Drug-naïve mice will be used for each dose or dose combination to be studied (between-subjects design); a within-subjects design will be used for drug discrimination experiments. Statistical analysis involves comparing $ED_{50}$ values by calculating potency ratios. The standard deviation of the log transformed potency ratio is 0.2 for studies of this type. Power analysis (paired t-test, PASS 2008) was conducted to show that eight males and eight females per group are sufficient to detect at least a 2-fold difference in $ED_{50}$ value with 80% power. A range of drug doses (i.p., s.c. and/or p.o.) will be injected in an ascending order by 0.25-0.5 log unit per injection to assess behavioral endpoints.

Mechanical allodynia CCI will be induced in mice and compounds that show positive binding affinity for cannabinoid receptors will be administered. Mice will undergo testing for mechanical allodynia, via the von Frey test, in which calibrated monofilaments are applied to the plantar hindpaw, and the threshold to achieve a response to the stimulus is determined.

Hypothermia Mice will undergo sequential measures of rectal temperature before and after vehicle and a range of doses of compounds that show positive effects in reversing mechanical allodynia. Rectal temperature will be measured manually by rectal probe.

Drug discrimination Mice will be trained to discriminate 10 mg/kg THC (i.p.) from vehicle under a fixed ratio schedule of food delivery and a double-alternation training sequence in Med Associates operant conditioning chambers as described. The first test will be conducted when, for 5 consecutive or for 6 out of 7 days, at least 80% of the total responses occurred on the correct lever and fewer than 10 responses occurred on the incorrect lever before completion of the first fixed ratio on the correct lever. During tests mice will receive a dose of a drug, or a combination of doses, and responses on either lever will be reinforced. Examples of previous experiments with THC drug discrimination are shown in FIGS. 25A, 25B, 26A, 26B, 27A, 27B, and 28.

Data analysis Data will be analyzed as % effect between subjects (mechanical allodynia, hypothermia) or within subjects (drug discrimination). Data will be plotted as the mean±1 SEM as a function of dose or time. $ED_{50}$ values will be determined by linear regression; significant differences in $ED_{50}$ values will be determined by potency ratios. The $ED_{50}$ values will be considered significantly different when the 95% confidence limits of the potency ratio of $ED_{50}$ values do not include 1. ANOVA will be used to compare effects over time and maxima.

Sex as a biological variable: The extent to which the effects of the novel analogs vary as a function of biological sex is not known; however, female mice are more sensitive to THC than male mice. Experiments have been designed to detect sex differences (n=8 mice per sex per treatment) in both potency and maximum effects. Up to 25 molecules per year can be tested in each in vivo assay, allowing for the examination of numerous compounds.

The studies described herein are anticipated to find novel CB receptor ligands, including both agonists and antagonists. This will be evidenced by relatively high binding affinity at CB receptors (as compared with our standard CP55,940); agonist versus antagonist activity will be determined both in the [$^{35}$S]GTPγS binding assay and in our chosen behavioral screens. It is expected that the disclosed ax-CBN analogs will produce antinociceptive effects at relatively small doses as compared with THC; that is, as compared with THC, ax-CBN analogs will exhibit a larger, more favorable, difference in potency for producing wanted (anti-allodynic) versus unwanted (hypothermia) effects. There may be no detectable CB binding for some analogs.

The disclosed compounds can also lack in vitro CB receptor activity, but at the same time produce analgesic effects. THC-like discriminative stimuli are predictive of cannabis-like subjective effects, so it is possible to expect the same type of difference in therapeutic dosing window when drug discrimination data are analyzed in place of hypothermia. Further, drug discrimination will confirm or refute the presence or absence of in vitro CB receptor activity. No effect alone due to negligible efficacy (i.e., antagonism) will be examined by combining the analog with THC to see if there is a rightward shift in the THC dose-response function. Antagonism of antinociceptive, hypothermic, and discriminative stimulus effects by rimonabant will provide evidence of $CB_1$ receptor involvement. Some disclosed analogs could increase the potency and or maximum effectiveness of THC. Both direct CB-like agonist activity or enhancement of THC effects would be of therapeutic interest. For drugs that either produce analgesic effects or enhance THC activity without any evidence of CB binding, we will consult the literature to determine likely sites of action to be examined in future studies (i.e., glycine receptor activity). Antagonism by SR144528 will indicate a $CB_2$ receptor mechanism, and this activity would produce reversal of mechanical allodynia. Further studies can be carried out to assess additional analogs with $CB_2$ receptor agonist activity.

Having gram-scale access to ax-CBNs by the aforementioned synthetic procedure, the effect of ax-CBNs vs. THC in behavioral and analgesic studies was examined. To determine whether ax-CBN produces overt physiological effects similar to THC, ax-CBN was assessed in a modified version of the tetrad assay, which consists of measuring acute thermal antinociception, body temperature, as well as locomotion and is generally used to screen CB1 receptor agonists. Mice were given vehicle, THC (10-56 mg/kg) or ax-CBN (56-320 mg/kg) and were tested in the three assays (FIGS. 25A, 25B, 26A, 26B, 27A, 27B, and 28). Both THC and ax-CBN dose-relatedly produced thermal antinociception, hypothermia and decreased locomotion. Given that THC is well-established to produce anti-pain behavioral effects in numerous animal studies, ax-CBN was also tested in a mouse model of neuropathic pain. Chronic constriction injury (CCI) of the sciatic nerve is widely used as a model of neuropathic pain and produces increased sensitivity to thermal heat, termed thermal hyperalgesia, as well as an increase in light touch sensitivity, termed mechanical allodynia. Both THC and ax-CBN dose-relatedly reversed CCI-induced thermal hyperalgesia within 30 min after injection, which persisted for at least 6 h (FIGS. 25A, 25B, 26A, 26B, 27A, 27B, and 28). THC and ax-CBN also dose-relatedly reversed CCI-induced mechanical allodynia within 30 min after intraperitoneal administration, which persisted for at least 3 h. Analysis reveals that ax-CBN reverses mechanical allodynia and thermal hyperalgesia in an equi-potent manner. THC is less potent in the reversal of mechanical allodynia than in the reversal of thermal hyperalgesia. Further, THC produces cannabimimetic effects at doses required to reverse mechanical allodynia. Meanwhile, the doses of ax-CBN needed to reverse mechanical allodynia are about 2-fold lower than those that produce cannabimimetic effects. Therefore, ax-CBN has a larger therapeutic dosing window than THC in our mouse model of neuropathic pain. Further, ax-CBN and axially-chiral cannabinols may hold therapeutic promise in the treatment of chronic pain with fewer dose-limiting cannabimimetic effects.

Statistical results of one-way ANOVA examining the dose effects of THC and ax-CBN in cannabinoid-related physiological alterations and behavioral alterations in a model of neuropathic pain are presented in Table 2:

TABLE 2

Effects of THC and ax-CBN in Physiological and Behavioral Alterations in a Model of Neuropathic Pain

| Treatment | Dose |
|---|---|
| Cannabinoid-related physiological alterations | |
| Tail-flick Analgesia | |
| THC | $F(3, 35) = 7.22$; $P < 0.0001$ |
| ax-CBN | $F(4, 45) = 9.69$; $P < 0.001$ |
| Body Temperature | |
| THC | $F(3, 35) = 23.13$; $P < 0.0001$ |
| ax-CBN | $F(4, 45) = 17.42$; $P < 0.0001$ |
| Locomotion | |
| THC | $F(3, 35) = 35.29$; $P < 0.0001$ |
| ax-CBN | $F(4, 45) = 18.36$; $P < 0.0001$ |
| Behavioral alterations in a neuropathic pain model | |
| Mechanical Allodynia | |
| THC | $F(3, 44) = 26.56$; $P < 0.0001$ |
| ax-CBN | $F(4, 55) = 20.81$; $P < 0.0001$ |
| Thermal Hyperalgesia | |
| THC | $F(3, 22) = 23.44$; $P < 0.0001$ |
| ax-CBN | $F(4, 25) = 5.52$; $P < 0.01$ |

Statistical results of two-way ANOVA examining the interaction of dose and time-related effects of THC and ax-CBN in behavioral alterations in a model of neuropathic pain are presented in Table 3:

TABLE 3

Interaction of Dose and Time-Related Effects of THC and ax-CBN in Behavioral Alterations in a Model of Neuropathic Pain

| Drug | Interaction of treatment and time |
|---|---|
| Mechanical Allodynia | |
| THC | $F(7, 98) = 4.81$; $P < 0.0001$ |
| AX-CBN | $F(7, 98) = 2.98$; $P < 0.01$ |
| Thermal Hyperalgesia | |
| THC | $F(7, 70) = 10.71$; $P < 0.0001$ |
| AX-CBN | $F(7, 70) = 5.99$; $P < 0.0001$ |

Calculated $ED_{50}$ values for ax-CBN and THC to reverse allodynia and thermal hyperalgesia, as well as to produce acute antinociception, hypothermia, and hypolocomotion are shown in Table 4 below, along with selected potency ratios:

TABLE 4

$ED_{50}$ Values to Reverse Allodynia and Thermal Hyperalgesia

| | ax-CBN | THC |
|---|---|---|
| Allodynia $ED_{50}$ ((95% CL) mg/kg) | 153.01 (130.40-179.53) | 30.32 (26.68-34.47) |
| Thermal Hyperalgesia $ED_{50}$ ((95% CL) mg/kg) | 126.01 (95.88-165.62) | 15.88 (13.58-18.56) |
| Antinociception $ED_{50}$ ((95% CL) mg/kg) | N.A. | N.A. |
| Body Temp. $ED_{50}$ ((95% CL) mg/kg) | 308.98 (201.28-471.29) | 17.51 (10.98-27.93) |
| Hypolocomotion $ED_{50}$ ((95% CL) mg/kg) | 290.20 (233.10-319.27) | 25.53 (18.14-30.54) |

TABLE 4-continued

| ED$_{50}$ Values to Reverse Allodynia and Thermal Hyperalgesia | | |
|---|---|---|
| | ax-CBN | THC |
| Potency Ratio (Thermal Hyperalgesia/Allodynia) | 0.82 (0.53-1.27) | 0.52 (0.39-0.70) |
| Potency Ratio (Temp/Allodynia) | 2.01 (1.12-3.61) | 0.58 (0.32-1.05) |
| Potency Ratio (Locomotion/Allodynia) | 1.89 (1.29-2.45) | 0.84 (0.53-1.14) |

Computational Studies

A computational study was carried out to investigate the physical properties of axially chiral cannabinols and rationalize the observed effects. Ground state conformations of THC, CBN and ax-CBN with different R groups were locally optimized with the wB97X DFT functional and the 6-31G(d) basis set, using the Gaussian 09 electronic structure package, in the presence of water as the solvent. The dihedral angles (see bolded bonds in the scheme presented below) were computed for each energy minimum conformation. The dihedral angle of ax-CBNs increases as the substituent at C10 gets bulkier and the dihedral angle is closest to that of THC in the presence of an isopropyl or a tert-butyl group.

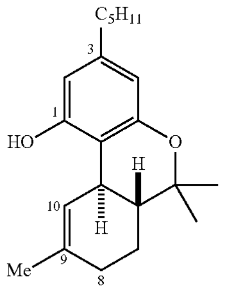

(−)-trans-Δ$^9$-THC
48.04°

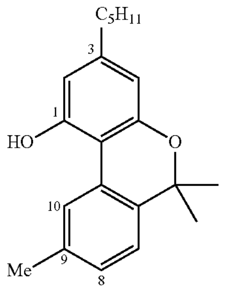

CBN
19.25°

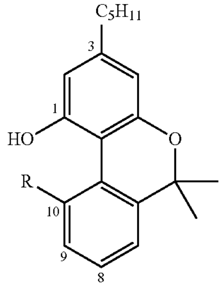

R = $CH_2OH$, 38.15°
R = $CH_3$, 38.33°
R = i-Pr, 41.56°
R = t-Bu, 42.13°

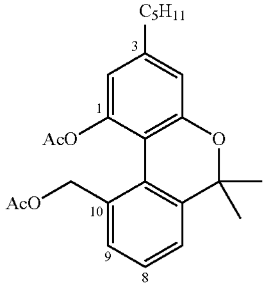

37.48°

Figure 2E:
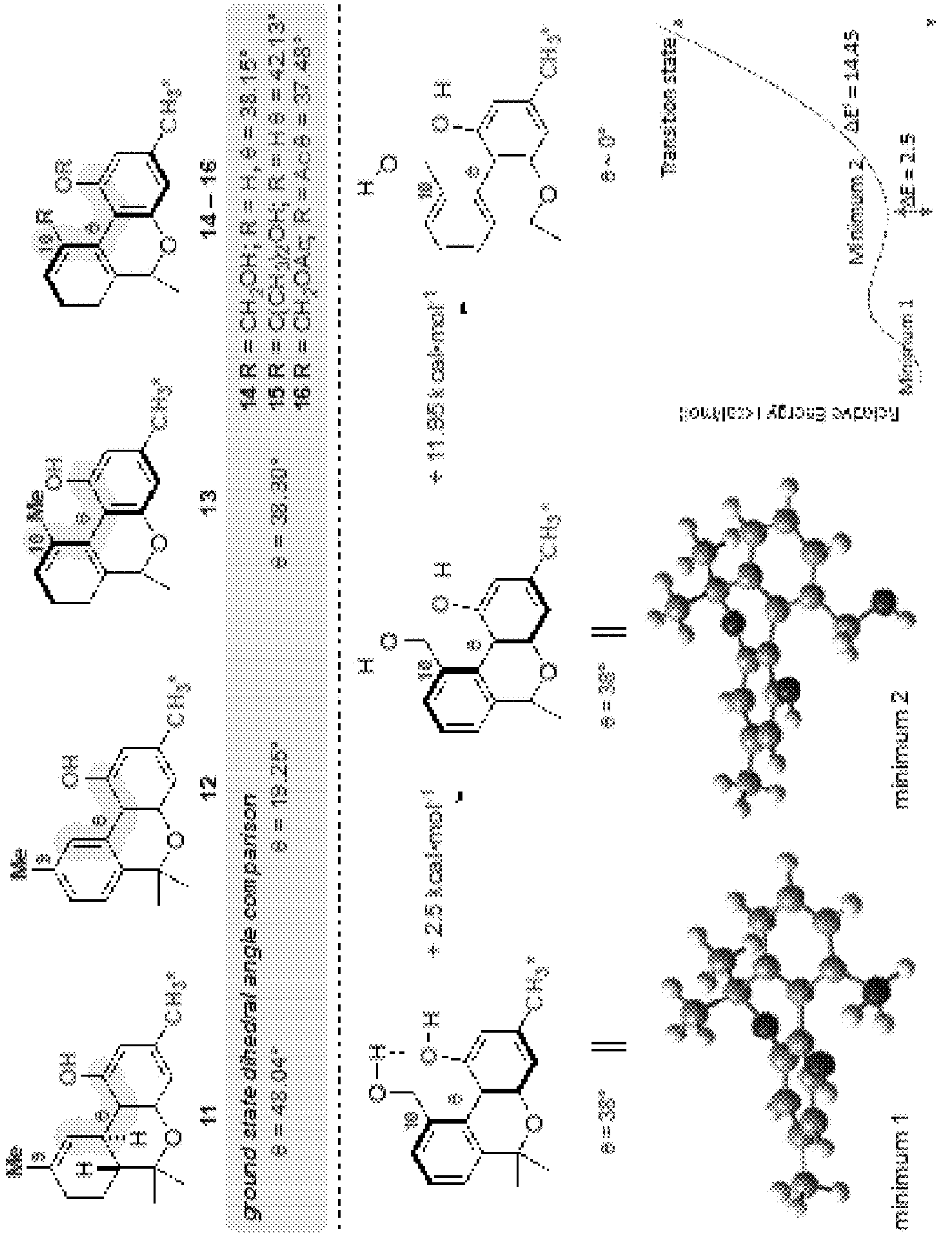

In the ground state conformation, ax-CBN (R=CH2OH) tends to form an intramolecular hydrogen bond with the phenol hydroxy group (FIG. 2E). A relaxed potential energy surface (PES) scan was carried out to identify the rotational barrier for the conversion of the global minima (minimum 1) to the conformation required to perform the interconversion of the enantiomer (minimum 2). The dihedral scan structures were generated through energy minimization with a constraint on the selected torsion. This data supports that these structures have considerable three-dimensionality, and are rapidly equilibrating.

Transition states can be localized through scanning the structural parameters associated with the reaction pathway. A two-dimensional torsional scan was performed in which the dihedral angle (D) and the improper angle (A) corresponding to the inversion in the biaryl carbon framework is fixed to certain values. All other degrees of freedom apart from D and A were optimized. The transition state analysis reveals that interconversion has a barrier of 14.45 kcal/mol, hence in the axially chiral CBNs both enantiomers are equally stable.

Figure 29:
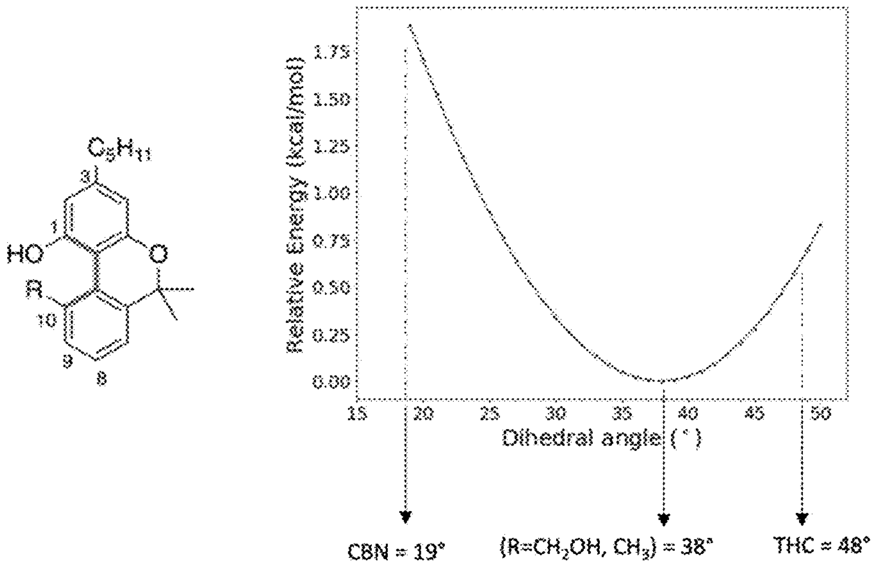
FIG. 29 shows a dihedral angle scan comparison of THC with analog ax-CBN ($R=CH_2OH$).

To determine the energy required to obtain the dihedral of THC by an analogous ax-CBN, a relaxed dihedral scan (FIG. 29) was performed on ax-CBN (R=$CH_2OH$) imposing a constraint on the torsion. This change requires less than 1 kcal/mol, whereas CBN requires a comparatively higher energy. This indicates that axially chiral cannabinoids can be a promising candidate in place of THC than CBN.

Cartesian coordinates of the optimized geometries 11-16 (FIG. 2E) at ωB97X/6-31G(d) level with implicit solvation are provided in the following tables:

TABLE 5

| Cartesian Coordinates for Structure 11 | | | |
|---|---|---|---|
| O | 0.710822 | 1.916979 | −0.506279 |
| C | 1.369403 | 0.745203 | −0.282298 |
| C | 2.734916 | 0.762562 | −0.591785 |
| C | 3.521031 | −0.357464 | −0.365582 |
| C | 2.930750 | −1.488395 | 0.205698 |
| C | 1.573177 | −1.494511 | 0.507220 |
| C | 0.739571 | −0.399920 | 0.217834 |
| C | −0.754076 | −0.394826 | 0.494845 |
| C | −1.511743 | −1.622218 | 0.018744 |
| C | −2.794430 | −1.587096 | −0.353068 |
| C | −3.607400 | −0.312067 | −0.359723 |
| C | −2.875298 | 0.885789 | 0.256008 |
| C | −1.400607 | 0.843353 | −0.142790 |
| C | −0.578556 | 2.107475 | 0.128005 |
| O | 0.998537 | −2.571246 | 1.119859 |
| C | −3.523826 | −2.821050 | −0.813174 |
| C | −0.360898 | 2.401480 | 1.611663 |
| C | −1.155186 | 3.327945 | −0.578096 |
| H | 3.161494 | 1.677088 | −0.995221 |
| H | −0.888104 | −0.327342 | 1.587615 |
| H | −4.559494 | −0.483817 | 0.160624 |
| H | −2.960291 | 0.854211 | 1.350655 |
| H | 1.674661 | −3.248731 | 1.259861 |
| H | −3.936942 | −2.678576 | −1.820410 |
| H | 0.206261 | 3.330774 | 1.727134 |
| H | −0.429454 | 4.146629 | −0.543255 |
| H | −1.375949 | 3.103081 | −1.627072 |
| H | 3.534909 | −2.366216 | 0.431040 |
| H | −0.979984 | −2.569384 | 0.009893 |
| H | −3.353363 | 1.813957 | −0.075343 |
| H | −1.356181 | 0.704516 | −1.234221 |
| H | −2.866650 | −3.696121 | −0.832161 |
| H | −4.372911 | −3.043256 | −0.153822 |
| H | 0.194351 | 1.598973 | 2.107003 |
| H | −1.322144 | 2.520755 | 2.123144 |
| H | −2.073653 | 3.666203 | −0.090113 |
| H | −3.879365 | −0.085515 | −1.401925 |
| C | 4.990461 | −0.359997 | −0.705114 |
| H | 5.595930 | −0.637675 | 0.164667 |
| H | 5.207715 | −1.086847 | −1.496060 |
| H | 5.320562 | 0.623841 | −1.051000 |

TABLE 6

| Cartesian Coordinates for Structure 12 | | | |
|---|---|---|---|
| C | −0.841152 | −0.381388 | −0.022135 |
| C | −1.679072 | −1.495889 | −0.150347 |
| C | −1.421374 | 0.900070 | 0.015316 |
| C | −2.806189 | 1.027296 | −0.043601 |
| C | −3.623813 | −0.093322 | −0.146589 |
| C | −3.067218 | −1.370140 | −0.204852 |
| H | −4.704068 | 0.029949 | −0.191371 |
| H | −3.264162 | 2.012217 | −0.011270 |
| C | 0.638143 | −0.466035 | −0.002346 |
| C | 1.401518 | −1.616638 | 0.272975 |
| C | 2.790129 | −1.609379 | 0.160355 |
| C | 3.473630 | −0.453987 | −0.219170 |
| C | 1.357652 | 0.692031 | −0.336613 |
| C | 2.744533 | 0.705238 | −0.461269 |
| O | 0.751332 | −2.748940 | 0.660111 |
| H | 3.343689 | −2.522647 | 0.373759 |
| C | 4.977988 | −0.455725 | −0.315441 |
| H | 3.235406 | 1.634577 | −0.736663 |
| H | 5.430477 | −0.333185 | 0.675640 |
| H | 5.335502 | 0.362688 | −0.947097 |
| H | 5.348314 | −1.398875 | −0.729461 |
| H | 1.405015 | −3.442663 | 0.826044 |
| O | 0.708309 | 1.860004 | −0.594405 |
| C | −0.505079 | 2.105647 | 0.155210 |
| C | −0.144774 | 2.347091 | 1.623910 |
| C | −1.066943 | 3.375154 | −0.471538 |
| H | −1.364642 | 3.198112 | −1.509355 |
| H | −0.296793 | 4.151952 | −0.453344 |
| H | −1.931476 | 3.742637 | 0.087589 |
| H | 0.314020 | 1.458958 | 2.070135 |
| H | −1.048946 | 2.586360 | 2.192708 |
| H | 0.556175 | 3.184777 | 1.706032 |
| H | −1.239443 | −2.484831 | −0.211701 |
| C | −3.941891 | −2.595684 | −0.303579 |
| H | −3.448084 | −3.392597 | −0.868642 |
| H | −4.170488 | −2.994478 | 0.692083 |
| H | −4.894153 | −2.367499 | −0.792464 |

TABLE 7

| Cartesian Coordinates for Structure 13 | | | |
|---|---|---|---|
| C | −0.938377 | 0.584912 | −0.04373 |
| C | −1.567751 | 1.815482 | −0.32443 |
| C | −1.730901 | −0.574755 | 0.089052 |
| C | −3.117961 | −0.482743 | 0.121171 |
| C | −3.737656 | 0.754016 | −0.02411 |
| C | −2.964360 | 1.876871 | −0.27919 |
| H | −3.449954 | 2.830367 | −0.4784 |
| H | −4.821299 | 0.830910 | 0.011363 |
| H | −3.724260 | −1.375383 | 0.245598 |
| C | 0.531048 | 0.382770 | −0.00563 |
| C | 1.489380 | 1.277736 | 0.497856 |
| C | 2.855771 | 1.021845 | 0.360774 |
| C | 3.308683 | −0.164642 | −0.21195 |
| C | 1.017506 | −0.858859 | −0.44722 |
| C | 2.372931 | −1.127721 | −0.58812 |
| O | 1.054947 | 2.378016 | 1.167295 |
| H | 3.571919 | 1.752547 | 0.733448 |
| C | 4.783628 | −0.418441 | −0.39098 |
| H | 2.681451 | −2.101146 | −0.95963 |
| H | 5.091538 | −0.190810 | −1.41837 |
| H | 5.030398 | −1.467750 | −0.20129 |
| H | 5.381910 | 0.204627 | 0.280403 |
| H | 1.819470 | 2.906960 | 1.434841 |
| O | 0.133827 | −1.853656 | −0.73919 |
| C | −1.016860 | −1.920087 | 0.144445 |
| C | −1.841807 | −3.062599 | −0.43435 |
| C | −0.560069 | −2.261184 | 1.565254 |
| H | 0.069135 | −1.471821 | 1.987249 |
| H | 0.004972 | −3.199559 | 1.563069 |
| H | −1.435551 | −2.380460 | 2.211444 |
| H | −2.206638 | −2.812609 | −1.43498 |
| H | −2.696388 | −3.298096 | 0.205436 |
| H | −1.212863 | −3.955301 | −0.5012 |

TABLE 7-continued

| Cartesian Coordinates for Structure 13 | | | |
|---|---|---|---|
| C | −0.830434 | 3.056333 | −0.76816 |
| H | −0.585650 | 3.711441 | 0.071518 |
| H | 0.109583 | 2.808776 | −1.26942 |
| H | −1.454579 | 3.618830 | −1.47004 |

TABLE 8

| Cartesian Coordinates for Structure 14 | | | |
|---|---|---|---|
| C | −0.934191 | 0.222829 | −0.084061 |
| C | −1.752239 | 1.331202 | −0.370847 |
| C | −1.540702 | −1.040334 | 0.088139 |
| C | −2.924514 | −1.153196 | 0.155469 |
| C | −3.729867 | −0.026933 | 0.010959 |
| C | −3.140247 | 1.192192 | −0.283288 |
| H | −3.761526 | 2.063970 | −0.479350 |
| H | −4.810853 | −0.115720 | 0.078087 |
| C | −1.242553 | 2.674732 | −0.859962 |
| H | −3.386904 | −2.124068 | 0.309214 |
| C | 0.551523 | 0.246724 | −0.047321 |
| C | 1.369134 | 1.277593 | 0.442800 |
| C | 2.758051 | 1.210984 | 0.342706 |
| C | 3.384705 | 0.087976 | −0.195424 |
| C | 1.216394 | −0.920361 | −0.456992 |
| C | 2.599158 | −0.999911 | −0.569229 |
| O | 0.782987 | 2.343394 | 1.066806 |
| H | 3.357344 | 2.042466 | 0.709948 |
| C | 4.883890 | 0.042835 | −0.341104 |
| H | 3.045735 | −1.927788 | −0.915634 |
| H | 5.183453 | 0.386414 | −1.338271 |
| H | 5.264365 | −0.975478 | −0.216513 |
| H | 5.376035 | 0.688753 | 0.392161 |
| O | −1.429834 | 3.716299 | 0.082871 |
| H | −1.831497 | 2.960903 | −1.737856 |
| H | −0.196458 | 2.604294 | −1.179253 |
| H | 1.475271 | 2.949937 | 1.366234 |
| O | 0.487987 | −2.035263 | −0.741261 |
| C | −0.635408 | −2.264643 | 0.149909 |
| C | −1.284996 | −3.520866 | −0.416442 |
| C | −0.125778 | −2.520345 | 1.570473 |
| H | 0.372916 | −1.638829 | 1.984439 |
| H | 0.579949 | −3.357957 | 1.571228 |
| H | −0.968957 | −2.770782 | 2.222033 |
| H | −1.688868 | −3.334357 | −1.415862 |
| H | −2.090983 | −3.876981 | 0.230488 |
| H | −0.530161 | −4.309925 | −0.482348 |
| H | −0.831853 | 3.491817 | 0.810958 |

TABLE 9

| Cartesian Coordinates for Structure 15 | | | |
|---|---|---|---|
| C | −0.703059 | 0.391179 | −0.100950 |
| C | −1.965188 | −0.252073 | −0.061162 |
| C | −0.657585 | 1.802020 | −0.180685 |
| C | −1.798154 | 2.533469 | −0.486806 |
| C | −3.002996 | 1.873268 | −0.686384 |
| C | −3.079196 | 0.512264 | −0.434157 |
| H | −4.049683 | 0.034378 | −0.507016 |
| H | −3.893363 | 2.425393 | −0.975210 |
| C | −2.258422 | −1.694969 | 0.446006 |
| H | −1.751331 | 3.614764 | −0.580189 |
| C | 0.635933 | −0.259208 | −0.070430 |
| C | 1.010598 | −1.415156 | −0.768554 |
| C | 2.294471 | −1.946554 | −0.663464 |
| C | 3.274378 | −1.303435 | 0.091921 |
| C | 1.679597 | 0.435500 | 0.557294 |
| C | 2.963561 | −0.079995 | 0.681680 |
| O | 0.085431 | −2.019195 | −1.578085 |
| H | 2.533834 | −2.868221 | −1.191268 |
| C | 4.649022 | −1.902589 | 0.240298 |
| H | 3.716538 | 0.504550 | 1.203182 |
| H | 4.735215 | −2.436289 | 1.194017 |

TABLE 9-continued

| Cartesian Coordinates for Structure 15 | | | |
|---|---|---|---|
| H | 5.421562 | −1.127549 | 0.229021 |
| H | 4.863132 | −2.616485 | −0.560447 |
| O | −2.473334 | −2.583338 | −0.647695 |
| H | 0.508749 | −2.753837 | −2.045588 |
| O | 1.433442 | 1.690031 | 1.028579 |
| C | 0.665454 | 2.507592 | 0.107029 |
| C | 0.475272 | 3.812558 | 0.871952 |
| C | 1.471414 | 2.747645 | −1.172004 |
| H | 1.653737 | 1.814271 | −1.713423 |
| H | 2.434651 | 3.209320 | −0.929681 |
| H | 0.915821 | 3.420566 | −1.832813 |
| H | −0.133478 | 3.651465 | 1.766466 |
| H | −0.002660 | 4.574202 | 0.250937 |
| H | 1.456129 | 4.190227 | 1.175975 |
| H | −1.644473 | −2.566475 | −1.153101 |
| C | −1.184893 | −2.255600 | 1.393170 |
| H | −0.257875 | −2.516011 | 0.885097 |
| H | −0.951071 | −1.543169 | 2.192024 |
| H | −1.572360 | −3.170530 | 1.852280 |
| C | −3.575927 | −1.722543 | 1.235667 |
| H | −4.441119 | −1.519764 | 0.601343 |
| H | −3.710624 | −2.723107 | 1.657680 |
| H | −3.561321 | −0.997926 | 2.055778 |

For Structure 16 (FIG. 2E), R=$CH_2OH$ or $CH_2OAc$. Cartesian coordinates of the minimum 1, minimum 2, and transition state structures for the atropisomerism at ωB97X/6-31G(d) are provided in the tables below:

TABLE 10

| Cartesian Coordinates for Minimum 1 | | | |
|---|---|---|---|
| C | 0.933797 | 0.220677 | −0.085103 |
| C | 1.752918 | 1.329372 | −0.366700 |
| C | 1.538736 | −1.042978 | 0.087660 |
| C | 2.922279 | −1.156314 | 0.159876 |
| C | 3.728403 | −0.029846 | 0.020549 |
| C | 3.140484 | 1.190039 | −0.274280 |
| H | 3.762764 | 2.061834 | −0.466997 |
| H | 4.809083 | −0.119096 | 0.091886 |
| C | 1.244008 | 2.670735 | −0.862360 |
| H | 3.383978 | −2.127490 | 0.313891 |
| C | −0.551597 | 0.246983 | −0.048739 |
| C | −1.366391 | 1.279623 | 0.442371 |
| C | −2.755609 | 1.214809 | 0.345116 |
| C | −3.384781 | 0.092520 | −0.191633 |
| C | −1.218548 | −0.919049 | −0.457496 |
| C | −2.601621 | −0.996621 | −0.567061 |
| O | −0.776853 | 2.345102 | 1.063683 |
| H | −3.353120 | 2.047273 | 0.713047 |
| C | −4.884322 | 0.049470 | −0.334564 |
| H | −3.050424 | −1.923694 | −0.912741 |
| H | −5.374005 | 0.700379 | 0.395912 |
| H | −5.266535 | −0.967423 | −0.203751 |
| H | −5.184874 | 0.387966 | −1.333175 |
| O | 1.438570 | 3.718263 | 0.072402 |
| H | 0.196583 | 2.600967 | −1.176808 |
| H | 1.830023 | 2.949505 | −1.744648 |
| H | −1.467538 | 2.952051 | 1.365952 |
| O | −0.491611 | −2.034545 | −0.743661 |
| C | 0.632259 | −2.266629 | 0.146255 |
| C | 0.123024 | −2.525393 | 1.566401 |
| C | 1.281026 | −3.521685 | −0.423605 |
| H | 1.684519 | −3.332738 | −1.422720 |
| H | 0.525917 | −4.310350 | −0.491168 |
| H | 2.087226 | −3.879711 | 0.222011 |
| H | −0.375297 | −1.644560 | 1.982308 |
| H | 0.966252 | −2.777482 | 2.217263 |
| H | −0.583005 | −3.362752 | 1.565522 |
| H | 0.843215 | 3.500474 | 0.804709 |

TABLE 11

| Cartesian Coordinates for Minimum 2 | | | |
|---|---|---|---|
| C | 0.904105 | 0.163610 | 0.104825 |
| C | 1.801109 | 1.242844 | −0.035189 |
| C | 1.418917 | −1.149462 | 0.136369 |
| C | 2.790603 | −1.368880 | 0.199539 |
| C | 3.670505 | −0.292540 | 0.183779 |
| C | 3.172836 | 0.993082 | 0.030374 |
| H | 3.863357 | 1.823830 | −0.081121 |
| H | 4.742512 | −0.461763 | 0.242595 |
| C | 1.359286 | 2.663746 | −0.356172 |
| H | 3.183226 | −2.380497 | 0.246363 |
| C | −0.574854 | 0.286516 | 0.086332 |
| C | −1.340129 | 1.320187 | 0.651374 |
| C | −2.721113 | 1.383361 | 0.461972 |
| C | −3.393591 | 0.382185 | −0.236943 |
| C | −1.297239 | −0.771919 | −0.488555 |
| C | −2.671866 | −0.721938 | −0.686963 |
| O | −0.704614 | 2.234497 | 1.432650 |
| H | −3.277969 | 2.213985 | 0.892598 |
| C | −4.879342 | 0.479843 | −0.470344 |
| H | −3.165913 | −1.565825 | −1.160490 |
| H | −5.375779 | 1.020880 | 0.341057 |
| H | −5.334533 | −0.511458 | −0.555219 |
| H | −5.087542 | 1.018972 | −1.402114 |
| O | 2.301854 | 3.353115 | −1.166660 |
| H | 1.161324 | 3.223502 | 0.561845 |
| H | 0.419117 | 2.633361 | −0.917314 |
| H | −1.342821 | 2.900800 | 1.723961 |
| O | −0.639000 | −1.905388 | −0.856979 |
| C | 0.427846 | −2.303701 | 0.044227 |
| C | −0.156870 | −2.658923 | 1.413665 |
| C | 1.009455 | −3.544851 | −0.620557 |
| H | 1.466313 | −3.294977 | −1.582654 |
| H | 0.204785 | −4.266572 | −0.789504 |
| H | 1.761064 | −4.019282 | 0.015824 |
| H | −0.613100 | −1.788904 | 1.895152 |
| H | 0.639965 | −3.029617 | 2.066239 |
| H | −0.915877 | −3.441427 | 1.306747 |
| H | 2.888016 | 3.848244 | −0.582457 |

TABLE 12

| Cartesian Coordinates for Transition State | | | |
|---|---|---|---|
| C | 0.853639 | −0.127135 | 0.096504 |
| C | 1.838466 | −1.149274 | 0.176601 |
| C | 1.324122 | 1.195935 | −0.074530 |
| C | 2.676510 | 1.465036 | −0.271447 |
| C | 3.605832 | 0.441373 | −0.318860 |
| C | 3.179751 | −0.848297 | −0.054872 |
| H | 3.902605 | −1.651955 | 0.034111 |
| H | 4.655683 | 0.652707 | −0.503253 |
| C | 1.552386 | −2.643255 | 0.109765 |
| H | 3.009021 | 2.492463 | −0.393226 |
| C | −0.624958 | −0.312136 | −0.065588 |
| C | −1.343789 | −1.526475 | −0.162147 |
| C | −2.729586 | −1.593116 | −0.147901 |
| C | −3.502746 | −0.443959 | −0.013478 |
| C | −1.447614 | 0.826762 | 0.024658 |
| C | −2.843565 | 0.769919 | 0.048768 |
| O | −0.660261 | −2.703577 | −0.074878 |
| H | −3.211594 | −2.565730 | −0.247846 |
| C | −5.006980 | −0.520931 | 0.006023 |
| H | −3.382928 | 1.708219 | 0.138032 |
| H | −5.408712 | −0.550071 | −1.013803 |
| H | −5.441201 | 0.349162 | 0.507330 |
| H | −5.353168 | −1.422076 | 0.522516 |
| O | 2.795984 | −3.328916 | 0.225628 |
| H | −1.275375 | −3.422548 | −0.265346 |
| O | −0.976139 | 2.086886 | 0.104844 |
| C | 0.418682 | 2.409702 | 0.077839 |
| C | 0.489852 | 3.286211 | −1.174639 |

TABLE 12-continued

| Cartesian Coordinates for Transition State | | | |
|---|---|---|---|
| C | 0.699945 | 3.072669 | 1.433059 |
| H | 0.542002 | 2.352701 | 2.242042 |
| H | 0.020210 | 3.919244 | 1.577296 |
| H | 1.732226 | 3.432246 | 1.487831 |
| H | 0.295862 | 2.690427 | −2.071977 |
| H | 1.465134 | 3.768673 | −1.279678 |
| H | −0.273286 | 4.067180 | −1.102113 |
| H | 2.608858 | −4.265900 | 0.095885 |
| H | 0.906393 | −2.925203 | 0.914811 |
| H | 1.091921 | −2.882855 | −0.825898 |

A variable temperature study (VT-NMR) was done to calculate the barrier rotation of axially chiral CBN derivative (FIG. 2D).

Figure 2F:
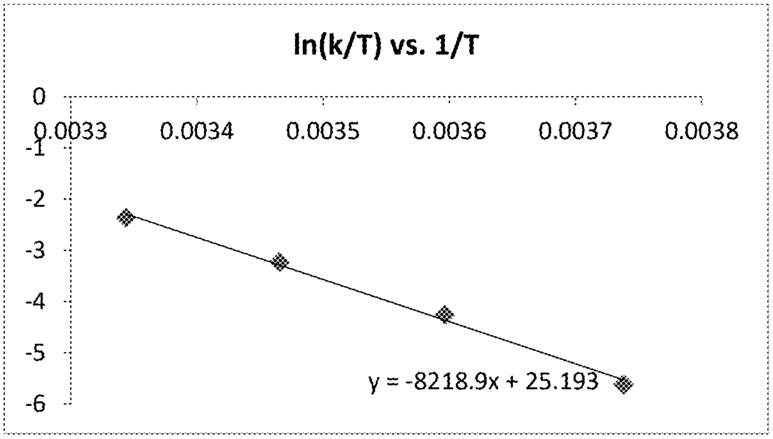

The barrier to rotation was measured by selective inversion of one of the methylene protons, followed by monitoring the intensity of its signal and of that of its isochronous partner, as they both relax to equilibrium. These intensities are functions of the exchange rate (k) and of the longitudinal relaxation rates (R1). These rates were determined by iteratively fitting the two R1s in the non-selective inversion-recovery spectra, and the exchange rate k in the selective inversion spectra, using the CIFIT program of Bain and co-workers for four values of temperature in the range −5 to 25° C. 137 A plot ln(k/T) vs. 1/T (FIG. 2F) provided the thermodynamic parameters ΔH=16.3 kcal/mol, ΔS=2.85 cal/mol/K and ΔG=15.5 kcal/mol.

$^{1}H$ and $^{1}H$-$^{13}C$ gHSQC and gHMBC NMR spectra were obtained on Varian INOVA spectrometer, operating at 500 MHz for proton, equipped with a 5 mm indirect detection probe and z-axis gradients. Chemical shifts, reported in δ (ppm), were referenced on the solvent, on the TMS scale for $^{1}H$ and $^{13}C$. The temperature was calibrated to the neat methanol standard. The signal of the methylene proton at lower field was inverted. The intensity was monitored over 11 time intervals, in spectra with an acquisition time of 3.3 s and a relaxation delay of 5 s, taken in 4 transients. The intensities of the two signals in the selective inversion spectra (e1 and e2) and in the non-selective ones (t1 and t2) are given in Table 13.

TABLE 13

Intensities of Inverted Line (1) and Isochronous Line (2) in Selective Inversion (e) and Non-Selective Inversion (t) Experiments as a Function of Monitoring Time (d2)

| Temperature (° C.) | −5 | | | | 5 | | | |
|---|---|---|---|---|---|---|---|---|
| d2 (s) | e1 | e2 | t1 | t2 | e1 | e2 | t1 | t2 |
| 0.0125 | −0.688 | 0.894 | −0.894 | −0.902 | −0.541 | 0.698 | −0.886 | −0.892 |
| 0.025 | −0.633 | 0.873 | −0.843 | −0.851 | −0.456 | 0.651 | −0.856 | −0.863 |
| 0.05 | −0.526 | 0.851 | −0.760 | −0.777 | −0.299 | 0.564 | −0.776 | −0.789 |
| 0.1 | −0.330 | 0.802 | −0.601 | −0.627 | −0.067 | 0.462 | −0.641 | −0.661 |
| 0.2 | −0.028 | 0.738 | −0.324 | −0.360 | 0.214 | 0.412 | −0.393 | −0.415 |
| 0.4 | 0.381 | 0.720 | 0.093 | 0.052 | 0.478 | 0.501 | 0.013 | −0.022 |
| 0.8 | 0.740 | 0.801 | 0.570 | 0.537 | 0.731 | 0.729 | 0.479 | 0.468 |
| 1.6 | 0.942 | 0.940 | 0.910 | 0.896 | 0.919 | 0.919 | 0.879 | 0.877 |
| 3.2 | 0.980 | 0.980 | 1.001 | 0.995 | 0.990 | 0.990 | 1.004 | 1.003 |
| 6.4 | 0.995 | 0.992 | 1.000 | 1.000 | 1.000 | 0.998 | 1.004 | 1.006 |
| 12.8 | 1.000 | 1.000 | 1.000 | 1.000 | 1.000 | 1.000 | 1.000 | 1.000 |
| Temperature (° C.) | 15 | | | | 25 | | | |
| d2 (s) | e1 | e2 | t1 | t2 | e1 | e2 | t1 | t2 |
| 0.0125 | −0.317 | 0.410 | −0.889 | −0.894 | −0.156 | 0.184 | −0.887 | −0.891 |
| 0.025 | −0.204 | 0.329 | −0.855 | −0.863 | −0.055 | 0.110 | −0.854 | −0.863 |
| 0.05 | −0.050 | 0.237 | −0.789 | −0.796 | 0.041 | 0.078 | −0.805 | −0.806 |
| 0.1 | 0.112 | 0.196 | −0.663 | −0.675 | 0.111 | 0.114 | −0.697 | −0.703 |
| 0.2 | 0.256 | 0.262 | −0.449 | −0.458 | 0.212 | 0.210 | −0.503 | −0.507 |
| 0.4 | 0.434 | 0.432 | −0.090 | −0.098 | 0.373 | 0.373 | −0.178 | −0.178 |
| 0.8 | 0.667 | 0.664 | 0.386 | 0.382 | 0.611 | 0.604 | 0.289 | 0.285 |
| 1.6 | 0.884 | 0.882 | 0.820 | 0.817 | 0.845 | 0.844 | 0.746 | 0.745 |
| 3.2 | 0.986 | 0.987 | 0.998 | 0.998 | 0.977 | 0.973 | 0.981 | 0.983 |
| 6.4 | 0.999 | 0.999 | 1.010 | 1.010 | 1.003 | 0.999 | 1.007 | 1.006 |
| 12.8 | 1.000 | 1.000 | 1.000 | 1.000 | 1.000 | 1.000 | 1.000 | 1.000 |

The rates of exchange could be measured in the temperature interval −5 to 25° C., and are given in Table 14. Thermodynamic parameters were calculated from the slope and intercept of the ln(k/T) vs. 1/T, (FIG. 2F), ΔH=16.3 kcal/mol, ΔS=2.85 cal/mol/K and ΔG=15.5 kcal/mol (calculations are based on FIG. 2F).

TABLE 14

Rates of Exchange ($s^{-1}$) as a Function of Temperature (° C.)

| Temperature | Corrected | Rate | 1/T | ln(k/T) |
|---|---|---|---|---|
| −5 | −5.64 | 0.974 | 0.003738 | −5.61553 |
| 5 | 4.885 | 3.925 | 0.003597 | −4.26041 |
| 15 | 15.41 | 11.42 | 0.003465 | −3.22957 |
| 25 | 25.93 | 28.13 | 0.003343 | −2.36393 |

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A compound having a structure represented by a formula:

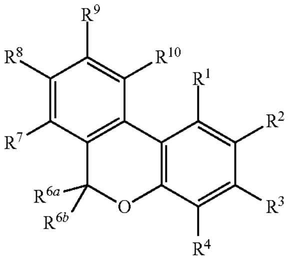

wherein $R^1$ is selected from hydrogen, hydroxyl, methoxy, acetoxy, —$OC_6H_5$, and —$OCH_2C_6H_5$;

wherein each of $R^2$, $R^4$, $R^{6a}$, and $R^{6b}$ is independently selected from hydrogen and C1-C6 alkyl;

wherein $R^3$ is optionally substituted $C_1$-$C_{12}$ alkyl;

wherein $R^7$ and $R^8$ are hydrogen; and wherein $R^9$ is optionally substituted alkyl;

wherein $R^{10}$ is selected from cyano, —$CH_2OH$, —$CH_2OAc$, or optionally substituted alkyl; or wherein $R^9$ is hydrogen and wherein $R^{10}$ is selected from cyano, —$CH_2OH$, —$CH_2OAc$, or methyl;

or a pharmaceutically acceptable salt thereof.

2. The compound of claim 1, wherein $R^1$ is selected from hydroxyl, methoxy, and acetoxy.

3. The compound of claim 1, having a structure represented by a formula:

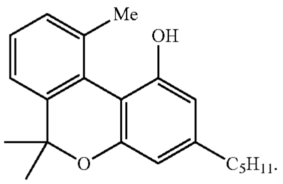

4. A pharmaceutical composition comprising a therapeutically effective amount of a compound of claim 1, or a pharmaceutically acceptable salt, solvate, or polymorph thereof, and a pharmaceutically acceptable carrier.

* * * * *